(12) United States Patent
Beer

(10) Patent No.: US 10,898,317 B2
(45) Date of Patent: Jan. 26, 2021

(54) ACCOMMODATIVE-DISACCOMMODATIVE INTRAOCULAR LENS

(71) Applicant: Carl Zeiss Meditec AG, Jena (DE)

(72) Inventor: Paul Marius Beer, St. Petersburg, FL (US)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 15/153,275

(22) Filed: May 12, 2016

(65) Prior Publication Data

US 2016/0331520 A1    Nov. 17, 2016

Related U.S. Application Data

(62) Division of application No. 13/800,367, filed on Mar. 13, 2013, now Pat. No. 9,364,318.

(Continued)

(51) Int. Cl.
*A61F 2/16*    (2006.01)

(52) U.S. Cl.
CPC .......... *A61F 2/1624* (2013.01); *A61F 2/1629* (2013.01); *A61F 2002/1682* (2015.04); *A61F 2002/1683* (2013.01); *A61F 2002/1686* (2013.01); *A61F 2002/16901* (2015.04); *A61F 2310/00023* (2013.01)

(58) Field of Classification Search
CPC ............ A61F 2/1624; A61F 2002/1682; A61F 2002/16901; A61F 2002/16903; A61F 2002/1683; A61F 2002/1686; A61F 2002/169
See application file for complete search history.

(56) References Cited

U.S. PATENT DOCUMENTS 3,975,779 A    8/1976    Richards et al.
3,979,780 A *  9/1976    Boniuk ..................... A61F 2/16
                                                                623/6.14

(Continued)

FOREIGN PATENT DOCUMENTS

AU    2003294418 A1    6/2004
AU    2003297101 A1    6/2004

(Continued)

OTHER PUBLICATIONS

International Search Report and Written Opinion dated Dec. 4, 2013 in International Application No. PCT/US2013/039708.

(Continued)

*Primary Examiner* — Leslie Lopez
(74) *Attorney, Agent, or Firm* — Goodwin Procter LLP

(57) ABSTRACT

Embodiments of the invention relate to an intraocular lens system having a plurality of haptics for use with an optic. In general, the haptics are adapted to move independently in response to forces associated with a ciliary muscle and/or zonules of an eye when implanted. The optic may be releasably secured to the system using, for example, a plurality of optic securing arms. Alternatively, the optic may be fused to the haptics, which may project radially outward from the optic. A restraining arm may be included to limit movement of the haptics during accommodation and/or disaccommodation. Clamping members may be included for securing the system to a capsular bag of the eye. Methods of implanting the intraocular lens system into the eye are also described.

19 Claims, 26 Drawing Sheets

Related U.S. Application Data

(60) Provisional application No. 61/645,382, filed on May 10, 2012, provisional application No. 61/645,320, filed on May 10, 2012.

(56) References Cited

U.S. PATENT DOCUMENTS

| | | |
|---|---|---|
| 3,991,426 A | 11/1976 | Flom et al. |
| 4,014,049 A * | 3/1977 | Richards .................. A61F 2/16 623/6.51 |
| 4,053,953 A | 10/1977 | Flom et al. |
| 4,056,855 A | 11/1977 | Kelman |
| 4,124,905 A | 11/1978 | Clark |
| 4,149,279 A | 4/1979 | Poler |
| 4,262,370 A | 4/1981 | Hartstein |
| 4,373,218 A | 2/1983 | Schachar |
| 4,463,457 A | 8/1984 | Kelman |
| 4,527,294 A | 7/1985 | Heslin |
| 4,534,069 A | 8/1985 | Kelman |
| 4,575,373 A | 3/1986 | Johnson |
| 4,581,032 A | 4/1986 | Grandon |
| 4,581,033 A | 4/1986 | Callahan |
| 4,588,406 A | 5/1986 | Fedorov et al. |
| 4,666,446 A | 5/1987 | Koziol et al. |
| 4,685,922 A | 8/1987 | Peyman |
| 4,693,717 A | 9/1987 | Michelson |
| 4,718,904 A | 1/1988 | Thornton |
| 4,738,680 A | 4/1988 | Herman |
| 4,781,719 A | 11/1988 | Kelman |
| 4,787,903 A | 11/1988 | Grendahl |
| 4,790,847 A | 12/1988 | Woods |
| 4,842,601 A | 6/1989 | Smith |
| 4,871,363 A | 10/1989 | Kelman |
| 4,878,910 A | 11/1989 | Koziol et al. |
| 4,888,012 A | 12/1989 | Horn et al. |
| 4,888,015 A | 12/1989 | Domino |
| 4,892,543 A | 1/1990 | Turley |
| 4,932,966 A | 6/1990 | Christie et al. |
| 4,932,968 A | 6/1990 | Caldwell et al. |
| 4,936,850 A | 6/1990 | Barrett |
| 4,944,082 A | 7/1990 | Jones et al. |
| 4,950,288 A | 8/1990 | Kelman |
| 4,955,894 A | 9/1990 | Herman |
| 4,963,148 A | 10/1990 | Sulc et al. |
| 4,995,879 A | 2/1991 | Dougherty |
| 5,104,590 A | 4/1992 | Blake |
| 5,108,429 A | 4/1992 | Wiley |
| 5,169,569 A * | 12/1992 | Ingram .................. A61F 2/16 264/1.7 |
| 5,185,107 A | 2/1993 | Blake |
| 5,192,319 A | 3/1993 | Worst |
| RE34,424 E | 10/1993 | Walman |
| 5,282,851 A | 2/1994 | Jacob-LaBarre |
| 5,288,293 A | 2/1994 | O'Donnell, Jr. |
| 5,306,297 A | 4/1994 | Rheinish et al. |
| 5,326,347 A | 7/1994 | Cumming |
| 5,366,500 A | 11/1994 | Schneider et al. |
| 5,423,929 A | 6/1995 | Doyle et al. |
| 5,476,514 A | 12/1995 | Cumming |
| 5,489,302 A | 2/1996 | Skottun |
| 5,496,366 A | 3/1996 | Cumming |
| 5,507,806 A | 4/1996 | Blake |
| 5,527,415 A | 6/1996 | Doyle et al. |
| 5,549,668 A | 8/1996 | O'Donnell, Jr. |
| 5,562,731 A | 10/1996 | Cumming |
| 5,571,177 A | 11/1996 | Deacon et al. |
| 5,578,081 A | 11/1996 | McDonald |
| 5,593,436 A | 1/1997 | Langerman |
| 5,607,472 A | 3/1997 | Thompson |
| 5,674,282 A | 10/1997 | Cumming |
| 5,683,456 A | 11/1997 | Blake |
| 5,702,441 A | 12/1997 | Zhou |
| 5,728,155 A | 3/1998 | Anello et al. |
| 5,728,156 A | 3/1998 | Gupta et al. |
| 5,769,889 A | 6/1998 | Kelman |
| 5,782,911 A | 7/1998 | Herrick |
| 5,800,532 A | 9/1998 | Lieberman |
| 5,803,925 A | 9/1998 | Yang et al. |
| 5,843,187 A | 12/1998 | Bayers |
| 5,855,605 A | 1/1999 | Herrick |
| 5,964,802 A | 10/1999 | Anello et al. |
| 5,984,962 A | 11/1999 | Anello et al. |
| 6,013,101 A | 1/2000 | Israel |
| 6,015,435 A | 1/2000 | Valunin et al. |
| 6,027,531 A | 2/2000 | Tassignon |
| 6,048,364 A | 4/2000 | Skottun |
| 6,051,024 A | 4/2000 | Cumming |
| 6,053,944 A | 4/2000 | Tran et al. |
| 6,083,261 A | 7/2000 | Callahan et al. |
| 6,096,077 A | 8/2000 | Callahan et al. |
| 6,096,078 A | 8/2000 | McDonald |
| 6,110,202 A | 8/2000 | Barraquer et al. |
| 6,139,576 A | 10/2000 | Doyle et al. |
| 6,143,027 A | 11/2000 | Ratner et al. |
| 6,152,959 A | 11/2000 | Portney |
| 6,171,337 B1 | 1/2001 | Galin |
| 6,176,878 B1 | 1/2001 | Gwon et al. |
| 6,179,843 B1 | 1/2001 | Weiler |
| 6,190,410 B1 | 2/2001 | Lamielle et al. |
| 6,197,058 B1 | 3/2001 | Portney |
| 6,197,059 B1 | 3/2001 | Cumming |
| 6,200,342 B1 | 3/2001 | Tassignon |
| 6,200,344 B1 | 3/2001 | Lamielle et al. |
| 6,217,612 B1 | 4/2001 | Woods |
| 6,224,628 B1 | 5/2001 | Callahan et al. |
| 6,228,115 B1 | 5/2001 | Hoffmann et al. |
| 6,241,777 B1 | 6/2001 | Kellan |
| 6,251,312 B1 | 6/2001 | Phan et al. |
| 6,261,321 B1 | 7/2001 | Kellan |
| 6,280,449 B1 | 8/2001 | Blake |
| 6,299,641 B1 | 10/2001 | Woods |
| 6,302,912 B1 | 10/2001 | Bernau |
| 6,306,167 B1 | 10/2001 | Bernau et al. |
| 6,358,280 B1 | 3/2002 | Herrick |
| 6,387,126 B1 | 5/2002 | Cumming |
| 6,398,809 B1 | 6/2002 | Hoffmann et al. |
| 6,406,494 B1 | 6/2002 | Laguette et al. |
| 6,413,262 B2 | 7/2002 | Saishin et al. |
| 6,413,277 B1 | 7/2002 | Neuhann |
| 6,423,094 B1 | 7/2002 | Sarfarazi |
| 6,425,917 B1 | 7/2002 | Blake |
| 6,428,574 B1 | 8/2002 | Valunin et al. |
| 6,432,246 B1 | 8/2002 | Blake |
| 6,443,984 B1 | 9/2002 | Jahn et al. |
| 6,443,985 B1 | 9/2002 | Woods |
| 6,451,056 B1 | 9/2002 | Cumming |
| 6,461,384 B1 | 10/2002 | Hoffmann et al. |
| 6,464,725 B2 | 10/2002 | Skotton |
| 6,475,240 B1 | 11/2002 | Paul |
| 6,482,229 B1 | 11/2002 | Gwon et al. |
| 6,488,707 B1 | 12/2002 | Callahan et al. |
| 6,488,708 B2 | 12/2002 | Sarfarazi |
| 6,488,709 B1 | 12/2002 | Barrett |
| 6,494,911 B2 | 12/2002 | Cumming |
| 6,503,276 B2 | 1/2003 | Lang et al. |
| 6,517,577 B1 | 2/2003 | Callahan et al. |
| 6,524,340 B2 | 2/2003 | Israel |
| 6,537,317 B1 | 3/2003 | Steinert et al. |
| 6,543,453 B1 | 4/2003 | Klima et al. |
| 6,547,822 B1 | 4/2003 | Lang |
| 6,554,859 B1 | 4/2003 | Lang et al. |
| 6,558,395 B2 | 5/2003 | Hjertman et al. |
| 6,558,420 B2 | 5/2003 | Green |
| 6,576,012 B2 | 6/2003 | Lang |
| 6,592,621 B1 | 7/2003 | Domino |
| 6,596,025 B2 | 7/2003 | Portney |
| 6,605,093 B1 | 8/2003 | Blake |
| 6,616,692 B1 | 9/2003 | Glick et al. |
| 6,638,306 B2 | 10/2003 | Cumming |
| 6,660,035 B1 | 12/2003 | Lang et al. |
| 6,666,887 B1 | 12/2003 | Callahan et al. |
| 6,695,881 B2 | 2/2004 | Peng et al. |
| 6,730,123 B1 | 5/2004 | Klopotek |
| 6,749,634 B2 | 6/2004 | Hanna |

(56) References Cited

U.S. PATENT DOCUMENTS

| | | |
|---|---|---|
| 6,755,859 B2 | 6/2004 | Hoffmann et al. |
| 6,761,737 B2 | 7/2004 | Zadno-Azizi et al. |
| 6,764,511 B2 | 7/2004 | Zadno-Azizi et al. |
| 6,767,363 B1 | 7/2004 | Bandhauer et al. |
| 6,786,928 B2 | 9/2004 | Callahan et al. |
| 6,786,934 B2 | 9/2004 | Zadno-Azizi et al. |
| 6,790,232 B1 | 9/2004 | Lang |
| 6,797,003 B1 | 9/2004 | Blake et al. |
| 6,800,091 B2 | 10/2004 | Callahan et al. |
| 6,824,563 B2 | 11/2004 | Lang |
| 6,836,374 B2 | 12/2004 | Esch et al. |
| 6,846,326 B2 | 1/2005 | Zadno-Azizi et al. |
| 6,849,091 B1 | 2/2005 | Cumming |
| 6,855,164 B2 | 2/2005 | Glazier |
| 6,858,040 B2 | 2/2005 | Nguyen et al. |
| 6,860,601 B2 | 3/2005 | Shadduck |
| 6,884,261 B2 | 4/2005 | Zadno-Azizi et al. |
| 6,899,732 B2 | 5/2005 | Zadno-Azizi et al. |
| 6,918,930 B2 | 7/2005 | Portney |
| 6,921,415 B2 | 7/2005 | Callahan et al. |
| 6,921,416 B2 | 7/2005 | Khoury |
| 6,926,736 B2 | 8/2005 | Peng et al. |
| 6,926,744 B1 | 8/2005 | Bos et al. |
| 6,932,839 B1 | 8/2005 | Kamerling et al. |
| 6,935,743 B2 | 8/2005 | Shadduck |
| 6,966,649 B2 | 11/2005 | Shadduck |
| 6,969,403 B2 | 11/2005 | Peng et al. |
| 6,986,763 B2 | 1/2006 | Holmen |
| 6,986,787 B1 | 1/2006 | Baker, Jr. |
| 6,991,651 B2 | 1/2006 | Portney |
| 7,025,783 B2 | 4/2006 | Brady et al. |
| 7,036,931 B2 | 5/2006 | Lindacher et al. |
| 7,037,338 B2 | 5/2006 | Nagamoto |
| 7,041,134 B2 | 5/2006 | Nguyen et al. |
| 7,048,759 B2 | 5/2006 | Bogaert et al. |
| 7,048,760 B2 | 5/2006 | Cumming |
| 7,060,094 B2 | 6/2006 | Shahinpoor et al. |
| 7,063,723 B2 | 6/2006 | Ran |
| 7,068,439 B2 | 6/2006 | Esch et al. |
| 7,087,080 B2 | 8/2006 | Zadno-Azizi et al. |
| 7,097,660 B2 | 8/2006 | Portney |
| 7,118,596 B2 | 10/2006 | Zadno-Azizi et al. |
| 7,118,597 B2 | 10/2006 | Miller et al. |
| 7,122,053 B2 | 10/2006 | Esch |
| 7,125,422 B2 | 10/2006 | Woods et al. |
| 7,137,702 B2 | 11/2006 | Piers et al. |
| 7,150,759 B2 | 12/2006 | Paul et al. |
| 7,150,760 B2 | 12/2006 | Zhang |
| 7,192,444 B2 | 3/2007 | Blake et al. |
| 7,198,640 B2 | 4/2007 | Nguyen |
| 7,204,849 B2 | 4/2007 | Portney |
| 7,217,288 B2 | 5/2007 | Esch et al. |
| 7,220,279 B2 | 5/2007 | Nun |
| 7,226,478 B2 | 6/2007 | Ting et al. |
| 7,229,475 B2 | 6/2007 | Glazier |
| 7,238,201 B2 | 7/2007 | Portney et al. |
| 7,247,168 B2 | 7/2007 | Esch et al. |
| 7,261,737 B2 | 8/2007 | Esch et al. |
| 7,264,351 B2 | 9/2007 | Shadduck |
| 7,278,739 B2 | 10/2007 | Shadduck |
| 7,354,451 B2 | 4/2008 | Koch |
| 7,377,640 B2 | 5/2008 | Piers et al. |
| 7,381,221 B2 | 6/2008 | Lang et al. |
| 7,384,429 B2 | 6/2008 | Hanna |
| 7,404,637 B2 | 7/2008 | Miller et al. |
| 7,404,638 B2 | 7/2008 | Miller et al. |
| 7,435,259 B2 | 10/2008 | Cumming |
| 7,438,723 B2 | 10/2008 | Esch |
| 7,452,362 B2 | 11/2008 | Zadno-Azizi et al. |
| 7,452,378 B2 | 11/2008 | Zadno-Azizi et al. |
| 7,455,691 B2 | 11/2008 | Feingold et al. |
| 7,462,193 B2 | 12/2008 | Nagamoto |
| 7,485,144 B2 | 2/2009 | Esch |
| 7,494,505 B2 | 2/2009 | Kappelhof et al. |
| 7,503,938 B2 | 3/2009 | Phillips |
| 7,553,327 B2 | 6/2009 | Cumming |
| 7,569,073 B2 | 8/2009 | Vaudant et al. |
| 7,591,849 B2 | 9/2009 | Richardson |
| 7,601,169 B2 | 10/2009 | Phillips |
| 7,615,056 B2 | 11/2009 | Ayton et al. |
| 7,615,073 B2 | 11/2009 | Deacon et al. |
| 7,621,949 B2 | 11/2009 | Deacon et al. |
| 7,637,947 B2 | 12/2009 | Smith et al. |
| 7,662,179 B2 | 2/2010 | Sarfarazi |
| 7,670,371 B2 | 3/2010 | Piers et al. |
| 7,674,288 B2 | 3/2010 | Nagamoto |
| 7,713,299 B2 | 5/2010 | Brady et al. |
| 7,722,670 B2 | 5/2010 | Elahi et al. |
| 7,744,646 B2 | 6/2010 | Zadno-Azizi et al. |
| 7,744,647 B2 | 6/2010 | Barrett |
| 7,763,069 B2 | 7/2010 | Brady et al. |
| 7,763,070 B2 | 7/2010 | Cumming |
| 7,771,471 B2 | 8/2010 | Dell |
| 7,776,088 B2 | 8/2010 | Shadduck |
| 7,780,729 B2 | 8/2010 | Nguyen et al. |
| 7,790,824 B2 | 9/2010 | Freeman |
| 7,790,825 B2 | 9/2010 | Lehman et al. |
| 7,794,497 B2 | 9/2010 | Brady et al. |
| 7,794,498 B2 | 9/2010 | Pinchuk |
| 7,806,930 B2 | 10/2010 | Brown |
| 7,811,320 B2 | 10/2010 | Werblin |
| 7,815,678 B2 | 10/2010 | Ben Nun |
| 7,837,730 B2 | 11/2010 | Cumming et al. |
| 7,842,087 B2 | 11/2010 | Ben Nun |
| 7,854,764 B2 | 12/2010 | Ben Nun |
| 7,857,850 B2 | 12/2010 | Mentak et al. |
| 7,871,437 B2 | 1/2011 | Hermans et al. |
| 7,878,655 B2 | 2/2011 | Salvati et al. |
| 7,883,540 B2 | 2/2011 | Niwa et al. |
| 7,905,917 B2 | 3/2011 | Altmann |
| 7,931,686 B2 | 4/2011 | Vaudant et al. |
| 7,942,889 B2 | 5/2011 | Assia |
| 7,981,155 B2 | 7/2011 | Cumming |
| 7,985,253 B2 | 7/2011 | Cumming |
| 7,998,198 B2 | 8/2011 | Angelopoulos et al. |
| 7,998,199 B2 | 8/2011 | Ben Nun |
| 8,012,204 B2 | 9/2011 | Weinschenk, III et al. |
| 8,034,106 B2 | 10/2011 | Mentak et al. |
| 8,034,107 B2 | 10/2011 | Stenger |
| 8,034,108 B2 | 10/2011 | Bumbalough |
| 8,038,711 B2 | 10/2011 | Clarke |
| 8,043,370 B2 | 10/2011 | Bretthauer et al. |
| 8,043,372 B2 | 10/2011 | Bumbalough |
| 8,048,155 B2 | 11/2011 | Shadduck |
| 8,048,156 B2 | 11/2011 | Geraghty et al. |
| 8,052,752 B2 | 11/2011 | Woods et al. |
| 8,062,361 B2 | 11/2011 | Nguyen et al. |
| 8,062,362 B2 | 11/2011 | Brady et al. |
| 8,066,768 B2 | 11/2011 | Werblin |
| 8,066,769 B2 | 11/2011 | Werblin |
| 8,070,806 B2 | 12/2011 | Khoury |
| 8,080,017 B2 | 12/2011 | Tanaka |
| 8,100,965 B2 | 1/2012 | Cumming et al. |
| 8,109,998 B2 | 2/2012 | Cumming |
| 8,123,729 B2 | 2/2012 | Yamamoto et al. |
| 8,133,273 B2 | 3/2012 | Aharoni et al. |
| 8,158,712 B2 | 4/2012 | Your |
| 8,163,015 B2 | 4/2012 | Cumming |
| 8,167,941 B2 | 5/2012 | Boyd et al. |
| 8,182,531 B2 | 5/2012 | Hermans et al. |
| 8,187,325 B2 | 5/2012 | Zadno-Azizi et al. |
| 8,206,442 B2 | 6/2012 | Sel et al. |
| 8,215,770 B2 | 7/2012 | Blum et al. |
| 8,216,305 B2 | 7/2012 | Salvati et al. |
| 8,216,306 B2 | 7/2012 | Coroneo |
| 8,216,308 B2 | 7/2012 | Blake et al. |
| 8,231,672 B2 | 7/2012 | Deacon et al. |
| 8,235,525 B2 | 8/2012 | Lesage et al. |
| 8,241,353 B2 | 8/2012 | Deacon et al. |
| 8,241,355 B2 | 8/2012 | Brady et al. |
| 8,246,679 B2 | 8/2012 | Nguyen et al. |
| 8,267,996 B2 | 9/2012 | Niwa et al. |
| 8,273,123 B2 | 9/2012 | Ben Nun |
| 8,303,656 B2 | 11/2012 | Shadduck |

(56) References Cited

U.S. PATENT DOCUMENTS

| | | |
|---|---|---|
| 8,314,927 B2 | 11/2012 | Choi et al. |
| 8,328,869 B2 | 12/2012 | Smiley et al. |
| 8,343,216 B2 | 1/2013 | Brady et al. |
| 8,343,217 B2 | 1/2013 | Bumbalough |
| 8,349,006 B2 | 1/2013 | Zhao et al. |
| 8,357,196 B2 | 1/2013 | Jain et al. |
| 8,361,145 B2 | 1/2013 | Scholl et al. |
| 8,366,653 B2 | 2/2013 | Shareef et al. |
| 8,377,123 B2 | 2/2013 | Evans et al. |
| 8,377,125 B2 | 2/2013 | Kellan |
| 8,382,831 B2 | 2/2013 | Ben Nun |
| 8,382,832 B2 | 2/2013 | Deacon et al. |
| 8,398,709 B2 | 3/2013 | Ben Nun |
| 8,403,984 B2 | 3/2013 | Tsai et al. |
| 8,414,646 B2 | 4/2013 | De Juan, Jr. et al. |
| 8,425,595 B2 | 4/2013 | Tsai et al. |
| 8,425,597 B2 | 4/2013 | Glick et al. |
| 8,425,598 B2 | 4/2013 | Klink et al. |
| 8,425,599 B2 | 4/2013 | Shadduck |
| 8,430,928 B2 | 4/2013 | Liao |
| 8,435,289 B2 | 5/2013 | Cole et al. |
| 8,447,086 B2 | 5/2013 | Hildebrand et al. |
| 8,449,611 B2 | 5/2013 | Richardson |
| 8,454,688 B2 | 6/2013 | Esch et al. |
| 8,465,544 B2 | 6/2013 | Brady et al. |
| 8,475,527 B2 | 7/2013 | Peterson et al. |
| 8,475,529 B2 | 7/2013 | Clarke |
| 8,480,734 B2 | 7/2013 | Kellan et al. |
| 8,486,140 B2 | 7/2013 | Willis et al. |
| 8,486,141 B2 | 7/2013 | Lang et al. |
| 8,486,142 B2 | 7/2013 | Bumbalough et al. |
| 8,496,701 B2 | 7/2013 | Hermans et al. |
| 8,500,804 B2 | 8/2013 | Brady et al. |
| 8,500,806 B1 | 8/2013 | Phillips |
| 8,523,942 B2 | 9/2013 | Cumming |
| 8,529,623 B2 | 9/2013 | Piers et al. |
| 8,535,376 B2 | 9/2013 | Altmann |
| 8,545,556 B2 | 10/2013 | Woods et al. |
| 8,551,164 B2 | 10/2013 | Willis et al. |
| 8,551,167 B2 | 10/2013 | Cuevas |
| 8,556,967 B2 | 10/2013 | Sarfarazi |
| 8,562,674 B2 | 10/2013 | Cole et al. |
| 8,568,478 B2 | 10/2013 | Zickler et al. |
| 8,574,293 B2 | 11/2013 | Kappelhof et al. |
| 8,579,971 B2 | 11/2013 | Webb |
| 8,579,972 B2 | 11/2013 | Rombach |
| 8,585,758 B2 | 11/2013 | Woods |
| 8,585,759 B2 | 11/2013 | Bumbalough |
| 8,608,799 B2 | 12/2013 | Blake |
| 8,608,800 B2 | 12/2013 | Portney |
| 8,613,766 B2 | 12/2013 | Richardson et al. |
| 8,623,082 B2 | 1/2014 | Kappelhof et al. |
| 8,647,384 B2 | 2/2014 | Lu |
| 8,652,206 B2 | 2/2014 | Masket |
| 8,657,877 B2 | 2/2014 | Glazier |
| 8,657,878 B2 | 2/2014 | Mentak et al. |
| 8,668,734 B2 | 3/2014 | Hildebrand et al. |
| 8,900,298 B2 | 12/2014 | Anvar et al. |
| 8,956,408 B2 | 2/2015 | Smiley et al. |
| 8,968,396 B2 | 3/2015 | Matthews et al. |
| 8,992,609 B2 | 3/2015 | Shadduck |
| 9,044,317 B2 | 6/2015 | Hildebrand et al. |
| 9,072,600 B2 | 7/2015 | Tran |
| 9,186,244 B2 | 11/2015 | Silvestrini et al. |
| 9,220,590 B2 | 12/2015 | Beer |
| 9,277,987 B2 | 3/2016 | Smiley et al. |
| 9,364,318 B2 | 6/2016 | Beer |
| 9,456,895 B2 | 10/2016 | Shadduck |
| 9,610,155 B2 | 4/2017 | Matthews |
| 9,693,858 B2 | 7/2017 | Hildebrand et al. |
| 9,795,473 B2 | 10/2017 | Smiley et al. |
| 9,855,137 B2 | 1/2018 | Smiley et al. |
| 9,855,139 B2 | 1/2018 | Matthews et al. |
| 9,872,762 B2 | 1/2018 | Scholl et al. |
| 9,872,763 B2 | 1/2018 | Smiley et al. |
| 10,004,596 B2 | 6/2018 | Brady et al. |
| 10,045,844 B2 | 8/2018 | Smiley et al. |
| 10,111,745 B2 | 10/2018 | Silvestrini et al. |
| 10,159,564 B2 | 12/2018 | Brady et al. |
| 10,195,020 B2 | 2/2019 | Matthews |
| 2001/0001836 A1* | 5/2001 | Cumming ............ A61F 2/1629 623/6.37 |
| 2001/0012964 A1 | 8/2001 | Lang et al. |
| 2001/0016771 A1 | 8/2001 | Cumming |
| 2001/0044657 A1 | 11/2001 | Kellan |
| 2001/0051826 A1 | 12/2001 | Bogaert et al. |
| 2002/0002404 A1 | 1/2002 | Sarfarazi |
| 2002/0013622 A1 | 1/2002 | Hennig |
| 2002/0016630 A1 | 2/2002 | Lang |
| 2002/0045937 A1 | 4/2002 | Sarfarazi |
| 2002/0051063 A1 | 5/2002 | Hwang |
| 2002/0072673 A1 | 6/2002 | Yamamoto et al. |
| 2002/0072795 A1 | 6/2002 | Green |
| 2002/0101564 A1 | 8/2002 | Herrick |
| 2002/0103535 A1 | 8/2002 | Portney |
| 2002/0107568 A1 | 8/2002 | Zadno-Azizi et al. |
| 2002/0111678 A1 | 8/2002 | Zadno-Azizi et al. |
| 2002/0116057 A1 | 8/2002 | Ting et al. |
| 2002/0116058 A1 | 8/2002 | Zadno-Azizi et al. |
| 2002/0116059 A1 | 8/2002 | Zadno-Azizi et al. |
| 2002/0116060 A1 | 8/2002 | Nguyen et al. |
| 2002/0116061 A1 | 8/2002 | Zadno-Azizi et al. |
| 2002/0116062 A1 | 8/2002 | Portney |
| 2002/0133228 A1 | 9/2002 | Sarver |
| 2002/0138140 A1 | 9/2002 | Hanna |
| 2002/0138141 A1 | 9/2002 | Zadno-Azizi et al. |
| 2002/0143395 A1 | 10/2002 | Skottun |
| 2002/0161435 A1 | 10/2002 | Portney |
| 2002/0173847 A1 | 11/2002 | Pham et al. |
| 2002/0177896 A1 | 11/2002 | Israel |
| 2002/0183843 A1 | 12/2002 | Blake et al. |
| 2002/0193876 A1 | 12/2002 | Lang et al. |
| 2002/0193877 A1 | 12/2002 | Hoffmann et al. |
| 2003/0018386 A1 | 1/2003 | Laguette et al. |
| 2003/0033011 A1 | 2/2003 | Singer et al. |
| 2003/0033013 A1* | 2/2003 | Callahan ............ A61F 2/1613 623/6.21 |
| 2003/0060878 A1 | 3/2003 | Shadduck |
| 2003/0065387 A1 | 4/2003 | Callahan et al. |
| 2003/0074060 A1 | 4/2003 | Zadno-Azizi et al. |
| 2003/0074061 A1 | 4/2003 | Pham et al. |
| 2003/0078655 A1 | 4/2003 | Callahan et al. |
| 2003/0078656 A1 | 4/2003 | Nguyen |
| 2003/0078657 A1 | 4/2003 | Zadno-Azizi et al. |
| 2003/0078658 A1 | 4/2003 | Zadno-Azizi |
| 2003/0083744 A1 | 5/2003 | Khoury |
| 2003/0093149 A1 | 5/2003 | Glazier |
| 2003/0105522 A1 | 6/2003 | Glazier |
| 2003/0109926 A1 | 6/2003 | Portney |
| 2003/0114927 A1 | 6/2003 | Nagamoto |
| 2003/0130732 A1 | 7/2003 | Sarfarazi |
| 2003/0135271 A1 | 7/2003 | Bandhauer |
| 2003/0135273 A1 | 7/2003 | Callahan et al. |
| 2003/0147046 A1 | 8/2003 | Shadduck |
| 2003/0149480 A1 | 8/2003 | Shadduck |
| 2003/0171808 A1 | 9/2003 | Phillips |
| 2003/0171809 A1* | 9/2003 | Phillips ............... A61F 2/1629 623/6.45 |
| 2003/0181977 A1 | 9/2003 | Brady |
| 2003/0187504 A1 | 10/2003 | Weinschenk et al. |
| 2003/0199976 A1 | 10/2003 | Portney |
| 2003/0204254 A1 | 10/2003 | Peng et al. |
| 2003/0204255 A1 | 10/2003 | Peng et al. |
| 2003/0204256 A1 | 10/2003 | Peng et al. |
| 2004/0015236 A1 | 1/2004 | Sarfarazi |
| 2004/0034417 A1 | 2/2004 | Heyman |
| 2004/0064182 A1 | 4/2004 | Kelman |
| 2004/0073304 A1 | 4/2004 | Weinschenk et al. |
| 2004/0082993 A1 | 4/2004 | Woods |
| 2004/0082994 A1 | 4/2004 | Woods et al. |
| 2004/0082995 A1 | 4/2004 | Woods |
| 2004/0100704 A1 | 5/2004 | Shadduck |
| 2004/0106992 A1 | 6/2004 | Lang et al. |
| 2004/0106993 A1 | 6/2004 | Portney |

(56) References Cited

U.S. PATENT DOCUMENTS

| | | |
|---|---|---|
| 2004/0111152 A1 | 6/2004 | Kelman |
| 2004/0111153 A1 | 6/2004 | Woods et al. |
| 2004/0117013 A1* | 6/2004 | Schachar ............... A61F 2/1602 623/6.36 |
| 2004/0158322 A1 | 8/2004 | Shen |
| 2004/0162612 A1* | 8/2004 | Portney ................ A61F 2/1613 623/6.34 |
| 2004/0169816 A1 | 9/2004 | Esch |
| 2004/0169932 A1 | 9/2004 | Esch et al. |
| 2004/0181279 A1 | 9/2004 | Nun |
| 2004/0184158 A1 | 9/2004 | Shadduck |
| 2004/0190153 A1 | 9/2004 | Esch |
| 2004/0215340 A1 | 10/2004 | Messner et al. |
| 2004/0230300 A1 | 11/2004 | Bandhauer et al. |
| 2004/0236422 A1 | 11/2004 | Zhang et al. |
| 2004/0236423 A1 | 11/2004 | Zhang et al. |
| 2004/0243233 A1 | 12/2004 | Phillips |
| 2004/0249455 A1 | 12/2004 | Tran |
| 2005/0021137 A1 | 1/2005 | Blake et al. |
| 2005/0021138 A1 | 1/2005 | Woods |
| 2005/0021139 A1 | 1/2005 | Shadduck |
| 2005/0049700 A1 | 3/2005 | Zadno-Azizi et al. |
| 2005/0055092 A1 | 3/2005 | Nguyen et al. |
| 2005/0060032 A1 | 3/2005 | Magnante et al. |
| 2005/0071002 A1 | 3/2005 | Glazier |
| 2005/0075732 A1 | 4/2005 | Israel |
| 2005/0085907 A1 | 4/2005 | Hanna |
| 2005/0090896 A1 | 4/2005 | Ben Nun |
| 2005/0096498 A1* | 5/2005 | Houser ............... A61B 17/0057 600/37 |
| 2005/0096741 A1 | 5/2005 | Cumming |
| 2005/0107873 A1 | 5/2005 | Zhou |
| 2005/0107875 A1 | 5/2005 | Cumming |
| 2005/0113914 A1 | 5/2005 | Miller et al. |
| 2005/0119739 A1 | 6/2005 | Glazier |
| 2005/0119740 A1 | 6/2005 | Esch et al. |
| 2005/0125055 A1 | 6/2005 | Deacon et al. |
| 2005/0125056 A1 | 6/2005 | Deacon et al. |
| 2005/0125057 A1 | 6/2005 | Cumming |
| 2005/0125059 A1 | 6/2005 | Pinchuk et al. |
| 2005/0131535 A1 | 6/2005 | Woods |
| 2005/0137703 A1 | 6/2005 | Chen |
| 2005/0143814 A1 | 6/2005 | Esch et al. |
| 2005/0149183 A1 | 7/2005 | Shadduck |
| 2005/0149184 A1 | 7/2005 | Bogaert |
| 2005/0209692 A1 | 9/2005 | Zhang |
| 2005/0234547 A1 | 10/2005 | Nguyen et al. |
| 2005/0251254 A1 | 11/2005 | Brady et al. |
| 2005/0267575 A1 | 12/2005 | Nguyen et al. |
| 2006/0020339 A1 | 1/2006 | Ran |
| 2006/0030938 A1 | 2/2006 | Altmann |
| 2006/0041307 A1 | 2/2006 | Esch et al. |
| 2006/0047339 A1 | 3/2006 | Brown |
| 2006/0047340 A1 | 3/2006 | Brown |
| 2006/0061729 A1 | 3/2006 | Shadduck |
| 2006/0064162 A1 | 3/2006 | Klima |
| 2006/0069433 A1 | 3/2006 | Nun |
| 2006/0087614 A1 | 4/2006 | Shadduck |
| 2006/0089712 A1 | 4/2006 | Malecaze |
| 2006/0092340 A1 | 5/2006 | Blum et al. |
| 2006/0100701 A1 | 5/2006 | Esch et al. |
| 2006/0100703 A1 | 5/2006 | Evans et al. |
| 2006/0100704 A1 | 5/2006 | Blake et al. |
| 2006/0116765 A1 | 6/2006 | Blake et al. |
| 2006/0142855 A1 | 6/2006 | Vaudant et al. |
| 2006/0149369 A1 | 7/2006 | Cumming et al. |
| 2006/0178741 A1 | 8/2006 | Zadno-Azizi et al. |
| 2006/0178742 A1 | 8/2006 | Nagamoto |
| 2006/0184244 A1 | 8/2006 | Nguyen et al. |
| 2006/0212116 A1 | 9/2006 | Woods |
| 2006/0212117 A1 | 9/2006 | Lang et al. |
| 2006/0247766 A1 | 11/2006 | Marin |
| 2006/0247767 A1 | 11/2006 | Koch |
| 2006/0253196 A1 | 11/2006 | Woods |
| 2006/0259139 A1 | 11/2006 | Zadno-Azizi et al. |
| 2006/0259140 A1 | 11/2006 | Dell |
| 2006/0271186 A1 | 11/2006 | Nishi et al. |
| 2006/0271187 A1 | 11/2006 | Zadno-Azizi et al. |
| 2007/0005135 A1 | 1/2007 | Makker et al. |
| 2007/0005136 A1 | 1/2007 | Richardson |
| 2007/0010880 A1 | 1/2007 | Esch |
| 2007/0010882 A1 | 1/2007 | Barrett |
| 2007/0016293 A1 | 1/2007 | Tran |
| 2007/0021831 A1 | 1/2007 | Clarke |
| 2007/0021832 A1 | 1/2007 | Nordan |
| 2007/0027540 A1 | 2/2007 | Zadno-Azizi et al. |
| 2007/0032866 A1 | 2/2007 | Portney |
| 2007/0050024 A1 | 3/2007 | Zhang |
| 2007/0050025 A1 | 3/2007 | Nguyen et al. |
| 2007/0067030 A1 | 3/2007 | Glazier et al. |
| 2007/0078515 A1* | 4/2007 | Brady ................ A61F 2/1613 623/6.37 |
| 2007/0083260 A1 | 4/2007 | Colvard |
| 2007/0083261 A1 | 4/2007 | Colvard |
| 2007/0088433 A1 | 4/2007 | Esch et al. |
| 2007/0100444 A1 | 5/2007 | Brady et al. |
| 2007/0100445 A1 | 5/2007 | Shadduck |
| 2007/0106377 A1 | 5/2007 | Smith et al. |
| 2007/0106380 A1 | 5/2007 | Terwee et al. |
| 2007/0106381 A1 | 5/2007 | Blake |
| 2007/0108643 A1 | 5/2007 | Zadno-Azizi et al. |
| 2007/0118216 A1 | 5/2007 | Pynson |
| 2007/0123981 A1 | 5/2007 | Tassignon |
| 2007/0129798 A1 | 6/2007 | Chawdhary |
| 2007/0129803 A1 | 6/2007 | Cumming et al. |
| 2007/0135915 A1 | 6/2007 | Klima |
| 2007/0142913 A1 | 6/2007 | Phillips |
| 2007/0156236 A1 | 7/2007 | Stenger |
| 2007/0171366 A1 | 7/2007 | Su et al. |
| 2007/0185574 A1 | 8/2007 | Ben Nun |
| 2007/0203578 A1 | 8/2007 | Scholl et al. |
| 2007/0213817 A1 | 9/2007 | Esch et al. |
| 2007/0239274 A1 | 10/2007 | Kellan |
| 2007/0244560 A1 | 10/2007 | Ossipov et al. |
| 2007/0244561 A1 | 10/2007 | Ben Nun |
| 2007/0260308 A1 | 11/2007 | Tran |
| 2007/0260309 A1 | 11/2007 | Richardson |
| 2007/0260310 A1 | 11/2007 | Richardson |
| 2007/0270946 A1 | 11/2007 | Poley |
| 2007/0299487 A1 | 12/2007 | Shadduck |
| 2008/0004699 A1 | 1/2008 | Ben Nun |
| 2008/0015689 A1 | 1/2008 | Esch et al. |
| 2008/0021549 A1 | 1/2008 | Eagan et al. |
| 2008/0021550 A1 | 1/2008 | Richardson |
| 2008/0033449 A1* | 2/2008 | Cole ................ A61F 2/1691 606/107 |
| 2008/0046074 A1 | 2/2008 | Smith et al. |
| 2008/0046075 A1 | 2/2008 | Esch et al. |
| 2008/0046076 A1 | 2/2008 | Rombach |
| 2008/0051801 A1 | 2/2008 | Hovey et al. |
| 2008/0077238 A1 | 3/2008 | Deacon et al. |
| 2008/0077239 A1 | 3/2008 | Zickler et al. |
| 2008/0086206 A1 | 4/2008 | Nasiatka et al. |
| 2008/0086208 A1 | 4/2008 | Nordan |
| 2008/0109077 A1 | 5/2008 | Bos |
| 2008/0109078 A1 | 5/2008 | Rozakis et al. |
| 2008/0154364 A1 | 6/2008 | Richardson et al. |
| 2008/0161913 A1 | 7/2008 | Brady et al. |
| 2008/0161914 A1 | 7/2008 | Brady et al. |
| 2008/0183289 A1 | 7/2008 | Werblin |
| 2008/0188930 A1 | 8/2008 | Mentak et al. |
| 2008/0200982 A1 | 8/2008 | Your |
| 2008/0208335 A1 | 8/2008 | Blum et al. |
| 2008/0215147 A1 | 9/2008 | Werblin |
| 2008/0243247 A1 | 10/2008 | Poley et al. |
| 2008/0269642 A1 | 10/2008 | Deacon et al. |
| 2008/0269882 A1 | 10/2008 | Simpson et al. |
| 2008/0269885 A1 | 10/2008 | Simpson et al. |
| 2008/0269886 A1 | 10/2008 | Simpson et al. |
| 2008/0281417 A1 | 11/2008 | Nagamoto |
| 2008/0300680 A1 | 12/2008 | Joshua |
| 2008/0306587 A1 | 12/2008 | Your |
| 2008/0306588 A1 | 12/2008 | Smiley et al. |
| 2009/0005865 A1 | 1/2009 | Smiley et al. |

(56) References Cited

U.S. PATENT DOCUMENTS

| | | |
|---|---|---|
| 2009/0005866 A1 | 1/2009 | Cumming |
| 2009/0012609 A1 | 1/2009 | Geraghty et al. |
| 2009/0018652 A1 | 1/2009 | Hermans et al. |
| 2009/0027661 A1 | 1/2009 | Choi et al. |
| 2009/0030425 A1 | 1/2009 | Smiley et al. |
| 2009/0033863 A1 | 2/2009 | Blum et al. |
| 2009/0036982 A1 | 2/2009 | Aharoni et al. |
| 2009/0062912 A1 | 3/2009 | Rombach |
| 2009/0124773 A1 | 5/2009 | Zhou et al. |
| 2009/0125105 A1 | 5/2009 | Lesage et al. |
| 2009/0125106 A1 | 5/2009 | Weinschenk, III et al. |
| 2009/0149952 A1 | 6/2009 | Shadduck |
| 2009/0171458 A1 | 7/2009 | Kellan et al. |
| 2009/0187242 A1 | 7/2009 | Weeber et al. |
| 2009/0198326 A1 | 8/2009 | Zhou et al. |
| 2009/0204209 A1 | 8/2009 | Tran |
| 2009/0204210 A1 | 8/2009 | Pynson |
| 2009/0204211 A1 | 8/2009 | Angelopoulos et al. |
| 2009/0210054 A1 | 8/2009 | Weeber et al. |
| 2009/0228101 A1 | 9/2009 | Zadno-Azizi |
| 2009/0234448 A1 | 9/2009 | Weeber et al. |
| 2009/0234449 A1 | 9/2009 | De Juan, Jr. et al. |
| 2009/0248152 A1 | 10/2009 | Bumbalough |
| 2009/0248154 A1 | 10/2009 | Dell |
| 2009/0264998 A1 | 10/2009 | Mentak et al. |
| 2009/0264999 A1 | 10/2009 | Cumming |
| 2009/0265000 A1 | 10/2009 | Vaudant et al. |
| 2009/0292354 A1 | 11/2009 | Gontijo et al. |
| 2009/0292355 A1 | 11/2009 | Boyd et al. |
| 2009/0312836 A1 | 12/2009 | Pinchuk et al. |
| 2009/0319040 A1 | 12/2009 | Khoury |
| 2010/0016964 A1 | 1/2010 | Werblin |
| 2010/0036490 A1 | 2/2010 | Deacon et al. |
| 2010/0094412 A1 | 4/2010 | Wensrich |
| 2010/0094415 A1 | 4/2010 | Bumbalough |
| 2010/0121443 A1 | 5/2010 | Michel et al. |
| 2010/0121444 A1 | 5/2010 | Ben Nun |
| 2010/0131058 A1 | 5/2010 | Shadduck |
| 2010/0131059 A1 | 5/2010 | Callahan et al. |
| 2010/0131061 A1 | 5/2010 | Callahan et al. |
| 2010/0134754 A1 | 6/2010 | Hong et al. |
| 2010/0137983 A1 | 6/2010 | Culbertson et al. |
| 2010/0152848 A1 | 6/2010 | Williamson et al. |
| 2010/0179652 A1 | 7/2010 | Yamamoto et al. |
| 2010/0179653 A1 | 7/2010 | Argento et al. |
| 2010/0198349 A1 | 8/2010 | Brady et al. |
| 2010/0204788 A1 | 8/2010 | Van Noy |
| 2010/0211167 A1 | 8/2010 | Glazier |
| 2010/0211170 A1 | 8/2010 | Liao |
| 2010/0211171 A1 | 8/2010 | Sarfarazi |
| 2010/0228260 A1 | 9/2010 | Callahan et al. |
| 2010/0228344 A1 | 9/2010 | Shadduck |
| 2010/0228346 A1 | 9/2010 | Esch |
| 2010/0292789 A1 | 11/2010 | Willis et al. |
| 2010/0318186 A1 | 12/2010 | Bumbalough et al. |
| 2010/0324672 A1 | 12/2010 | Esch et al. |
| 2010/0324673 A1 | 12/2010 | Nguyen et al. |
| 2011/0029074 A1 | 2/2011 | Reisin et al. |
| 2011/0035001 A1 | 2/2011 | Woods |
| 2011/0035002 A1 | 2/2011 | Nun |
| 2011/0040376 A1 | 2/2011 | Christie et al. |
| 2011/0040378 A1 | 2/2011 | Werblin |
| 2011/0040379 A1 | 2/2011 | Bumbalough |
| 2011/0052020 A1 | 3/2011 | Hildebrand et al. |
| 2011/0054600 A1 | 3/2011 | Bumbalough |
| 2011/0054601 A1 | 3/2011 | Kadziauskas et al. |
| 2011/0071628 A1 | 3/2011 | Gross et al. |
| 2011/0082544 A1 | 4/2011 | Ben Nun |
| 2011/0093067 A1 | 4/2011 | Michalek et al. |
| 2011/0098810 A1 | 4/2011 | Altmann |
| 2011/0098812 A1 | 4/2011 | Ben Nun |
| 2011/0112635 A1 | 5/2011 | Ben Nun |
| 2011/0112636 A1 | 5/2011 | Ben Nun |
| 2011/0112638 A1 | 5/2011 | Hermans et al. |
| 2011/0118836 A1 | 5/2011 | Jain et al. |
| 2011/0153014 A1 | 6/2011 | Zhang et al. |
| 2011/0153015 A1 | 6/2011 | Simonov et al. |
| 2011/0160852 A1 | 6/2011 | Mentak et al. |
| 2011/0184514 A1 | 7/2011 | Angelopoulos et al. |
| 2011/0191086 A1 | 8/2011 | Callahan et al. |
| 2011/0208301 A1 | 8/2011 | Anvar et al. |
| 2011/0224788 A1 | 9/2011 | Webb |
| 2011/0238174 A1 | 9/2011 | Hong et al. |
| 2011/0245920 A1 | 10/2011 | Richardson |
| 2011/0251686 A1 | 10/2011 | Masket |
| 2011/0257742 A1 | 10/2011 | Bumbalough et al. |
| 2011/0270389 A1 | 11/2011 | Glazer et al. |
| 2011/0282441 A1 | 11/2011 | Zadno-Azizi |
| 2011/0282442 A1 | 11/2011 | Scholl et al. |
| 2011/0282443 A1 | 11/2011 | Smiley et al. |
| 2011/0288638 A1 | 11/2011 | Smiley et al. |
| 2011/0295368 A1 | 12/2011 | Betser |
| 2011/0304058 A1 | 12/2011 | Pendse |
| 2011/0307058 A1* | 12/2011 | Beer ............... A61F 2/1629 623/6.43 |
| 2011/0313522 A1 | 12/2011 | Hayes |
| 2011/0313523 A1 | 12/2011 | Hayes |
| 2012/0010704 A1 | 1/2012 | Bumbalough |
| 2012/0016473 A1 | 1/2012 | Brady et al. |
| 2012/0022547 A1 | 1/2012 | Hildebrand et al. |
| 2012/0029632 A1 | 2/2012 | Ben Nun |
| 2012/0035724 A1 | 2/2012 | Clarke |
| 2012/0046743 A1 | 2/2012 | Pinchuk |
| 2012/0046744 A1 | 2/2012 | Woods et al. |
| 2012/0059465 A1 | 3/2012 | Brady et al. |
| 2012/0078361 A1 | 3/2012 | Shadduck |
| 2012/0078363 A1 | 3/2012 | Lu |
| 2012/0078364 A1 | 3/2012 | Stenger |
| 2012/0116506 A1 | 5/2012 | Compertore |
| 2012/0130487 A1 | 5/2012 | Doraiswamy et al. |
| 2012/0130488 A1 | 5/2012 | Doraiswamy et al. |
| 2012/0143327 A1 | 6/2012 | Bumbalough |
| 2012/0150292 A1 | 6/2012 | Mentak et al. |
| 2012/0203338 A1 | 8/2012 | Jain |
| 2012/0232648 A1 | 9/2012 | Kahook et al. |
| 2012/0232650 A1 | 9/2012 | Hermans et al. |
| 2012/0232651 A1 | 9/2012 | Kahook et al. |
| 2012/0245591 A1 | 9/2012 | Matthews |
| 2012/0245684 A1 | 9/2012 | Liao |
| 2012/0253458 A1 | 10/2012 | Geraghty et al. |
| 2012/0253459 A1 | 10/2012 | Reich et al. |
| 2012/0290084 A1 | 11/2012 | Coroneo |
| 2012/0296425 A1 | 11/2012 | Cumming |
| 2012/0296426 A1 | 11/2012 | Brady et al. |
| 2012/0303119 A1 | 11/2012 | Callahan et al. |
| 2012/0310338 A1 | 12/2012 | Christie et al. |
| 2012/0310342 A1 | 12/2012 | Nguyen et al. |
| 2012/0310343 A1 | 12/2012 | Van Noy |
| 2012/0310344 A1 | 12/2012 | Cumming |
| 2012/0310345 A1 | 12/2012 | Olcina Portilla |
| 2012/0323320 A1 | 12/2012 | Simonov et al. |
| 2012/0323321 A1 | 12/2012 | Simonov et al. |
| 2012/0330415 A1 | 12/2012 | Callahan et al. |
| 2013/0013060 A1 | 1/2013 | Zadno-Azizi et al. |
| 2013/0018461 A1 | 1/2013 | Ben Nun |
| 2013/0030525 A1 | 1/2013 | Brady et al. |
| 2013/0035760 A1 | 2/2013 | Portney |
| 2013/0053954 A1 | 2/2013 | Rao et al. |
| 2013/0060330 A1 | 3/2013 | Weeber et al. |
| 2013/0060331 A1 | 3/2013 | Shadduck |
| 2013/0060332 A1 | 3/2013 | Simpson |
| 2013/0073039 A1 | 3/2013 | Mirlay |
| 2013/0103146 A1 | 4/2013 | Smiley et al. |
| 2013/0103147 A1 | 4/2013 | Christie et al. |
| 2013/0110235 A1 | 5/2013 | Schwiegerling |
| 2013/0116781 A1 | 5/2013 | Ben Nun |
| 2013/0131794 A1 | 5/2013 | Smiley et al. |
| 2013/0138208 A1 | 5/2013 | Simonov et al. |
| 2013/0150961 A1 | 6/2013 | Evans et al. |
| 2013/0166026 A1 | 6/2013 | Bumbalough |
| 2013/0184816 A1 | 7/2013 | Hayes |
| 2013/0190868 A1 | 7/2013 | Kahook et al. |
| 2013/0197635 A1 | 8/2013 | Phillips |
| 2013/0204364 A1 | 8/2013 | Olson |

(56) References Cited

U.S. PATENT DOCUMENTS

| | | |
|---|---|---|
| 2013/0204365 A1 | 8/2013 | Dell |
| 2013/0226294 A1 | 8/2013 | Van Der Mooren et al. |
| 2013/0226295 A1 | 8/2013 | de Juan, Jr. et al. |
| 2013/0231741 A1 | 9/2013 | Clarke |
| 2013/0231742 A1 | 9/2013 | Deacon et al. |
| 2013/0238091 A1 | 9/2013 | Danta et al. |
| 2013/0245754 A1 | 9/2013 | Blum et al. |
| 2013/0245756 A1 | 9/2013 | Liao |
| 2013/0268070 A1 | 10/2013 | Esch et al. |
| 2013/0268071 A1 | 10/2013 | Vilupuru et al. |
| 2013/0282117 A1 | 10/2013 | Van Heugten et al. |
| 2013/0297018 A1 | 11/2013 | Brady et al. |
| 2013/0304202 A1 | 11/2013 | Basinger |
| 2013/0304204 A1 | 11/2013 | Bumbalough et al. |
| 2013/0310931 A1 | 11/2013 | Kahook et al. |
| 2013/0310932 A1 | 11/2013 | Kellan |
| 2013/0317606 A1 | 11/2013 | Culbertson et al. |
| 2013/0317608 A1 | 11/2013 | Hermans et al. |
| 2013/0331937 A1 | 12/2013 | Stevens |
| 2013/0338767 A1 | 12/2013 | Mazzocchi et al. |
| 2013/0345713 A1 | 12/2013 | Cole et al. |
| 2014/0005780 A1 | 1/2014 | Zhao |
| 2014/0005781 A1 | 1/2014 | Zhao et al. |
| 2014/0005782 A1 | 1/2014 | Kellan et al. |
| 2014/0012277 A1 | 1/2014 | Matthews et al. |
| 2014/0052245 A1 | 2/2014 | Zickler et al. |
| 2014/0052246 A1 | 2/2014 | Kahook et al. |
| 2014/0058507 A1 | 2/2014 | Reich et al. |
| 2014/0142588 A1 | 5/2014 | Hildebrand et al. |
| 2014/0180403 A1 | 6/2014 | Silvestrini et al. |
| 2014/0180405 A1 | 6/2014 | Weinschenk, III et al. |
| 2014/0180406 A1 | 6/2014 | Simpson |
| 2014/0180407 A1 | 6/2014 | Sohn et al. |
| 2014/0194859 A1 | 7/2014 | Ianchulev |
| 2014/0249625 A1 | 9/2014 | Shadduck |
| 2015/0087743 A1 | 3/2015 | Anvar et al. |
| 2015/0088254 A1 | 3/2015 | Cumming |
| 2015/0105760 A1 | 4/2015 | Rao et al. |
| 2015/0134059 A1 | 5/2015 | Curatu |
| 2015/0142108 A1 | 5/2015 | Akura et al. |
| 2015/0202041 A1 | 7/2015 | Shadduck |
| 2015/0238310 A1 | 8/2015 | Matthews et al. |
| 2015/0257874 A1 | 9/2015 | Hildebrand et al. |
| 2016/0003016 A1 | 1/2016 | Brady et al. |
| 2016/0038278 A1 | 2/2016 | Matthews |
| 2016/0128826 A1 | 5/2016 | Silvestrini et al. |
| 2016/0157996 A1 | 6/2016 | Dolla et al. |
| 2016/0184091 A1 | 6/2016 | Smiley et al. |
| 2016/0184092 A1 | 6/2016 | Smiley et al. |
| 2016/0262875 A1 | 9/2016 | Smith et al. |
| 2016/0317286 A1 | 11/2016 | Brady et al. |
| 2016/0317287 A1 | 11/2016 | Silvestrini et al. |
| 2016/0361157 A1 | 12/2016 | Honigsbaum |
| 2017/0020662 A1 | 1/2017 | Shadduck |
| 2017/0049561 A1 | 2/2017 | Smiley et al. |
| 2017/0079773 A1 | 3/2017 | Matthews et al. |
| 2017/0247525 A1 | 8/2017 | Silvestrini et al. |
| 2017/0290658 A1 | 10/2017 | Hildebrand et al. |
| 2017/0342096 A1 | 11/2017 | Silvestrini |
| 2018/0028308 A1 | 2/2018 | Smiley et al. |
| 2018/0125640 A1 | 5/2018 | Smiley et al. |
| 2018/0147051 A1 | 5/2018 | Scholl et al. |
| 2018/0153682 A1 | 6/2018 | Hajela et al. |
| 2018/0177639 A1 | 6/2018 | Rao et al. |
| 2018/0256315 A1 | 9/2018 | Hildebrand et al. |
| 2018/0271645 A1 | 9/2018 | Brady et al. |
| 2018/0344453 A1 | 12/2018 | Brady et al. |
| 2019/0000612 A1 | 1/2019 | Rao et al. |
| 2019/0099263 A1 | 4/2019 | Brady et al. |

FOREIGN PATENT DOCUMENTS

| | | |
|---|---|---|
| AU | 2003300879 A1 | 7/2004 |
| AU | 2004211746 A1 | 8/2004 |
| AU | 2004219674 A1 | 9/2004 |
| AU | 2005299661 A1 | 5/2006 |
| AU | 2006265668 A1 | 1/2007 |
| AU | 2006304339 A1 | 4/2007 |
| AU | 2007340043 A1 | 7/2008 |
| AU | 2008218313 A1 | 8/2008 |
| AU | 2008279167 A1 | 1/2009 |
| AU | 2008279173 A1 | 1/2009 |
| AU | 2010235988 A1 | 11/2010 |
| AU | 2010203427 A1 | 7/2011 |
| AU | 2012335677 A1 | 5/2014 |
| AU | 2014202532 A1 | 7/2014 |
| AU | 2013235467 A1 | 9/2014 |
| AU | 2015258287 A1 | 12/2015 |
| AU | 2017216460 A1 | 8/2017 |
| AU | 2016275073 A1 | 1/2018 |
| AU | 2018200978 A1 | 3/2018 |
| AU | 2016349532 A1 | 4/2018 |
| AU | 2019201556 A1 | 3/2019 |
| CA | 2506753 A1 | 6/2004 |
| CA | 2508143 A1 | 6/2004 |
| CA | 2507694 A1 | 7/2004 |
| CA | 2515355 A1 | 8/2004 |
| CA | 2584472 A1 | 5/2006 |
| CA | 2613580 A1 | 1/2007 |
| CA | 2626269 A1 | 4/2007 |
| CA | 2674816 A1 | 7/2008 |
| CA | 2676713 A1 | 8/2008 |
| CA | 2693906 A1 | 1/2009 |
| CA | 2696450 A1 | 1/2009 |
| CA | 2748812 A1 | 7/2010 |
| CA | 2854919 A1 | 5/2013 |
| CA | 2865954 A1 | 9/2013 |
| CA | 2987311 A1 | 12/2016 |
| CA | 3001477 A1 | 5/2017 |
| DE | 112010004191 T5 | 11/2012 |
| EP | 1563337 A2 | 8/2005 |
| EP | 1569581 A1 | 9/2005 |
| EP | 1585563 A2 | 10/2005 |
| EP | 1590702 A2 | 11/2005 |
| EP | 1816984 A2 | 8/2007 |
| EP | 1906882 A2 | 4/2008 |
| EP | 1948084 A2 | 7/2008 |
| EP | 2053991 A2 | 5/2009 |
| EP | 2094193 A2 | 9/2009 |
| EP | 2112932 A2 | 11/2009 |
| EP | 2178462 A2 | 4/2010 |
| EP | 2178463 A2 | 4/2010 |
| EP | 2178464 A2 | 4/2010 |
| EP | 2221024 A1 | 8/2010 |
| EP | 2384167 A2 | 11/2011 |
| EP | 2473138 A2 | 7/2012 |
| EP | 2539351 A2 | 1/2013 |
| EP | 2559405 A2 | 2/2013 |
| EP | 2563275 A1 | 3/2013 |
| EP | 2647353 A1 | 10/2013 |
| EP | 2671541 A1 | 12/2013 |
| EP | 2688515 A2 | 1/2014 |
| EP | 2775961 A1 | 9/2014 |
| EP | 2827804 A1 | 1/2015 |
| EP | 2934383 A1 | 10/2015 |
| EP | 2967842 A1 | 1/2016 |
| EP | 3049023 A1 | 8/2016 |
| EP | 3062742 A1 | 9/2016 |
| EP | 3181094 A1 | 6/2017 |
| EP | 3197462 A1 | 8/2017 |
| EP | 3263574 A1 | 1/2018 |
| EP | 3307206 A1 | 4/2018 |
| EP | 3370647 A1 | 9/2018 |
| GB | 1583193 A | 1/1981 |
| HK | 1227277 A | 10/2017 |
| HK | 1227679 A | 10/2017 |
| HK | 1234303 A | 2/2018 |
| HK | 1235658 A | 3/2018 |
| HK | 1239501 A | 5/2018 |
| HK | 1241712 A | 6/2018 |
| HK | 1242207 A | 6/2018 |
| IN | 6305DELNP2015 A | 7/2016 |
| IN | 201617018083 A | 8/2016 |
| IN | 201717013927 A | 8/2017 |

(56) References Cited

FOREIGN PATENT DOCUMENTS

| | | | |
|---|---|---|---|
| IN | 201617044673 A | 2/2018 | |
| JP | 2014061387 A | 4/2014 | |
| NL | 2012420 A | 9/2014 | |
| WO | WO-0117461 A1 * | 3/2001 | ........... A61F 2/1613 |
| WO | WO-2001017461 A1 | 3/2001 | |
| WO | WO-2004046768 A2 | 6/2004 | |
| WO | WO-2004052242 A1 | 6/2004 | |
| WO | WO-2004054471 A2 | 7/2004 | |
| WO | WO-2004072689 A2 | 8/2004 | |
| WO | WO-2004081613 A2 | 9/2004 | |
| WO | WO-2006047383 A2 | 5/2006 | |
| WO | WO-2007005778 A2 | 1/2007 | |
| WO | WO-2007047529 A2 | 4/2007 | |
| WO | WO-2007047530 A2 | 4/2007 | |
| WO | WO-2008024766 A2 | 2/2008 | |
| WO | WO-2008077040 A2 | 6/2008 | |
| WO | WO-2008082957 A2 | 7/2008 | |
| WO | WO-2008103798 A2 | 8/2008 | |
| WO | WO-2009015161 A2 | 1/2009 | |
| WO | WO-2009015226 A2 | 1/2009 | |
| WO | WO-2009015234 A2 | 1/2009 | |
| WO | WO-2009015240 A2 | 1/2009 | |
| WO | WO-2010081093 A2 | 7/2010 | |
| WO | WO-2011026068 A2 | 3/2011 | |
| WO | WO-2011106435 A2 | 9/2011 | |
| WO | WO-2011137191 A1 | 11/2011 | |
| WO | WO-2012006616 A2 | 1/2012 | |
| WO | WO-20120106673 A1 | 8/2012 | |
| WO | WO-2012129407 A2 | 9/2012 | |
| WO | WO-2013070924 A1 | 5/2013 | |
| WO | WO-2013142323 A1 | 9/2013 | |
| WO | WO-2013166068 A1 | 11/2013 | |
| WO | WO-2014099630 A1 | 6/2014 | |
| WO | WO-2014134302 A1 | 9/2014 | |
| WO | WO-2014145562 A1 | 9/2014 | |
| WO | WO-2015066502 A1 | 5/2015 | |
| WO | WO-2015148673 A1 | 10/2015 | |
| WO | WO-2016018932 A1 | 2/2016 | |
| WO | WO-2016049059 A1 | 3/2016 | |
| WO | WO-2016201351 A1 | 12/2016 | |
| WO | WO-2017079733 A1 | 5/2017 | |
| WO | WO-2017085344 A1 | 5/2017 | |
| WO | WO-2017096087 A1 | 6/2017 | |

OTHER PUBLICATIONS

Invitation to Pay Additional Fees dated Sep. 17, 2013 in International Application No. PCT/US2013/039708.

International Preliminary Report on Patentability and Written Opinion dated Nov. 20, 2014 in International Application No. PCT/US2013/039708 (13 pages).

International Search Report and Written Opinion in PCT/US2017/048219 dated Jan. 2, 2018, 19 pages.

Communication Pursuant to Rule 164(2) and Article 94(3) dated Oct. 11, 2018, for Application No. 13725509.7, 9 pg.

Communication Pursued to Rule 161(1) and 162 EPC dated Apr. 2, 2019 in European Patent Application No. 17772509.0, 3 pages.

Hermans et al., "Change in the Accommodative Force on the Lens of the Human Eye with Age," Vision Research 48:119-126 (2008).

Communication Pursuant to Rule 94(3) EPC dated Mar. 3, 2020 in European Patent Application No. 13725509.7, 5 pages.

\* cited by examiner

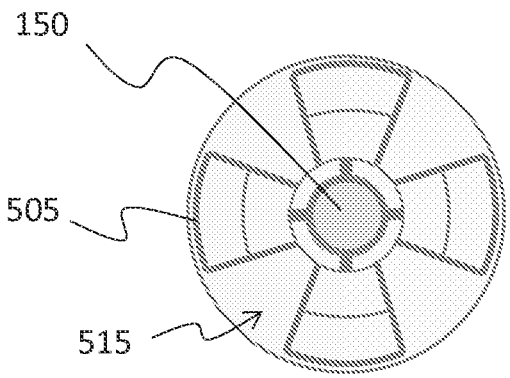
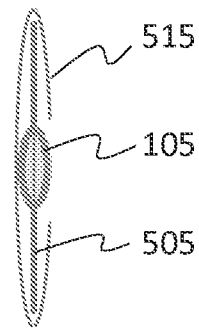
Figure 7A  Figure 7B
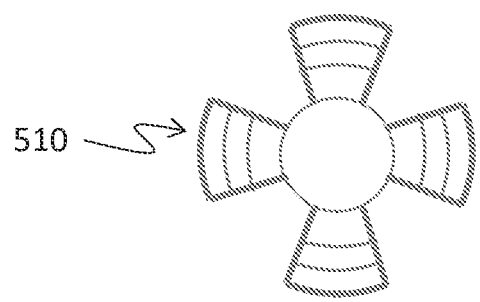
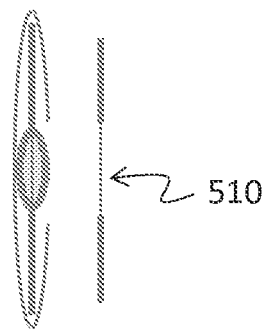
Figure 7C  Figure 7D
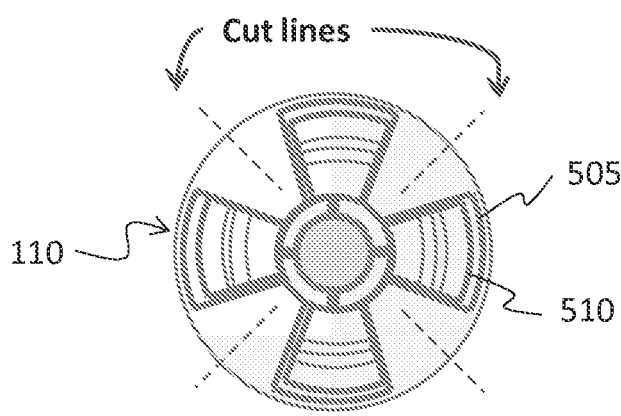
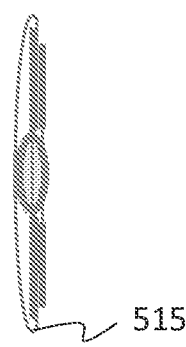
Figure 7E  Figure 7F

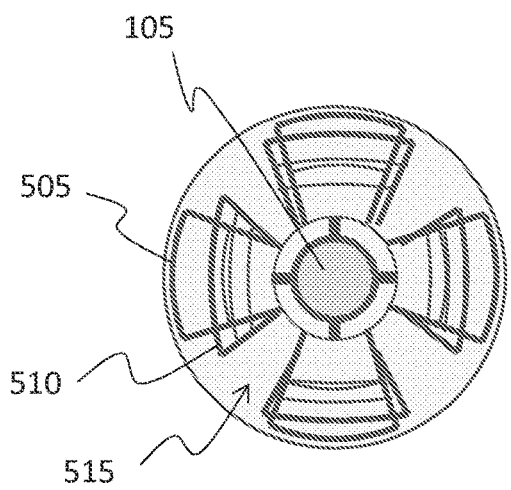
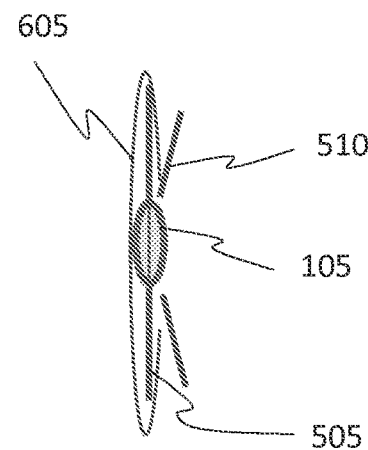
Figure 8A　　　　Figure 8B
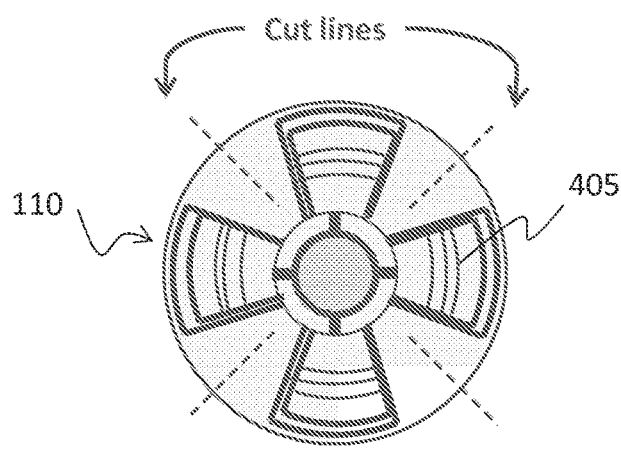
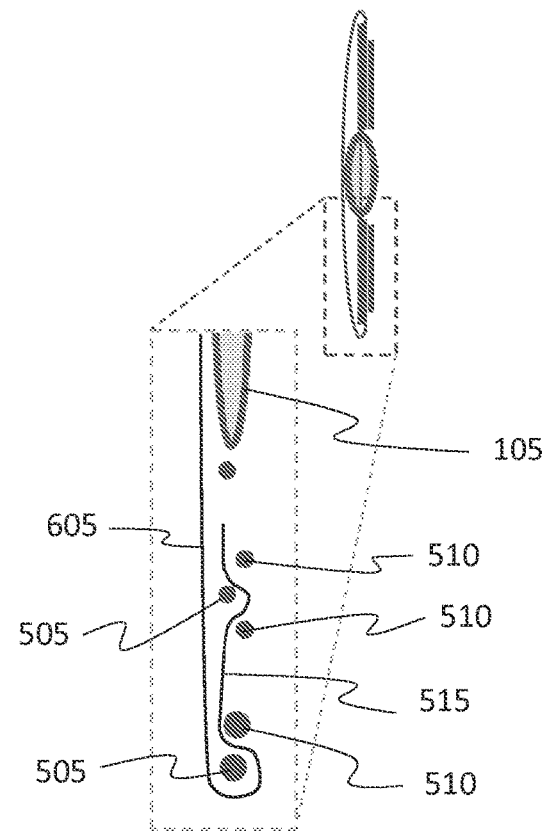
Figure 8C　　　　Figure 8D

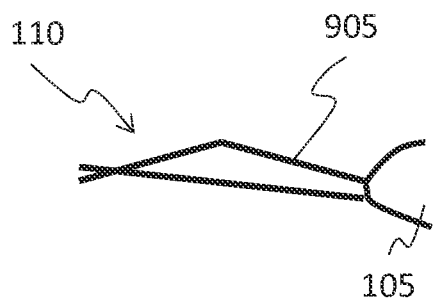
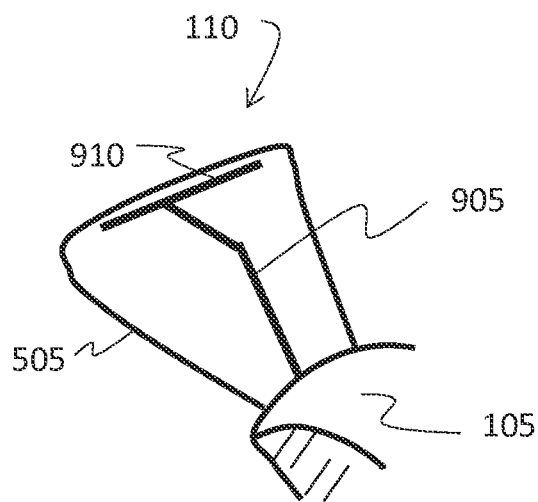
Figure 9A
Figure 9B
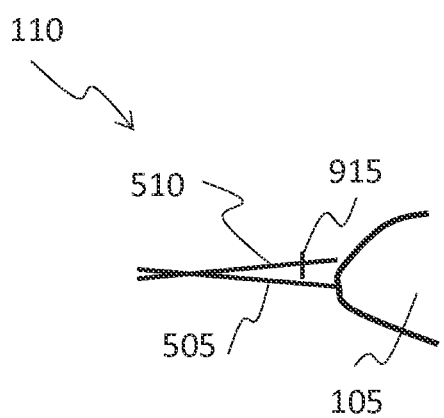
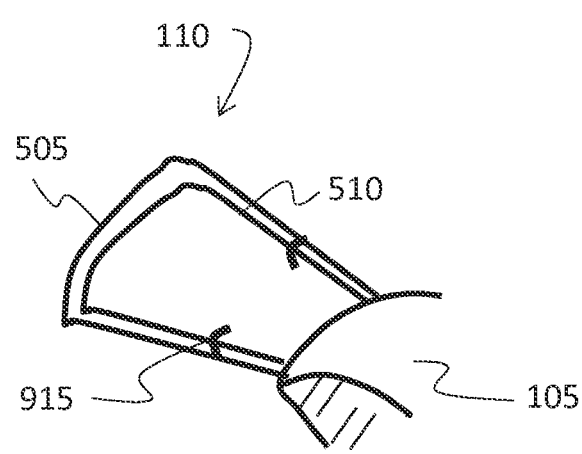
Figure 9C
Figure 9D

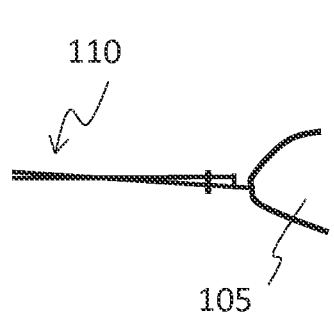
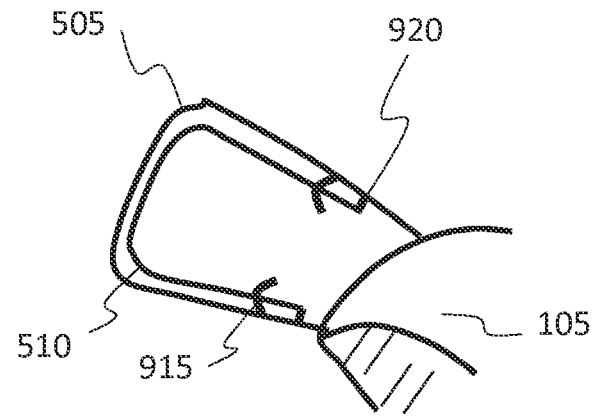
Figure 9E    Figure 9F
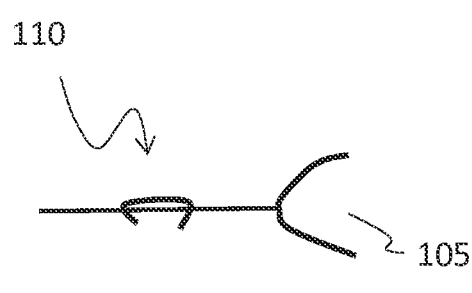
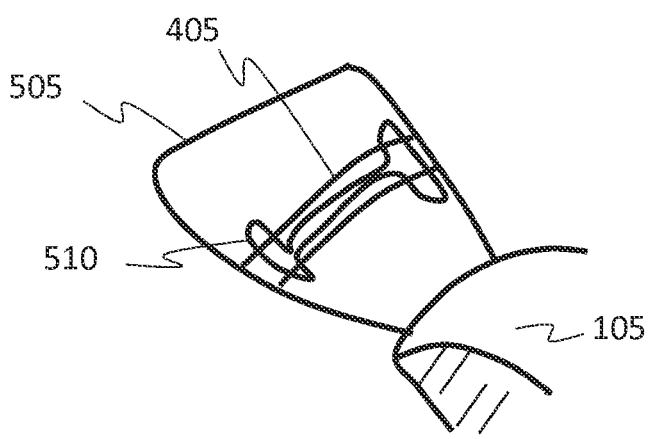
Figure 9G    Figure 9H

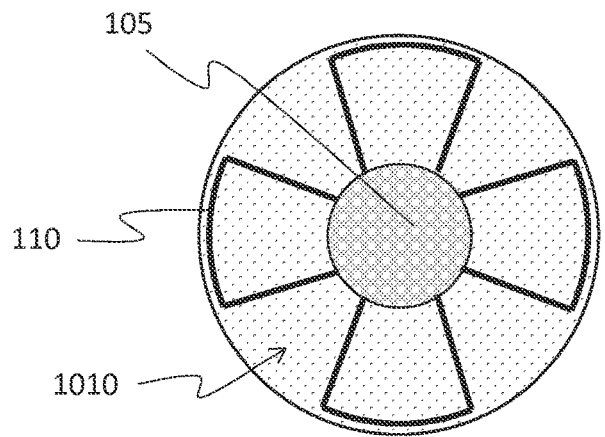
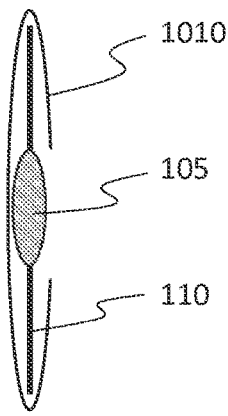
Figure 10A
Figure 10B
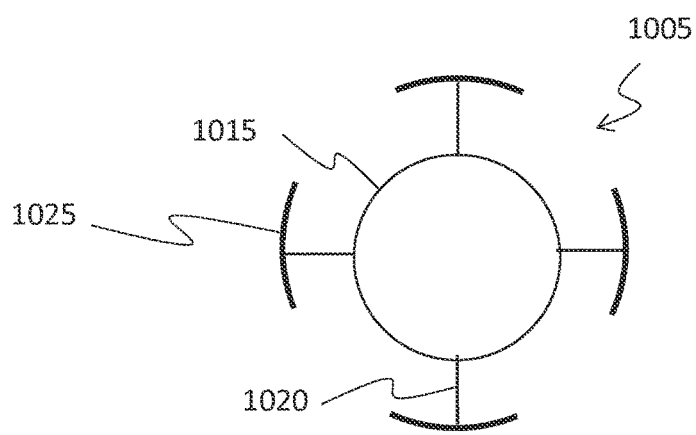
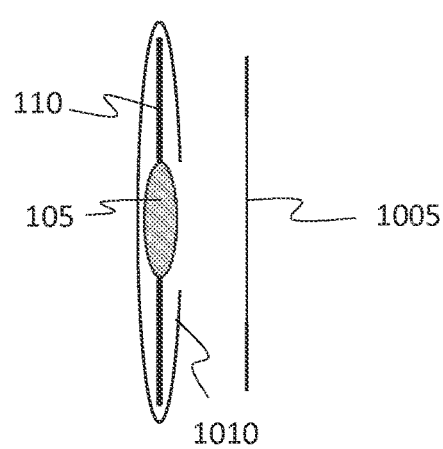
Figure 10C
Figure 10D

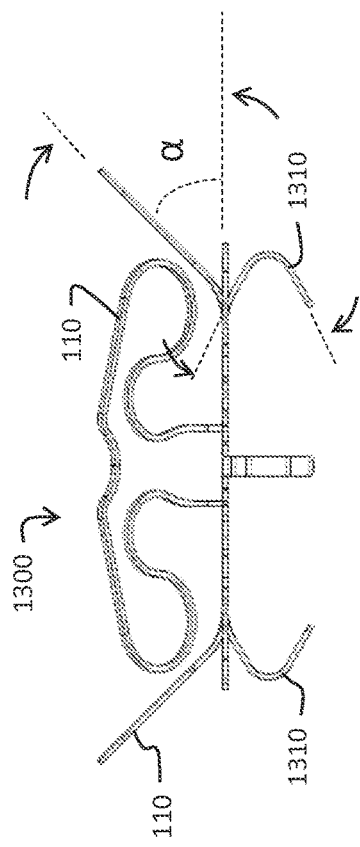
Figure 14A
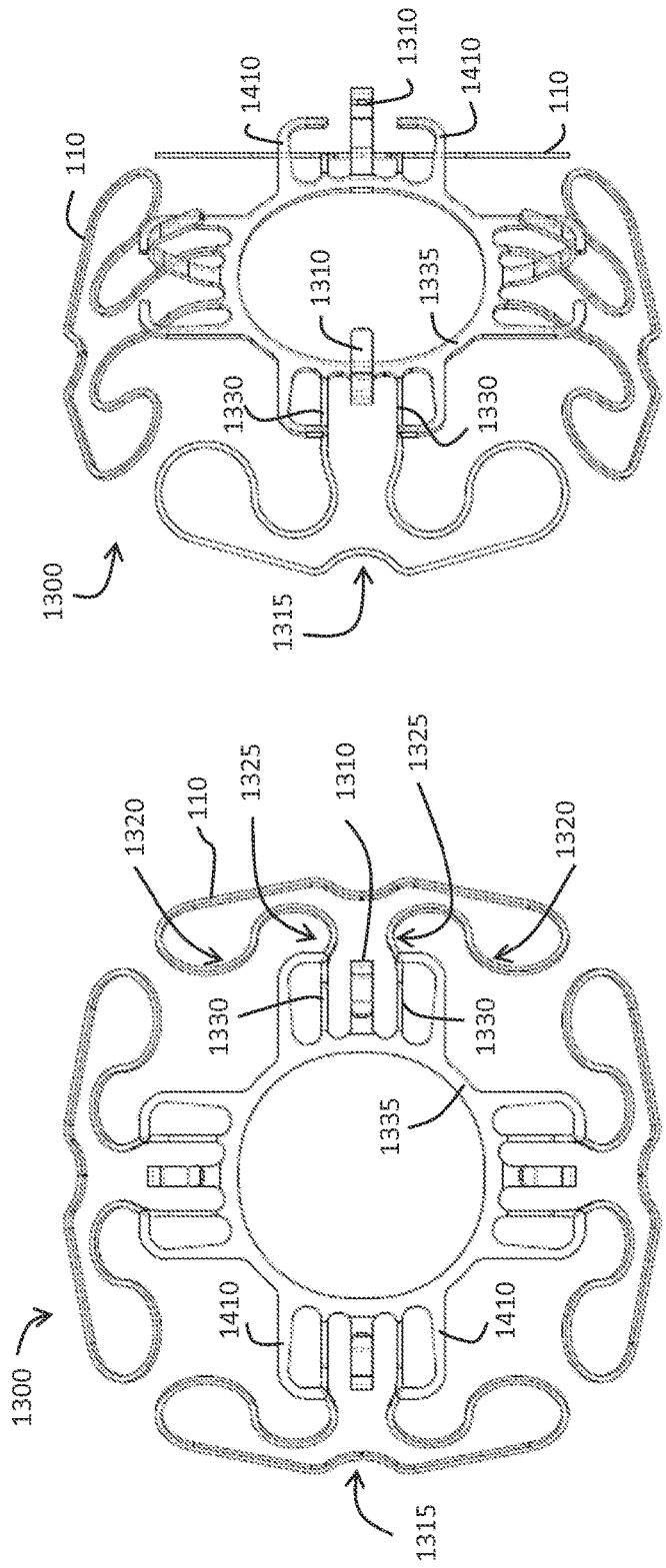
Figure 14B
Figure 14C

ACCOMMODATIVE-DISACCOMMODATIVE INTRAOCULAR LENS

RELATED APPLICATIONS

This application is a divisional of U.S. patent application Ser. No. 13/800,367 filed Mar. 13, 2013, which claims the benefit of priority under 35 U.S.C. § 119(e) to U.S. Provisional Ser. No. 61/645,320 and U.S. Provisional Ser. No. 61/645,382, both filed May 10, 2012. The entirety of each of these three applications is incorporated herein by reference.

FIELD OF THE INVENTION

The present invention relates generally to intraocular lenses. More particularly, the present invention relates to accommodative and disaccommodative intraocular lens systems and methods for improving accommodation and disaccommodation.

BACKGROUND

Under normal conditions, a healthy human eye focuses on near and distant objects by contraction and relaxation of the ciliary muscle thereby contracting and releasing the tension on the zonules in the eye. The elastic forces of the eye cause disaccommodation and the elastic recoil of the lens caused accommodation. The balance between these two opposing elastic forces is modulated by the neurologically controlled contraction of the ciliary body. The contraction of the ciliary muscle releases zonular tension (accommodative state) and allows the lens to return to a more globular or spherical resting shape. The relaxation of the ciliary muscle increases tension on zonules and elastic forces in the eye tissue overcome the inherent lens elasticity and result in stretching the lens equator and flattening the lens curvature (disaccommodative state).

In certain instances, for example when age-related opacification of the lens (cataract) interferes with vision, the natural crystalline lens of the eye needs to be removed. Generally, the natural lens is replaced with an artificial one, for example, an intraocular lens (IOL). Unfortunately, conventional IOLs, even those that profess to be accommodative, may be unable to provide sufficient spatial displacement of the lens along the optical axis to provide an adequate amount of accommodation for near vision. For an accommodative IOL to be effective, it preferably provides equally for both accommodation and disaccommodation.

In conventional extracapsular cataract surgery, the crystalline lens matrix is removed by phacoemulsification through a curvilinear capsularhexis leaving intact the thin walls of the anterior and posterior capsules, together with zonular ligament connections to the ciliary body and ciliary muscles. An intraocular lens is then placed in the capsular bag, which collapses around the IOL. A conventional monofocal IOL is rigidly fixated in the nonmoving and fibrosed capsular bag. The position of the IOL in the capsular bag is neither in the accommodated or disaccommodated state, but somewhere in between, as determined by the amount of bag contraction and IOL design. This position is called "effective lens position" and it is utilized in calculating the power of the desired optic. The power of the optic determines the single point of perfectly focused vision, often selected at a practical arm length range.

Conventional accommodative intraocular lenses (AIOL) rely on the interaction of the ciliary muscle with the zonule and capsule to induce movement of the optic of the AIOL along its optical axis. Typically, the AIOL is secured within the capsular bag that attempts to translate both the rotational and the radial stretching force exerted by the zonules in an attempt to achieve the desired axial displacement of the optic.

However, during the post-implantation fibrotic healing process, the anterior capsule fuses with the posterior capsule to form a rigid capsular disc. Loss of elasticity of the capsular disc results and constrains the amount of movement, both centrifugal and rotational, that can be generated by the eye disaccommodation forces transmitted to the IOL via zonules or by the elastic recoil of the intraocular lens within the bag and therefore, leads to a decrease in the amount of axial displacement of the lens that can be achieved. The lens neither accommodates nor disaccommodates.

Various lens systems have been designed to address this loss of accommodation. One type of passive-shift single-optic lens, the only accommodative lens currently marketed in the United States, was designed to move forward under vitreous humor pressure when presumably the ciliary muscle contracts and forces vitreous forward. Even the limited amount of accommodative amplitudes generated by this lens immediately after surgery may be lost within the first few weeks or month after surgery as capsular fibrosis ensues. No passive shift AIOLs are marketed in the US that translate ciliary muscle contraction into forward shift of the optic by direct mechanical action of the haptics.

Accommodative lens designs with single or multiple optic lens assemblies have been disclosed, for example, in U.S. Patent Publication Nos. 2009/0125106, 2005/0209692, 2007/0156236, 2009/0005866, 2007/0005136, and 2009/0248154. Dual optic lenses retain the problem of capsular fibrosis and loss of amplitude/movement even though they are reported to provide a significant amount of accommodation. However, concerns about possible long-term formation of interlenticular opacification remain.

More recently, a lens systems that employs an active-shift mechanism using repulsive mini-magnets as a means of making accommodation partially independent of the zonules and mechanical properties of the capsular bag was disclosed (see U.S. Patent Publication Nos. 2009/0204210 and 2007/0118216). Still other methods of achieving accommodation include introduction of a polymerizable fluid with a desired refractive index into the capsular bag (lens refilling). Extensive investigation into the feasibility of these methods is still needed.

U.S. Patent Publication No. 2009/0234449 discloses an intraocular lens comprising an accommodating element that is in contact with a substantial portion of the zonular contact region of the ciliary body; the accommodating element is positioned relative to optical element and configured to cooperate with the ciliary muscle, the zonules and/or the vitreous pressure in the eye to effect a shape change to the optical element. According to the '449 publication, prior art multiple lens systems can be cumbersome and may also require an axial displacement unachievable with a collapsed capsular bag and resulting ineffective accommodative mechanisms.

More recently, a lens system has been described that employs a novel zonular capture haptic (ZCH). See U.S. Patent Publication No. 2011/0307058, the entire disclosure of which is incorporated herein by reference in its entirety. The lens system provides improved accommodation via a two stage procedure. In the implantation step, Stage 1, a specially designed sectionable haptic, i.e., a ZCH, is inserted between the anterior and posterior lens capsules, allowing sufficient time for fusion and fibrosis of the two capsule leaflets to each other, thereby permanently trapping the haptic components between the capsules. During Stage 2, activation surgery may be subsequently performed to section the fused capsular bag between individual haptic components, thereby breaking the mechanical restraint that typically limits movement of other "in the bag" implanted IOLs.

SUMMARY

The basis for embodiments of the present invention is an accommodative-disaccommodative IOL (AD-IOL) with zonular capture haptics having features that resolve possible variability in biological response and allow additional methods of implantation, activation, and post-activation adjustments. The AD-IOL enables both accommodation and disaccommodation to take place. The balance between accommodation and disaccommodation is controlled by the ciliary muscle and is transmitted via zonules to the zonular capture components of the haptic system and then to the entire AD-IOL system. The AD-IOL responds to the force from a junction zone between the haptics and the optic, i.e., between an optic retainer and the optic or directly between the haptics and the optic. Sectioning the capsular bag reduces resistance to disaccommodation, and the AD-IOL responds fully to forces having a magnitude less than forces generated in the eye. The ciliary body can then counteract disaccommodation in a measured way under neural control, thereby allowing the AD-IOL to rest in a desired level of accommodation.

Embodiments of the present invention include an intraocular lens system and method for improving both accommodation and disaccommodation that remedies the loss of axial and centrifugal movement of the lens caused by shrinkage and loss of flexibility of the capsular bag following implantation of current lens systems. The AD-IOL may include an haptic system with a plurality of zonular capture haptics extending radially outward from a center portion, e.g., from an optic retainer, and sectioning zones between the ZCHs for eliminating the rigidity caused by the fibrosis of the capsular bag. Once the capsular bag has been sectioned by radial cuts, each separate segment of capsule, attached to a number of zonules and containing an individual ZCH, may move away from the other capsule segments under the zonular tension and the system disaccommodates. When the ciliary muscle contracts, it counteracts zonular tension and the elastic recoil of the ZCHs returns the IOL to an accommodated position. Thus the ZCH system may replace both the positioning and force transmission duties of the dismantled capsular bag and allows the AD-IOL to disaccommodate and accommodate under ciliary muscle control.

In one aspect, the invention relates to an intraocular lens system. The intraocular lens system includes a haptic system having a plurality of radially disposed haptics and a plurality of optic securing arms. The radially disposed haptics are adapted to move independently in response to forces of a ciliary muscle and/or zonules of an eye when implanted. The optic securing arms are adapted to releasably hold an optic.

In certain embodiments, at least one optic securing arm includes a curved member extending anteriorly from a surface of the haptic system. At least one optic securing arm may be disposed proximate a base of one of the haptics. At least one of the optic securing arms may be flexible and have shape memory. In some embodiments, the haptics define an integrated capsular bag geometry restraining device. The haptics and optic securing arms may each include one or more biocompatible plastics, biocompatible metals, and combinations thereof. For example, the haptics and optic securing arms may each include a biocompatible plastic that includes or consists essentially of polypropylene, poly(methyl methacrylate), polyamide, nylon, polyester, polyvinylidene fluoride, and silicone. The haptics and optic securing arms may each include a biocompatible metal or alloy that includes or consists essentially of stainless steel and nickel titanium alloy. In various embodiments, the intraocular lens system also includes an optic defining a groove and/or a notch, wherein at least one optic securing arm is configured to fit into the groove and/or the notch.

In another aspect, the invention relates to an intraocular lens system. The intraocular lens system includes a haptic system having a plurality of radially disposed haptics and a first restraining arm disposed proximate one of the haptics. The radially disposed haptics are adapted to move independently in response to forces of at least one of a ciliary muscle and zonules of an eye when implanted.

In certain embodiments, the first restraining arm is configured to be reusable. The haptic system may be tunable to adjust a range of at least one of accommodation and disaccommodation. The intraocular lens system may also include an extension coupled to the first restraining arm. The extension may include, for example, an accommodation travel reducing sleeve or a disaccommodation travel reducing sleeve. In some embodiments, the intraocular lens system also includes a second restraining arm, wherein a base of one of the haptics is disposed between the first and second restraining arms. The intraocular lens system may also include an optic fused to the plurality of radially disposed haptics.

In another aspect, the invention relates to a method for improving accommodation of an intraocular lens system in an eye. The method includes: (a) providing the intraocular lens system, which includes a haptic system; (b) positioning at least a portion of the haptic system in a capsular bag of the eye; and (c) inserting an optic into the haptic system.

In certain embodiments, the optic is inserted into the haptic system after the positioning of at least the portion of the haptic system in the capsular bag of the eye. The method may also include allowing the capsular bag to fuse prior to inserting the optic into the haptic system. Alternatively, the method may include allowing the capsular bag to fuse after the optic is inserted into the haptic system. In some embodiments, the method includes removing the optic. The method may also include inserting a second optic into the haptic system.

In another aspect, the invention relates to a method for improving accommodation of an intraocular lens system in an eye. The method includes: (a) providing the intraocular lens system, which includes a haptic system having a plurality of haptics; (b) positioning at least a portion of the system in a capsular bag of the eye; (c) locking a position of at least one of the haptics; and (d) releasing at least one locked haptic.

In certain embodiments, the method also includes allowing the capsular bag to fuse prior to releasing the at least one locked haptic. The method may also include relocking at least one released haptic.

In another aspect, the invention relates to a method for improving disaccommodation of an intraocular lens system in an eye. The method includes: (a) providing the intraocular lens system, which includes a haptic system; (b) positioning at least a portion of the haptic system in a capsular bag of the eye; and (c) disaccommodating the intraocular lens system.

A diameter of the haptic system increases concomitant with an increase of a diameter of the capsular bag during disaccommodation.

In certain embodiments, the method also includes, prior to disaccommodating the intraocular lens, allowing the capsular bag to fuse through at least a portion of the haptic system, and releasing the fused capsular bag. In one embodiment, releasing the capsular bag includes sectioning the fused capsular bag by making radial cuts therethrough to define a plurality of capsule segments. The haptic system may include a plurality of zonular capture haptics. In some embodiments, sectioning the capsular bag includes separating the zonular capture haptics such that each separate capsular segment (i) includes a zonular capture haptic and (ii) is attached to a plurality of zonules, and the intraocular lens system disaccommodates and accommodates under ciliary muscle control.

In various embodiments, zonules attach to the haptic system during fusion, and the zonules slacken during disaccommodation. The intraocular lens system may move to a disaccommodated position when the ciliary muscle relaxes. The intraocular lens system may move to an accommodated position when the ciliary muscle contracts. In one embodiment, the ciliary muscle controls both a degree of accommodation and a degree of disaccommodation of the intraocular lens system.

In another aspect, the invention relates to an intraocular lens system. The intraocular lens system includes: (a) an optic having an equator; and (b) a haptic system having a plurality of haptics fused to the optic and projecting radially outward from the optic. Each of the haptics includes an equatorial segment at least one radial segment, with each of the haptics having a proximal end and a distal end relative to the optic. The plurality of haptics defines a disc that is approximately coextensive with a capsular bag of an eye and includes spaces between adjacent haptics.

In certain embodiments, the haptics are attached to the optic proximate the equator of the optic. The haptics may be regularly spaced around the optic. In one embodiment, a distance between the radial segments at the proximal end of the haptic is less than a distance between the radial segments at the distal end of the haptic. At least one of the haptics may include a loop, which may be roughly rectangular or trapezoidal. In some embodiments, the loop defines an open interior space to allow fusion of the capsule through and around the loop. At least one of the haptics may have a T-shape.

In certain embodiments, upon implantation in the eye, the equatorial segment is configured to capture a zonular insertion, and the radial segment connects the zonule to the optic. Each of the haptics may include a flexible region at the proximal end of the haptic that allows the haptic to move anteriorly and posteriorly relative to the optic. In one embodiment, the haptics are angled posteriorly. For example, the haptics may be angled at an angle from 0 degrees to 50 degrees, or from 30 degrees to 45 degrees.

In various embodiments, the haptics include a biocompatible material. The biocompatible material may include or consist essentially of, for example, biocompatible plastics, biocompatible metals, and combinations thereof. For example, the biocompatible material may be a biocompatible plastic that includes or consists essentially of polypropylene, poly(methyl methacrylate), polyamide, nylon, polyester, and polyvinylidene fluoride. The biocompatible material may include or consist essentially of a biocompatible metal such as stainless steel and/or nickel titanium.

In certain embodiments, the haptics are zonular capture haptics adapted to capture a point of zonular insertion by fusing and becoming integral with an equator of the capsular bag. The haptics may be adapted to become two-joint articulated skeletons replacing the capsular bag after it is dismantled by radial cuts after the intraocular lens system is inserted into the eye. In some embodiments, the space between adjacent haptics is configured to allow the capsular bag, after fusion, to encompass the equatorial and radial segments, to contain the two articulated skeletons. At least one haptic may also include an anchor extending across a width of the haptic. The intraocular lens system may also include a geometry restraining member that is configured to maintain a geometry of the plurality of haptics during a fusion contraction phase after the haptics and optic are inserted into the eye, and is adapted to be implanted to cooperate with the haptics and optic.

In various embodiments, the geometry restraining member is adapted to maintain the diameter and the angulation of the haptics during the fusion contraction phase. The geometry restraining member may include at least one radial element having sufficient rigidity to resist contraction of the capsular bag and to prevent distortion of the haptic system. In one embodiment, the geometry restraining member includes at least one arm configured to immobilize the haptic system in a disaccommodated configuration during fusion of the capsular bag. The geometry restraining member may be adapted to be sectioned and rendered inoperative at the stage two surgery. In certain embodiments, the geometry restraining member is reusable. The geometry restraining member may include a biocompatible material. The geometry restraining member may be integrated into the haptic system. The geometry restraining member may be structurally separate from the haptic system.

In another aspect, the invention relates to a double intraocular lens system. The double intraocular lens system includes: (a) a first and a second optic, each optic having an equator; and (b) a first and second plurality of haptics attached to the first and second optics respectively and projecting radially outward from the respective optic. Each of the haptics includes an equatorial segment and at least one radial segment and has proximal and distal ends relative to the optic. The first and second pluralities of haptics collectively define a disc that is roughly coextensive with a capsular bag of an eye and includes spaces between adjacent haptics to allow cutting therebetween.

In certain embodiments, the haptics are attached to the optic at or near the equator of the optic. In one embodiment, haptics are regularly spaced around the optic. At least two haptics may be attached to each of the first and second optics. A distance between the radial segments at the proximal end of each of the haptics is less than a distance between the radial segments at the distal end of the haptic. Each haptic may include a loop. In one embodiment, the loop is trapezoid-shaped. The loop may define an open interior space to allow fusion of the capsule through the loop.

In some embodiments, each of the haptics includes a flexible region at the proximal end of the haptic that allows the haptic to move anteriorly and posteriorly. The haptics of the first optic may be angled posteriorly and the haptics of the second optic may be angled anteriorly. For example, the haptics of each optic may angled at an angle from 0 degrees to 50 degrees, or from 30 degrees to 45 degrees. The haptics may include a biocompatible material, which may include or consist essentially of biocompatible plastics, biocompatible metals, and combinations thereof. In one embodiment, the biocompatible material is a biocompatible plastic such as polypropylene, poly(methyl methacrylate), polyamide, nylon, polyester, and/or polyvinylidene fluoride. The biocompatible material may be a biocompatible metal such as stainless steel and/or nickel titanium.

In another aspect, the invention relates to a method of implanting the double intraocular lens system. The method includes: (a) providing the double intraocular lens system; (b) positioning the first optic and first plurality of haptics in a capsular bag of the eye; (c) positioning the second optic and second plurality of haptics in the capsular bag; and (d) sectioning the capsular bag by making radial cuts therethrough. The first and second optics move independently of each other in response to ciliary muscle control.

In various embodiments, the method includes allowing the capsular bag to fuse prior to making radial cuts therethrough. The first and second plurality of haptics may be positioned such that the haptics are staggered, defining sectioning lines between the haptics of the first plurality and the haptics of the second plurality.

In another aspect, the invention relates to an accommodating intraocular lens system. The intraocular lens system includes a haptic system having a plurality of radially disposed capsule-fixing haptics. Each of the capsule-fixing haptics includes a positioning member and a capsule-fixing member that cooperate to sandwich a portion of an anterior and/or posterior capsule of an eye therebetween when implanted.

In certain embodiments, the haptics define a disc that is roughly coextensive with a capsule of the eye when implanted. A portion of each of the haptics may be flexible, allowing movement of the haptic at least one of anteriorly and posteriorly. The capsule-fixing haptics may be attached to an optic near an equator of the optic. In some embodiments, each of the positioning- and capsule-fixing members includes a cross member, and the capsule-fixing cross member is adapted to be pushed through the positioning cross member to secure the capsule between the positioning and capsule-fixing members.

In various embodiments, the positioning member is adapted to be positioned within the capsular bag and the capsule-fixing member is adapted to be positioned outside the capsular bag. The capsule-fixing haptics may be generally coextensive with the capsule when inserted into the eye. In one embodiment, the accommodating intraocular lens system also includes an optic, wherein the capsule-fixing haptics extend outwardly and are angled posteriorly with respect to the optic. The accommodating intraocular lens system may also include an optic, and the capsule-fixing haptics may be regularly spaced around the optic. Each of the capsule-fixing haptics may include a generally flat loop having a generally open interior space to allow fusion of the capsule to substantially encase the loop. The loop may be roughly trapezoid-shaped. The trapezoid-shaped loop may have a proximal end and a distal end, the proximal end being narrower than the distal end.

In certain embodiments, a width of the capture-fixing member is less than a width of the positioning member of the haptic, such that the capture-fixing member fits within the positioning member when the capture-fixing member and the positioning member of the haptic are engaged. The haptics may be regularly spaced. The haptics may include a biologically inert material. In one embodiment, each haptic is adapted to be affixed to the capsule prior to fusion of the capsule. In some embodiments, the accommodating intraocular lens system also includes an optic, wherein each haptic and attached capsular portion form an articulated skeleton that permits flexion at two points only: (i) a junction between the zonules and the equator of the capsule, and (ii) a junction between the haptic and the optic. Each haptic and attached capsular portion may form an articulated skeleton that is sufficiently mechanically rigid to prevent contraction of the capsule to alter alignment, position, or geometry of the haptic system.

In another aspect, the invention relates to an accommodating intraocular lens system. The accommodating intraocular lens system includes: a haptic system having a plurality of capsule-fixing haptics extending radially outward to define a disc that is roughly coextensive with a capsule of an eye when implanted. Each of the haptics includes a first clamping member and a second clamping member that cooperate to sandwich an anterior or posterior capsule therebetween.

In certain embodiments, the first and second clamping members oppose each other to frictionally hold the capsule in place therebetween. The accommodating intraocular lens system may also include an optic. In one embodiment, the haptics are fused to the outer edge of the optic. The haptic system may include an optic retainer adapted to hold the optic.

In another aspect, the invention relates to a method for improving accommodation. The method includes (a) providing an accommodating intraocular lens system (AIOL). The AIOL system includes a haptic system having a plurality of capsule-fixing haptics extending radially outward to define a disc that is roughly coextensive with a capsular bag of an eye when implanted. Each of the haptics include a first member and a second member that cooperate to securely affix the capsule therebetween. The method also includes: (b) positioning at least a portion of the system in the capsular bag of the eye; (c) affixing the capsular bag between the first and second members of at least one haptic, thereby affixing the haptic system to the capsular bag; and (d) making a plurality of substantially radial cuts in the capsular bag at intervals between the haptics to section the capsular bag.

In certain embodiments, the haptics are fused to an outer edge of an optic. The haptic system may include an optic retainer adapted to hold an optic. In one embodiment, the method includes inserting the optic into the optic retainer. The plurality of haptics may be regularly spaced with sectioning intervals therebetween. In some embodiments, the method also includes allowing the capsular bag to fuse prior to making the substantially radial cuts. The method may also include maintaining the eye in an unaccommodative state during fusion. The unaccommodative state may be maintained by administering an agent (e.g., atropine) to inhibit accommodation. The method may also include maintaining the eye in an accommodative state during fusion. The accommodative state may be maintained by administering an agent (e.g., pilocarpine) to promote accommodation. The capsular bag may be sectioned between adjacent haptics. In one embodiment, the cuts are made radially and extend from a visual axis to an equator of the capsular bag.

In another aspect, the invention relates to a method for positioning an intraocular lens system relative to a capsule of an eye. The method includes (a) positioning in the capsule an intraocular lens system. The intraocular lens system includes a haptic system having a plurality of capsule-fixing haptics extending radially outward to define a disc that is roughly coextensive with a capsule of an eye when implanted. Each of the capsule-fixing haptics includes a positioning member and a capsule-fixing member that cooperate to sandwich a portion of an anterior and/or posterior capsule therebetween. The method also includes (b) engaging the positioning member and the capsule-fixing member of at least one capsule-fixing haptic with the capsule therebetween to sandwich a portion of the capsule between the positioning member and the capsule-fixing member.

In various embodiments, the intraocular lens system includes an optic. The haptics may be fused to an equator of the optic. In some embodiments, the haptic system includes an optic retainer, and the method includes inserting the optic into an optic retainer.

These and other objects, features and advantages of this invention will become apparent from the following detailed description of the various aspects of the invention taken in conjunction with the accompanying drawings.

BRIEF DESCRIPTION OF THE DRAWINGS

FIGS. 7A-7F are schematic top and side views of an alternative embodiment of an AD-IOL in which positioning components of the haptic are separate from the capsule-fixing components, in accordance with an embodiment of the invention;

FIGS. 8A-8D are schematic top and side views of a haptic system with both positioning and capsule-fixing members of each haptic attached to the optic or optic retainer, and the haptics having cross-members that create a tortuous path to secure the capsule between positioning and capsule-fixing members of each haptic, in accordance with an embodiment of the invention;

FIGS. 9A-9H are schematic views of a variety of mechanisms by which the positioning and capsule-fixing members of each haptic may be engaged, for example, an interlocking T-bar (FIGS. 9A and 9B), a hook assembly (FIGS. 9C-9F), and a capsule-fixing member that wraps around two cross members of a positioning member of a haptic (FIGS. 9G and 9H), in accordance with an embodiment of the invention;

FIGS. 10A-10G are schematic side and top views of several temporary restraining devices that maintain the AD-IOL in a flat, disaccommodative state during fusion/fibrosis and are removed or disabled during the activation Stage 2 procedure, in accordance with an embodiment of the invention;

FIGS. 14A-14C are schematic side, top, and perspective views of the haptic system of an AD-IOL of FIGS. 13A-13B, in a fully shaped configuration, in accordance with an embodiment of the invention;

DETAILED DESCRIPTION

Figure 1:
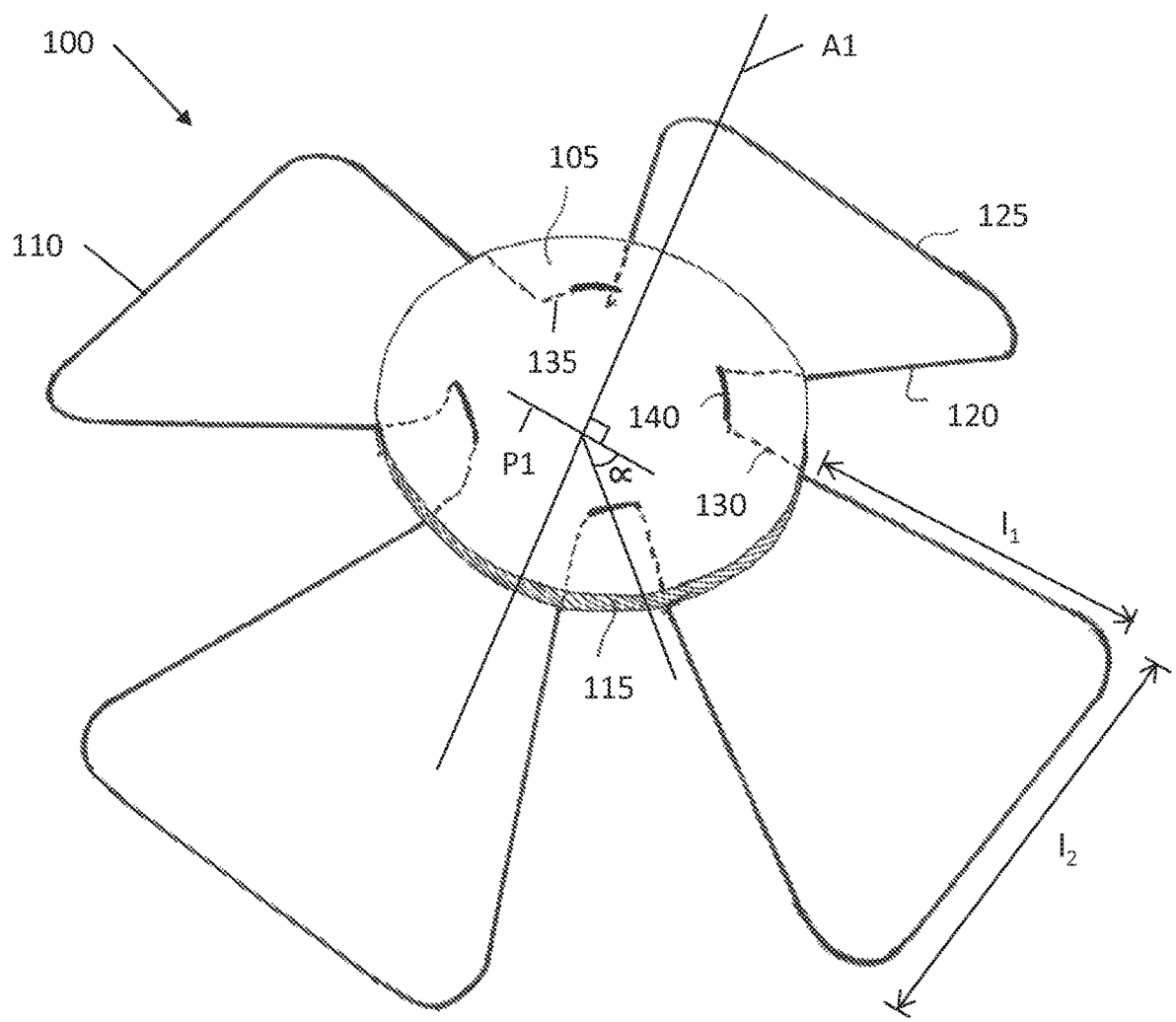
FIG. 1 is a schematic perspective view of a fused single optic and with passive ZCH fixation, in accordance with an embodiment of the invention.

All patent applications, patents and other references cited herein are hereby incorporated by reference in their entirety into the present disclosure.

In ophthalmology, the term "haptic" refers to a structure that extends out from an optic element of an intraocular lens, usually for holding the lens in place within the capsular bag of the eye. Herein, "haptics" are sometimes referred to as "zonular capture haptics," or collectively as a "zonular capture haptic system," or simply "haptic system" and refer to structures or material that not only assist with placement and centration of the lens within the capsular bag to transmit zonular movement to the lens, but also permit secure fixation in between or to the anterior or posterior capsule following removal of the natural lens and placement of the artificial lens. The haptics define individual "sections" of the capsule, which can be separated by making cuts in the capsule between haptics. Following sectioning, each separate section zonules attached to equatorial capsule is "captured" by engagement of the capsule by the ZCH. A haptic system may also include an optic retainer for holding an optic. An "optic retainer" is a portion of the haptic system that holds the optic, e.g., a ring, pins, or other attachment mechanism. As used herein, "capsule" and "capsular bag" may be used interchangeably.

Conventional accommodating lenses typically involve converting diametric movements of the ciliary muscle into forward and backward movement of an optic portion of the IOL relative to the retina. For example, the only accommodating IOL currently marketed in the US is a rigid, single optic IOL designed to rely on a forward translation of the optic to produce an increase in optical power of the eye. Movement of the IOL is produced by ciliary muscle contraction, presumed capsular bag elasticity and/or suggested changes in vitreous cavity pressure to create an optical change in the eye.

However, implantation of the IOL into the capsule is followed by a natural physiological process not unlike applying a shrink-wrap film, in which the anterior and posterior capsular bag surfaces fuse around the haptics and seal the IOL within the fibrotic capsule. Furthermore, the fusing capsule undergoes fibrosis. During fibrosis, the capsular bag undergoes further contraction and loss of elasticity. As a result of this process, the IOL may be immobilized within the fibrosed capsular disc and movement of the optic along the optical axis is extremely limited. The IOL may be unable to undergo disaccommodation when the ciliary muscle relaxes and unable to undergo accommodation when the ciliary muscle contracts.

Embodiments of the present invention are directed to a haptic system designed to restore capsular flexibility lost during fusion and fibrosis. This haptic system allows an implanted lens to transition more effectively between the accommodated and unaccommodated states, that is, in a fashion similar to the natural lens in response to forces applied to the capsule by the ciliary muscle and zonules. This procedure has the effect of reducing the rigidity of the fused capsular disc and allows the optic in conjunction with the flexibility of the haptics to freely move axially relative to the eye. The AD-IOL of embodiments of the present invention may be fixated to the capsule in one of two alternative ways. The ZCH may be passively secured inside segments of the fused capsular bag, or may have interlocking members that fixate the haptics mechanically to the anterior, posterior, or both capsules at the time of surgical implantation.

In the passively secured ZCH embodiment, a plurality of haptics are attached to the optic or an optic retainer for holding the optic and project radially outward. Each of the haptics has an equatorial segment at a distal end of the haptic and at least one radial segment connecting the equatorial segment and the optic or optic retainer. One or more haptics may be regularly spaced around the optic or optic retainer with a space between adjacent haptics. Collectively, the plurality of haptics define a disc that is roughly coextensive with a capsular bag of an eye, the equatorial segment of each haptic being disposed at the junction between zonules and the equator of the capsular bag, thereby capturing the end of the zonules. In certain embodiments, each haptic includes a biocompatible material that is formed into a roughly rectangular, trapezoidal loop, or T-shaped configuration with the widest part of the haptic being at the distal end (equatorial segment). Once the structure of the capsular bag is dismantled by radial sectioning from its center to its equator, the haptic system assumes the function of the previous capsular bag and works as an articulated skeleton, attached to zonules at one end and the optic or optic retainer at the other. The residual segments of capsule fused anterior to posterior are reduced in function to securing the equatorial segment of the ZCH like two pieces of VELCRO hook-and-loop fasteners. The haptics may be angled posteriorly to the optic at an angle of about 0° to about 50°; in some embodiments, an angle of about 10° to about 50°, is advantageous. More preferably, the angle may range from 30 to 45 degrees. The material from which the haptic loops are made is generally sufficiently resilient so that the haptics retain their shape following insertion into the capsule.

In the actively secured ZCH with capsular fixating interlocking members embodiment, regularly spaced haptics with interlocking components can be adapted to lock onto the capsule following placement of the optic or optic retainer with the haptics or positioning components in the capsular bag and the locking components outside of the bag, either anterior or posterior, and to permit the sectioning of the capsule during the same surgical procedure or at any time after. By achieving immediate mechanical capsular fixation, sectioning of the capsule can be performed without the need for a waiting period of capsular fusion. Sectioning allows adjacent haptics to move freely from each other; each haptic can, therefore, move independently in response to ciliary muscle and zonular forces on the capsular segments.

The interlocking system with capsular fixating interlocking members may be implanted before the capsular bag is sectioned at regular intervals determined by spaces between the haptics. The haptics can lock on the anterior capsule, the posterior capsule, or both, together or independently, as determined by the design of the particular embodiment. Once the AD-IOL is implanted and centered, the locking component of each individual haptic may be squeezed, pressed, clamped, clipped or otherwise locked against the corresponding haptic, affixing the capsule therebetween, and mechanically securing, trapping a portion of the capsule in a fixed position between the positioning member and capsule-fixing member of each haptic.

The locking element or the locking point can be positioned at any relative point from the haptic-optic junction to the equatorial end of the haptic, or anywhere relative to the point of zonular insertion on the capsule, as determined to be beneficial for any particular design. The interlocking system can be locked, unlocked and relocked repeatedly, during the implantation surgery or at any time after.

The ability to actively lock unto the capsule provides several advantages, the first of which is the ability to condense two surgical steps into one. Some other applications of the capsular interlocking systems include the ability to secure a stronger or longer lasting attachment to the capsule, the ability to better fixate any IOL to the capsule or capsular fragments, and the ability to generate complex optomechanical systems by selecting specific fixation points on the anterior, posterior, or both capsules.

An optic may be incorporated into the AD-IOL in one of two alternative ways, i.e., as a fused optic or as a replaceable optic. In the fused optic version, a ring or other optic retainer for holding an optic may be eliminated and the zonular capture haptics are attached directly to the optic. In this way, the bulk of the AD-IOL is reduced, allowing for a larger optic that can still allow the AD-IOL to be inserted through a routine small surgical incision and most importantly, immediately provide focused vision at a distance, in the same fashion now customary with standard non-accommodating IOLs. When the accommodation function is activated at a Stage 2 surgical procedure, the patient gains the additional benefit of improved accommodation and focused vision at near distances. Additional features described below allow embodiments of this AD-IOL to become secured between the fused segments of the former capsular bag and replace the structure and function of the former capsular bag with the zonular capture haptics.

In particular, referring to FIG. 1, embodiments of an AD-IOL of the present invention include an integrated AD-IOL system 100 in which an optic 105 is integrated with a haptic system, without the use of an optic retainer. A plurality of haptics 110 (e.g., four haptics) may be arranged in a circle around an equator 115 of the optic 105 and extend outwardly from the optic 105. The arrangement of haptics 110 generally defines a ring that is coextensive with the capsular bag. In the pictured embodiment, haptics 110 are roughly trapezoidal in shape and form a closed loop that defines both the equator of the capsular bag and the shape of the capsular wedges after the sectioning step. The haptics 110 reinforce the capsular wedges and create a "skeleton-like" structure, which allows bending at the equator-zonular junction and haptic-optic junction.

Radial segments 120 of the haptics 110 may have a length $l_1$ of, e.g., 3 mm to 7 mm, preferably 5 mm, and may form an angle α of 30 degrees with a plane P1 that is perpendicular to an optical axis A1 of the optic 105. The angle α is the angle anticipated between the haptics and the optic when the device is in the maximally accommodated configuration, taking into account the anticipated amount of ciliary muscle contraction and the amount of axial movement of the optic. The length $l_1$ of the radial segments 120 is preferably selected such that when the IOL is flattened, the diameter of the IOL is equal or slightly larger than the diameter of the capsular bag in the disaccommodated position after the lens has been removed and the bag is empty. The equatorial segments 125 of the haptics 110 may have a length $l_2$ of, e.g., 1 mm to 7 mm, preferably 5 mm. The length $l_2$ of the equatorial segments 125 may be selected such that a sum of the lengths $l_2$ for the haptics 110 is sufficient to extend along the equator of the capsular bag, minus the lengths of safe zones between haptics 110 for sectioning the bag. The safe zones are preferably sufficiently large to allow for physical cutting with instruments. Further, after the cut, preferably an edge of adherent capsule is disposed on the outside of the haptic 110, i.e., a bare haptic 110 is preferably not exposed after the cut. In some embodiments, the radial segments 120 of the haptics 110 extend under the surface of the optic 105 to define a radial junction segment 130 along a bottom side of the optic 105, a penetrating segment 135 that penetrates or passes through the optic 105, and a lateral junction segment 140 that extends along a top surface of the optic 105. In an embodiment the haptics 110 may be made of a continuous loop of suture with a USP designation of 7-0 Prolene®. The junction segments 130 and 140 are, e.g., 1 mm in length. The penetrating segment 135 may be located, e.g., 1 mm from the edge of the optic 105 and may be equal to the thickness of the particular optic 105 at that point. The equatorial segments 125 of the haptics 110 may define a circle with a diameter of, e.g., 13 mm. The optic 105 may be, e.g., a 5 mm diameter optic made of silicone polymer.

A similar embodiment may have 3 or more haptics 110 with radial and equatorial segments 120, 125 having lengths $l_1$ and $l_2$ ranging from 3-7 mm, made from Prolene® 2-0 to 8-0 in size, or other biocompatible semi-rigid, elastic/resilient material, extending at an angle α to the optic ranging from 0-50 degrees.

The optic 105 can be made of soft acrylic polymer or more solid PMMA or any other suitable optic material and can be about 5 to 6 mm in diameter. Collectively, the equatorial segments of the plurality of haptics 110 define a circle having a diameter of about 10 to about 14 mm. The haptics 110 can penetrate the optic 105 vertically or horizontally at the equator 115 or within about 0.1 to about 1.5 mm of the equator 115 of the optic 105. Haptics 110 may be regularly spaced around the equator 115 of the optic 105, that is, the haptics 110 are preferably evenly spaced. The number and size of the haptics 110 is selected such that that the overall haptic design provides for sectioning zones between haptics 110.

In addition to providing centering of the optic 105 within the capsule like the haptics 110 in conventional intraocular lenses, the haptic system provides closed-loop, frame-like structures that allow contact between the anterior and posterior capsules so that the processes of capsular fusion and fibrosis are not impeded, thereby creating a skeletal support for the capsular disc. The natural post-phacoemulsification healing process is important for integration of the haptics 110 into the capsular disc. Furthermore, the haptics 110 are preferably regularly arranged around the optic 105 to transmit zonular forces to the optic 105 in an evenly distributed fashion and with a space between adjacent haptics 110 to permit the fused capsular disc to be cut at regular intervals.

The number and size of haptic members 110 varies depending on the number of sections that the clinician determines to be optimal. An optimal number of sections may be determined to be that number which will permit the greatest axial movement of the optic 105 that can be achieved without compromising the integrity of the capsular bag sections. Further considerations regarding the number of sections to be made include allocating an amount of time for sectioning that the clinician feels is appropriate for the safety and well-being of the patient.

Each of the haptics may include a flexible region at the proximal end of each haptic, which allows the haptic to move anteriorly and posteriorly relative to the optic.

The size/dimension and shape of haptics 110 is designed to provide maximum extension of the capsular bag during fusion and maximum contact between the equatorial components 125 of the haptics and the equator of the capsular bag. In doing so, the equatorial haptic components 125 may is configured to capture a zonular insertion and accordingly, become attached to the point of insertion of zonules on the capsular bag, thereby capturing the zonular action and transferring it to the remainder of the haptic 110, once the capsular bag has been dismantled by radial sections. The radial segment may connect the zonule to the optic. The fused remnants of capsule function like VELCRO hook-and-loop fasteners, securing the haptic 110 therebetween, and no longer supporting the IOL.

In order to gain accommodative ability, the optic 105 moves to an anterior position during accommodation and to a posterior position during disaccommodation. Therefore, the AD-IOL is anteriorly vaulted during ciliary body contraction and flat or nearly flat during ciliary body relaxation.

In order to achieve this vaulting, the haptics 110 can both radially extend outward from the optic 105 and be angled posteriorly to the optic 105 in their natural resting position. A posterior angulation a of the haptics 110 to the plane of the optic may be between 0 and 50 degrees. In some embodiments, a posterior angulation a from about 30 to 45 degrees allows for optimal axial movement. In one embodiment, this angulation can be achieved by having the haptic 110 enter the optic 105 at an angle. In another embodiment, the angle can be achieved by having a flex zone in the haptics 110 bent to the desired angle.

A portion of the haptic 110, in accordance with embodiments of the invention, may be rigid or semi-rigid; the haptic 110 may additionally have a portion that is flexible and/or elastic. In one embodiment, the haptics 110 are rigid or semi-rigid with a portion of the haptic 110 at or near the optic/haptic junction that is flexible, allowing the haptic 110 to retain its shape while allowing it to move anteriorly and posteriorly relative to the optic 105. The portion of the haptic 110 that attaches to the optic 105 or optic retainer may have lower rigidity and increased flexibility to assist the return of the AD-IOL to a vaulted configuration when zonular tension on it is reduced.

In one embodiment, the haptic 110 may be defined by a generally continuous element or a single continuous element of varying widths or thicknesses as long as the ability of the anterior and posterior capsules to securely fuse through the haptic 110 is preserved. The haptics 110 are preferably made of a suitable nonabsorbable surgical material such as metallic surgical wire, polymer suture, or the like. Additional exemplary suitable materials include polypropylene, poly (methyl methacrylate), polyamide, nylon, polyester, polyvinylidene fluoride, silicone, stainless steel, nickel titanium alloy such as nitinol, other biocompatible plastics and metals, or a combination thereof. In one embodiment, haptics 110 are constructed of polypropylene suture material, such as Prolene® (manufactured by Ethicon, based in Somerville, N.J.) and with a USP designation of 8-0 to 4-0 Prolene®. The haptics 110 may optionally include additional structures within the haptic frame defined by its radial and equatorial segments 120, 125, such as cross members or other structures to reinforce the haptic 110 within the capsule following fusion. Other structures may include T-shaped loops, fenestrated mesh, or a grid or grid-like structure with cross-members that cross the length and/or width of the haptic 110.

The radial and equatorial segments 120, 125 of the haptics 110 can be sufficiently rigid to resist bending by the capsular bag when it fibroses as it encases the haptics 110. In doing so, in addition to centering and enabling fusion of the capsules, the haptics 110 form a skeletal support of the capsular bag that controls the ultimate diameter of the capsular bag during the capsular bag fibrosis and contracture. Typically, the portion of each haptic 110 disposed in the capsular bag becomes rigid as the capsular bag becomes rigid. This rigidity is similar to other fibers trapped in a matrix whereby those fibers which were originally flexible become stiffer from the introduction of the matrix.

In some embodiments, the haptic 110 includes a junction between the radial haptic segments 120 and the optic 105 that is both flexible, allowing the haptic to bend, and is also elastic, in that it returns the haptic 110 to its resting angle when tension diminishes. For example, a portion of the radial segment 120 where it attaches to the optic 105 (e.g., at junction segment 130) may be of a different thickness or of a different material than the portion of the radial segment 120 that extends out from the optic 105. This creates an AD-IOL with a predictable and controlled amount of vaulting and a predictable and controlled diameter in both the maximally vaulted resting state and the totally flattened state under maximal zonular tension.

The haptics 110 can be connected to the optic 105 by various means, depending on the material from which the haptic 110 is constructed. In one embodiment, where the haptics 110 are constructed from surgical suture or wire, the suture or wire can be threaded through the optic 105 from back to front and then back from front to back, for example as shown in FIG. 1. Alternatively, the suture or wire can be threaded through the optic 105 and knotted or otherwise finished off to end like a rivet.

In another embodiment, the individual zonular capture haptics 110 can be embedded into the optic 105, i.e., fused to the optic, during the molding of the optic 105 using methods, for example as are customary in the art at present with 3 piece monofocal IOLs in which haptics 110 are constructed from a different material than the optic 105 and embedded within it. Alternatively, haptics 110 can be connected to each other by a ring structure which can in turn be embedded into the optic 105 during the fabrication of the optic 105. The haptics 110 may attach either at the equator 115 of the optic 105 or within about 0.1 to about 1.5 mm from the equator 115. The optic material can be constructed of usual and customary materials, such as silicone or acrylic polymers, by the current fabrication methods. The embedded haptics 110 may be zonular capture haptics 110 made in accordance with any of the possible embodiments described herein. In some embodiments, to maintain optimal flexibility at the junction of the radial segment 120 with the optic 105, it may be desirable to position the haptic 110 so that its point of attachment to the optic 105 is on the anterior side or the posterior side of the optic 105. By positioning the connection between the haptic 110 and optic 105 on one side of the optic 105, the haptic 110 may be less likely to become trapped between both sides of the capsular bag, and thereby retain its freedom of movement.

The AD-IOL of embodiments of the invention may include one or more optics 105. Optics 105 are generally symmetrical about the optical axis. Examples of suitable optics 105 are well known in the art and can be adapted for use with the zonular capture haptics 110 of the invention. These include optics 105 that are flexible, deformable, foldable, or rigid, preformed or Tillable and which are made from a liquid, solid or semi-solid material. In one embodiment, if a flexible optic 105 is used, it can assist in accommodation not only by anterior-posterior displacement, but also by changing its radius of curvature. Examples of suitable optic materials include silicone(s), acrylics, hydrogels and other inert or biocompatible polymers known to those of skill in the art.

Figure 2:
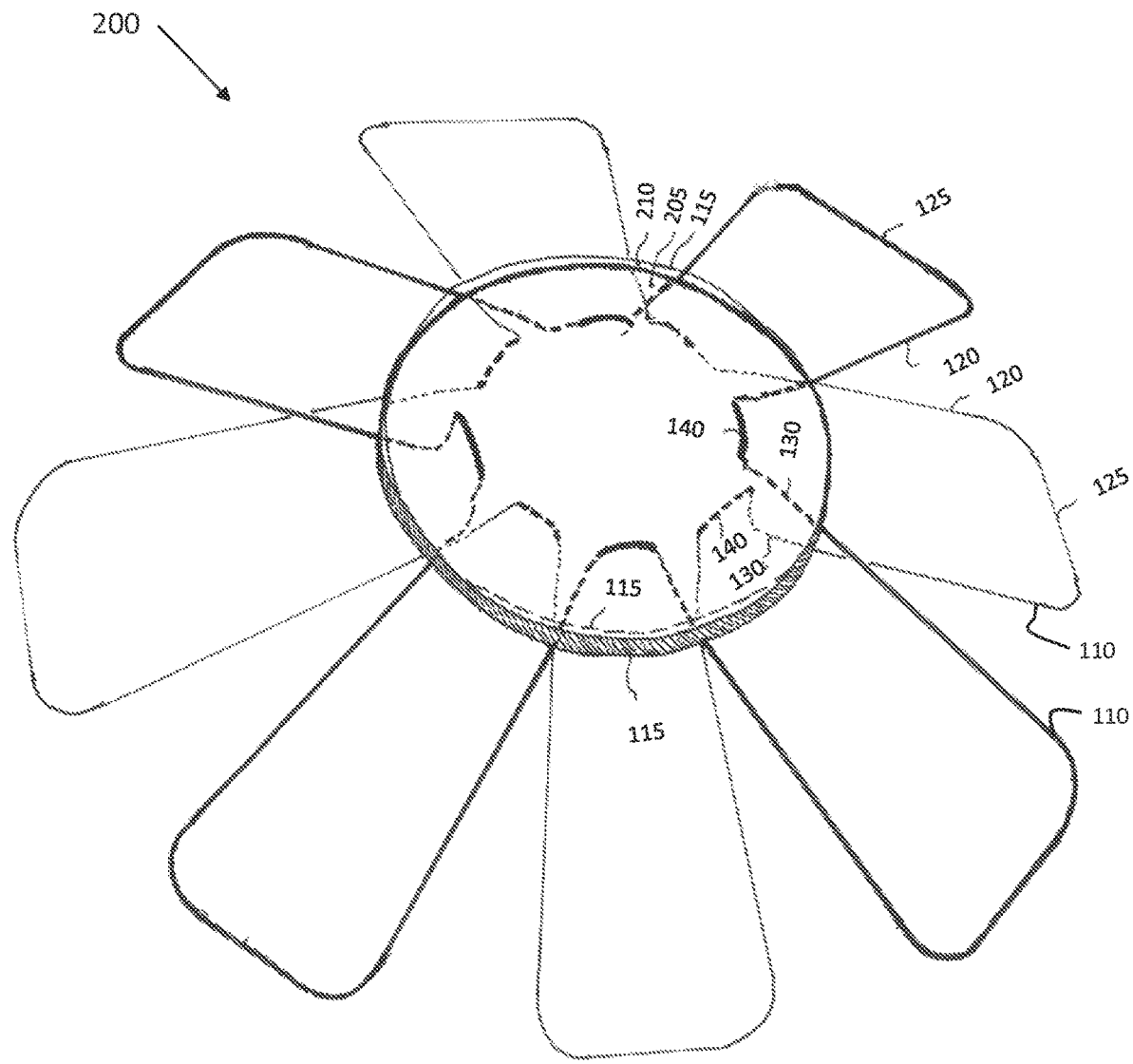
FIG. 2 is a schematic perspective view of an AD-IOL having a fused dual optic, passive fixation ZCH integrated system, with the two optics in close apposition during disaccommodation, in accordance with an embodiment of the invention.
Figure 3:
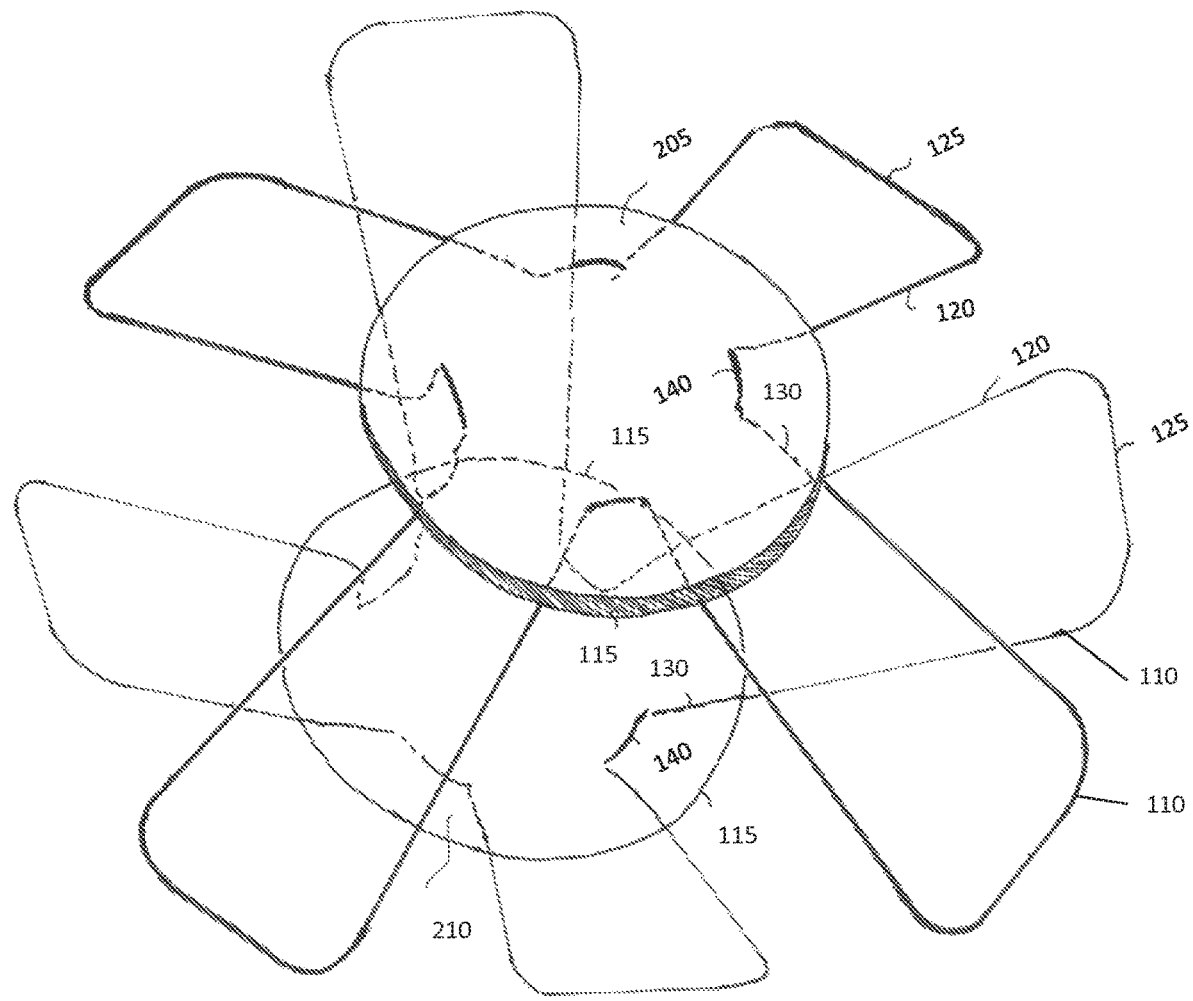
FIG. 3 is schematic perspective view of the AD-IOL of FIG. 2, with the two optics separated during accommodation, in accordance with an embodiment of the invention.

Referring to FIGS. 2 and 3, in certain embodiments, a dual-optic system 200 includes an anterior optic 205 and a posterior optic 210 with integrated zonular capture haptics 110. The haptics 110 may be arranged in an alternating configuration to preserve the space between the haptics 110.

The anterior optic 205 may have a positive optical power and may be implanted with the optic anterior and the haptics 110 angled posteriorly. The posterior optic 210 may have a negative power and may be implanted with the optic posterior and the haptics 110 angled anteriorly. The haptics of each optic may be angled at an angle selected from a range of 0 to 50 degrees, preferably a range of 30 to 45 degrees. The equatorial segments 125 of haptics 110 attached to each optic 205 and 210 may alternate in the capsular bag and not overlap. A sufficient space may be allowed between the radial segments 120 of the haptics 110 of the anterior optic 205 and the posterior optic, to allow capsular sectioning therebetween. The equatorial anterior segments 125 of the two optics 205 and 210 may define a circle with a diameter of 13 mm, i.e., equal to the diameter of the capsular bag, as in FIG. 1. The radial segments 120 may be 5 mm in length as in FIG. 1, but the equatorial segments 125 may be only 2.5 mm in length. The radial junction segments 130 and lateral junction segments 140 may be shorter, e.g., 1 mm in length, as in FIG. 1.

In the dual-optic system 200, during accommodation (as shown in FIG. 3), zonular tension may be released and the haptic systems 110 may return to their resting state (are accommodated) of maximum angulation of the optic attachment, causing the two optics 205, 210 to move axially away from each other, thereby providing increased accommodative amplitude. When tension is applied to the haptics 110 during relaxation of the ciliary body, the haptics 110 straighten (are disaccommodated), thereby causing an axial displacement of the optics 205 and 210 towards each other (as shown in FIG. 2). The two optics may move independently of each other in response to ciliary muscle control.

The AD-IOL may benefit from a ZCH system that employs active fixation to the capsule with interlocking components. Each of the haptics 110 may include a positioning member and a capsule fixing member to effectively sandwich and secure the capsule between the two members. This may generally be achieved by disposing the positioning member within the capsular bag, with its corresponding capsule-fixing member outside the bag. Engaging the positioning member with its corresponding capsule-fixing member preferably keeps a portion of the capsule securely sandwiched between the two members of each haptic.

One function of the haptic system is to assist in centration of the optic 105 within the capsular bag; a second function is to define the capsular bag. Both functions may be achieved by the haptic 110 (positioning member) that is disposed within the bag and extends out from the equator 115 of the optic 105 or optic retainer to the equator of the capsular bag. Haptics 110 may be regularly spaced around the optic 105 or optic retainer with a space between adjacent haptics 110 for sectioning the capsule. The positioning member of each of the haptics 110 typically includes a generally rectangular, trapezoidal or T-shaped loop or loop-like structure. The loop may define an open interior space to allow fusion of the capsule through and around the loop, as discussed below. The positioning member may be disposed in the capsule so that the widest part of the haptic 110, i.e., the distal end, is at or nearly at the equator of the capsular bag. Collectively, the plurality of haptics 110 define a disc that is roughly coextensive with the capsule when implanted, to form a capsule-reinforcing skeletal disc.

Once sectioned, the capsular wedges are coextensive with the haptics 110 to form an articulated skeletal system, where flexion is possible only at the junctions between the zonules and capsular equator at one end, and the junction between the haptics 110 and the optic(s) 105 at the other end. Such an articulated system converts centripetal movement of the ciliary body-zonules into anterior-posterior axial movement of the optic or optics 105.

Figure 4A:
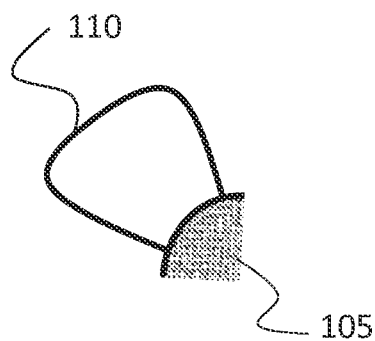
FIGS. 4A-4D are schematic views of different embodiments of capsular fixation haptics of the invention, as loops (FIGS. 4A and 4B) or "T's (FIGS. 4C and 4D) that fix the optic to the capsular bag prior to sectioning and reinforce the capsular wedges after sectioning, in accordance with an embodiment of the invention.
Figure 4B:
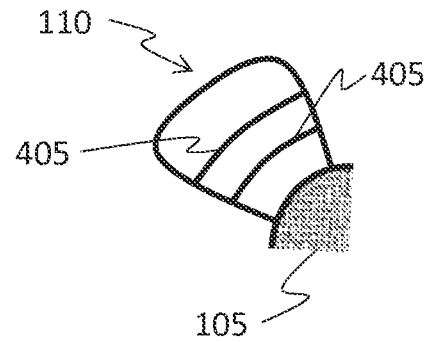
Figure 4C:
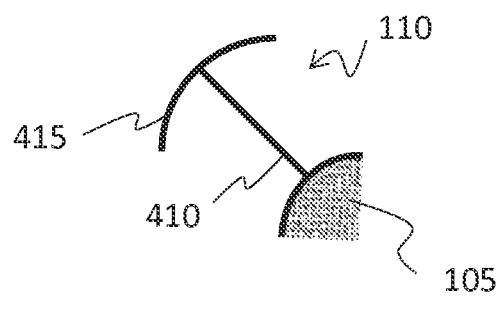
Figure 4D:
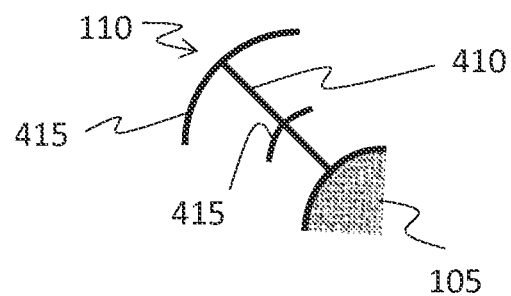

In one embodiment, individual positioning haptics 110 are closed-looped and frame-like extending out from the optic 105 as shown in FIGS. 4A and 4B. One or more cross members, i.e., cross bars 405 may be included that span a width of the haptics 110 near a middle portion of the haptics 110. In another embodiment, these structures are T-shaped with radial members 410 and one or more arms 415 that radiate out from the optic 105, as shown in FIGS. 4C and 4D. The positioning haptics 110 are shown with additional structure to aid in capturing the movement of the capsular wedges.

The number and size of capsule locking haptics 110 of the invention varies depending on the number of sections that the clinician determines to be optimal. In so determining, an optimal number of sections may be determined to be that number that will permit the greatest axial movement of the optic 105 that can be achieved without compromising the integrity of the support. Further considerations regarding the number of sections to be made include allocating an amount of time for sectioning that the clinician feels is appropriate for the safety and well-being of the patient.

In some embodiments, individual haptics 110 are designed to allow contact between the anterior and posterior capsules so that the processes of capsular fusion and fibrosis are not impeded.

In one embodiment, haptics 110 are made of a suitable nonabsorbable surgical material such as surgical wire, suture or the like. The haptics 110 of the invention may optionally include additional structures within the haptic frame, such as cross bars 405 or anchors (for example, as shown in FIG. 4B and discussed below), to reinforce the haptics' ability to grip the capsule and hold it securely. Different parts of the haptics 110 may be made from different materials, some better suited for capsular fixation, some better suited for their elastic or mechanical properties.

Any number of locking mechanisms known to those of skill in the art may be used so that the positioning and capsule-fixing members of the capsular fixation haptics 110 described herein can reversibly or irreversibly lock onto the capsule. In principle a tortuous path may be created, for example, by causing the capsule to undulate over and under one or more cross-members of the positioning and capsule-fixing members (see FIGS. 5C, 6B and 8D). Sharp edges on any of the components of the haptic 110 are preferably avoided so as not to tear the capsule. The haptic components become interlocked to each other by various simple mechanical means and maintain the tension on the capsule trapped in between, in the tortuous path.

For example, a locking component may move posterior to some or all of the positioning haptic component or vice versa, or may be in-line or act by compression. The haptic components shape is such that once they are snapped together, they remain locked in place by mechanical constraints.

The interlocking element of the haptic system can be varied in position from the equator of the capsular bag centrally towards the edge of the capsulotomy opening, i.e., edge of the hole in the middle of the anterior capsule, at any point relative to the point of insertion of the zonules, as it is determined to be more advantageous for any particular accommodative IOL (AIOL) design.

Figure 5A:
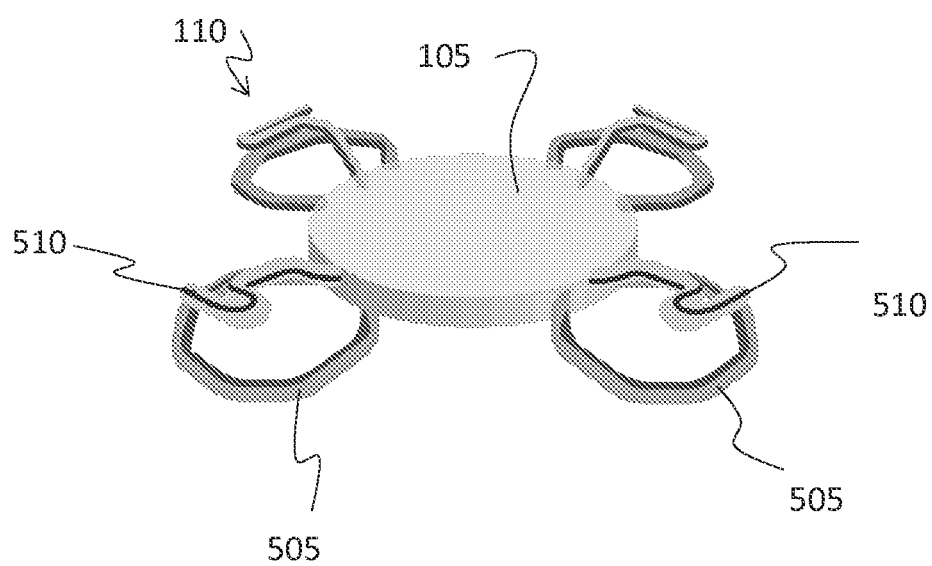
FIG. 5A is a schematic perspective view showing one embodiment of an AD-IOL with a fused single optic and four active interlocking capsular fixation haptics in an open (unlocked) configuration, in accordance with an embodiment of the invention.
Figure 5B:
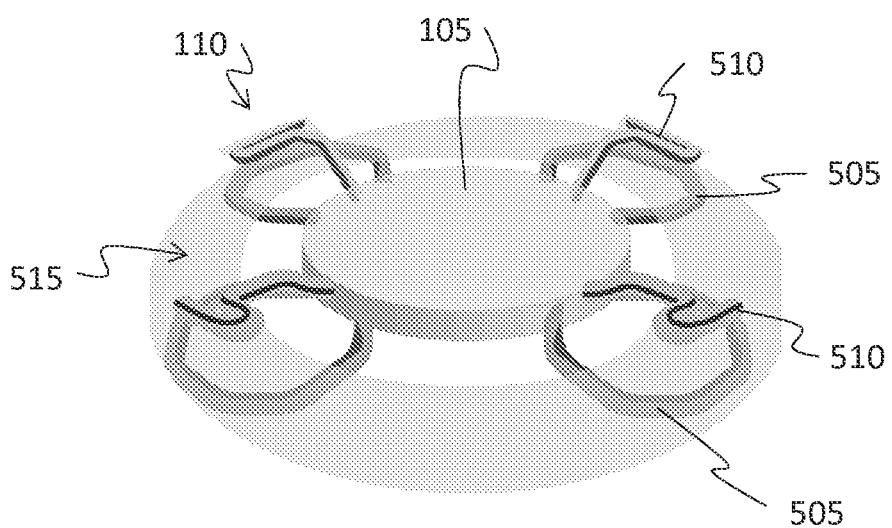
FIG. 5B is a schematic perspective view of the AD-IOL of FIG. 5A disposed within a capsule with capsular fixation haptics in an open (unlocked) configuration, in accordance with an embodiment of the invention.
Figure 5C:
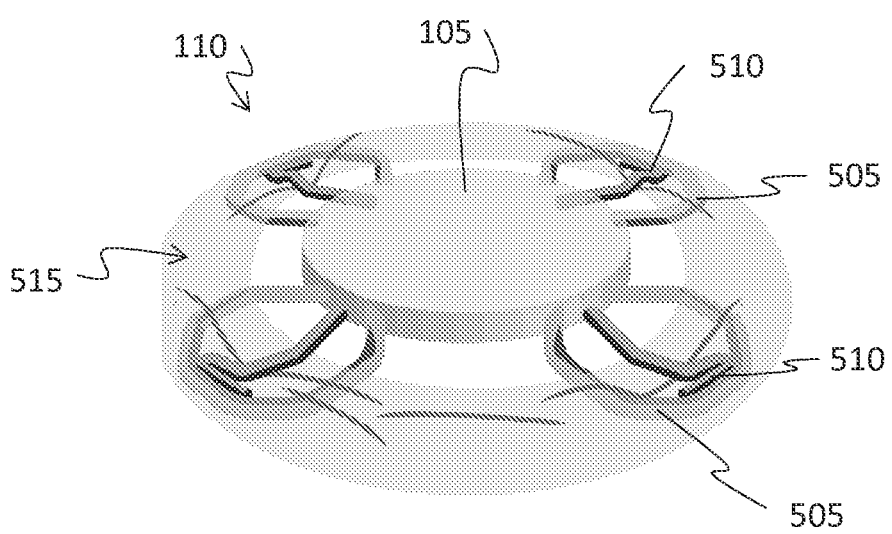
FIG. 5C is a schematic perspective view of the AD-IOL of FIG. 5B with capsular fixation haptics in a closed (locked) configuration, in accordance with an embodiment of the invention.

A prototypical AD-IOL 500 with an actively interlocking capsular fixation haptic system is shown in FIG. 5A. The optic 105 forms the center of the space with the individual positioning haptics 505 creating a shape coextensive with the capsular bag. Each capsular fixation haptic 110 has a positioning component 505 and a capsule-fixing component 510. The capsule-fixing components 510 are shown in their "unlocked" position. The AD-IOL 500 is placed within a capsular bag as shown in FIG. 5B. The AD-IOL 500 may be implanted with the optic 105 at the level of the capsulotomy (opening in an anterior capsule 515), with the positioning component 505 positioned posteriorly to the anterior capsule 515 and the open (unlocked) capsule-fixing components 510 positioned anteriorly to the anterior capsule 515. The capsule-fixing haptics 110 are disposed in the capsule so that positioning members 505 of each haptic 110 are situated inside the bag and the capsule-fixing components 510 are positioned anterior to the anterior capsule 515. The two haptic components are then disposed on either side of the anterior capsule 515. Referring to FIG. 5C, the capsule-fixing components 510 may be closed down on the positioning components 505 and "locked" in place. In the depicted embodiment, the capsule-fixing components 510 have been pressed downward towards and under to engage the positioning components 505, thereby gripping and sandwiching the capsule between the positioning and capsule-fixing components 505 and 510 of each haptic 110.

Figure 6A:
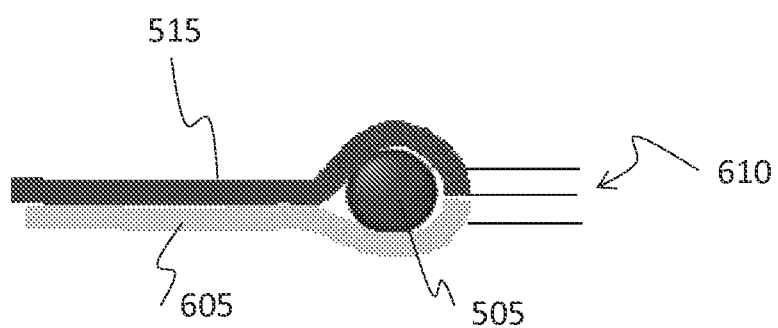
FIGS. 6A and 6B are a cross sectional views of the interaction of the capsule and the components of a passive fixation single haptic in (FIG. 6A) and an active capsular fixation haptic (FIG. 6B) (for example, the haptics of the AD-IOL shown in FIGS. 5B-5C), whereby the haptic locks onto the capsule, and remains locked by virtue of the interlocking geometry, in accordance with an embodiment of the invention.
Figure 6B:
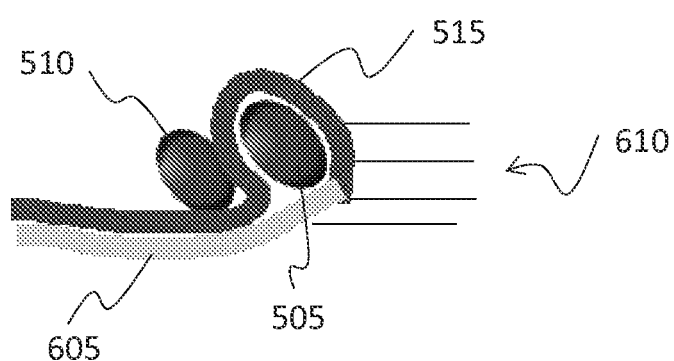

FIGS. 6A and 6B show in cross section how the haptics 110 capture the anterior capsule 515. Initially, the distal end of the positioning member 505 is pushed up to the equatorial edge of the capsular bag (where the anterior capsule 515 joins the posterior capsule 605) where zonules 610 are attached. When the capsule-fixing component 510 is pushed down to and under the positioning component 505, the oblong or angulated profiles prevent the capsule-fixing component 510 from snapping up free of the positioning component 505. The anterior capsule 515 is secured between those two haptic members immediately. When the posterior capsule 605 fuses to the anterior capsule 515 eventually, it cements and reinforces both the mechanical lock and the anterior capsule 515. FIG. 6A illustrates a single loop, passive fixation haptic in a capsular bag, and FIG. 6B illustrates a double loop, active fixation haptic in a capsular bag.

Referring to FIGS. 7A-7F, in an embodiment of a haptic system, the haptics' positioning components 505 may be connected to the optic 105 and inserted as a unit into the capsular bag. A separate unit including the capsule-fixing components 510 is then locked onto the portion containing the haptics' positioning components 505. In particular, FIGS. 7A-7F illustrate front and side views of an AD-IOL in which positioning components 505 of the haptic 110 are separate from the capsule-fixing components 510. Positioning components 505 of the haptics 110 attached to an optic 105 are inserted into the capsular bag. Subsequently, referring to FIGS. 7E and 7F, the independent capsule-fixing components 510 are positioned on the opposite side of the capsule 515 from the positioning components 505, so that each capsule-fixing component 510 engages a positioning component 505, thereby sandwiching the capsule 515 between them to securely hold the optic 105 in position and to maintain the capsule 515 in a maximally actively interlocked conformation. The locking component 510 may attach to the positioning component 505 of this ZCH by means of pins, tabs, or other mechanisms known in the art, and the locking between the two may be permanent and single use, or it may be disengaged and reused multiple times. Depending on the additional intended use, the independent device may also restrain accommodation in addition to actively fixating and interlocking unto the capsule.

In some embodiments, the haptics 110 further include an anchor or other support structure for promoting fusion/fibrosis of the capsular bag and integration of the haptic 110 within the capsular bag. The anchor may be any shape, for example, a parallel bar or T-shaped, or size that is suitable for securing and reinforcing the haptic 110 within the capsular bag. The anchor has the effect of increasing the amount of equatorial haptic length that is subject to zonular forces, thereby increasing the strength of ZCH fusion between capsular fragments. Referring to FIGS. 7A-7F, the anchor may be or include, for example, a cross bar 405 that spans across a haptic 110 parallel to an equatorial segment.

Referring to FIGS. 8A and 8B, the haptic system may be a single unit, in which both positioning and capsule-fixing members 505 and 510 are attached to the optic 105. Initially, the capsule-fixing members 300 of each haptic 110 are at an angle that enables them to be situated outside the capsular bag when the system is placed in the capsular bag. Referring to FIGS. 8C and 8D, once positioning members 505 and capsule-fixing members 510 have been engaged and locked in place, each set of individual haptics 110 forms a tortuous path for the anterior capsule 515 to traverse between the components of each haptic 110. The haptics 110 of these figures have additional members (e.g., cross bars 405) to assist in creating friction or adhesion between the haptics 110 and the capsule 515. For example, first and second clamping members may oppose each other to frictionally hold the capsule in place therebetween.

Referring to FIGS. 9A-9H, a variety of mechanisms may be used for the locking-, positioning-, and capsule-fixing members of the haptics 110 once they are engaged. FIGS. 9A and 9B show an extended arm 905 that controls cross member 910 that locks below the outermost edge of the positioning component 505. The extended arm 905 may be slightly longer than the radius of the loop of the positioning component 505 and may be forcefully bent in the opposite angle when closed. This creates mechanical tension and resists spontaneous opening. FIGS. 9C and 9D show a clip 915 that can lock the positioning component 505 and the capsule-fixing component 510 together, with the capsule-fixing component 510 being inside and slightly below the positioning component 505, thereby trapping the capsular all around the edge of the positioning component 505. FIGS. 9E and 9F show the positioning component 505 likewise clipped into place but ending in a socket 920 along the positioning component 505 before it reaches the optic 105. Any number of hooks, protuberances, recesses, or geometries can be imparted to the two components such as when one is squeezed under or within the other it cannot spontaneously release. This type of structure helps ensure that the positioning and capsule-fixing members 505, 510 of the haptics 110 function as a unit and move together during accommodation. FIGS. 9G and 9H show a capsule-fixing component 510 that wraps around two cross bars 405 of a positioning component 505 of a haptic 110.

In various embodiments, the anterior capsule is sectioned from the edge of the central capsulotomy to the equator of the capsular bag, thereby allowing each haptic member 110 a respective wedge of anterior capsule that may move separately from the others. The posterior capsule may be left intact, may undergo central capsularhexis, or may be partially or completely sectioned radially with cuts matching the anterior capsular sections, at the same or at any subsequent time. Apposition of the anterior and posterior leaves of the capsule to facilitate fusion may also be achieved by introduction of an air bubble posterior to the capsular bag.

In one embodiment, the AD-IOL system has separate interlocking haptic systems for both the anterior and posterior capsule, so that the forces generated on the anterior and posterior capsule can be transferred to the AD-IOL system separately from each other.

In one embodiment, the haptic system is locked on the anterior capsule while the posterior capsule, which is thinner than the anterior capsule, may be left intact, removed centrally, or totally or partially sectioned at any suitable time. Any remaining remnants of the posterior capsule may fuse with the anterior capsule following surgery, and function as a second, biological locking mechanism, essentially sealing permanently the mechanical lock between the double loops of each haptic element. This combined biological and mechanical lock on the capsule provides double secure long term fixation of the haptics 110 of this invention in dynamic system. The force of the zonules is uniformly transmitted to the optic 105 via the entrapped haptics 110.

While locked haptic systems do not undergo a period of fusion and fibrosis, a non-locking haptic AD-IOL may benefit from the haptic system being maintained in a specific conformation during the fusion and fibrosis of the capsular disc. This may be accomplished via chemical means, for example, a maximally accommodated AD-IOL can be achieved by pilocarpine (or pilocarpine like)-induced pharmacologic accommodation, or a maximally unaccommodated lens and atropine (or atropine like)-induced disaccommodation, during some of the period of capsular fibrosis and fusion. This eliminates mechanical strain or movement or distortion of the capsular bag during the fusion/fibrosis phase after the Stage 1 procedure, optimizing the size of the fibrotic capsular disc, sealing of the haptic members in the capsular disc, and reducing any additional tension on the zonules that could have been induced by contraction of the capsular bag. A mechanical restraining device, i.e., a restrainer, may also be additionally desirable to restrain the geometry of the capsular bag and or the state of accommodation of the AD-IOL during capsular fibrosis or after. The restrainer may be single use or multiple use, may be independent or incorporated into the ZCH, and may control the geometry of the bag or the haptics, either as separate devices or as a single multifunction device. In one embodiment, for example, a removable mechanical rod or similar structure may be used to temporarily maintain the AD-IOL in a desired state of vaulting during the capsular fusion/fibrosis period. The restrainer may be disabled or removed at a later stage.

IOL systems that rely on angulated haptics as a mechanism of accommodation may be maintained in an un-accommodated state during fusion of the capsular bag. For example, keeping the optic 105 or optic retainer in a flat planar (i.e., un-vaulted) configuration may allow maximum contact between the anterior and posterior capsules to enhance fusion and eliminate distortion of the capsular bag. In a single optic system, for example, a restrainer may maintain an un-vaulted state in several ways. In one embodiment, the restrainer may be attached or integrated into the haptic system with connectors between haptics 110 that force all the haptics 110 to conform to a position where the haptics 110 are not vaulted. The connector between the haptics 110 in this embodiment may be cut during a second procedure. In another embodiment, one or more rigid restrainers may extend out from the optic 105 to counter the vaulting of each haptic. Each restrainer may be cut during a second procedure. In another embodiment, the restrainer pulls the haptics 110 toward the optic 105 until the haptics 110 are flattened. The restrainer can be cut during the second operation to free the haptics 110 to move.

The AD-IOL of the present invention provides two alternative ways to restrain the accommodation of the AD-IOL. The accommodation restraining devices may be single use devices or reusable and adjustable devices.

In the single use accommodation restraining device, the AD-IOL is maintained in flatter, more planar or less accommodated configuration during the post-implantation period when the anterior capsule fuses to the posterior capsule. This may be accomplished by restraining the angle between the ZCHs and the optic or optic retainer. This configuration may facilitate contact between the anterior and posterior capsules by reducing the separation between the two capsules that may be imposed by the implantation of the AD-IOL. Further, by eliminating accommodative movement of the AD-IOL during the capsular fusion phase, this mechanism further facilitates a strong and predictable adhesion between the anterior and posterior capsules. This restrainer may be permanently disabled at a Stage 2 activation procedure. Several possible device configurations both independent and integrated are described in detail below.

Mechanical constraints to restrain the AD-IOL in a specific conformation may be used. For example, referring to FIGS. 10A-10G and 11A-11D, temporary restraining devices may maintain the AD-IOL in a flat, disaccommodative state during fusion/fibrosis, and may be removed or disabled during the activation Stage 2 procedure. These restrainers control the geometry of the AD-IOL during the fusion fibrosis stage and prevent the haptics from being compressed, distorted, and displaced by the fusion process of the anterior to posterior capsule. They also maintain the AD-IOL in a flattened, disaccommodated state during the capsular fusion to allow better contact between the anterior and posterior capsule during this phase. The combined functions of these devices is to enhance the reliability of the fixation of the haptics 110 within the capsular fused bag and also the reliability of the exact position and geometry of the AD-IOL after the fusion process is complete so that the refractive power of the device is more predictable and less affected by variations in healing factors within the capsular bag.

Figure 12A:
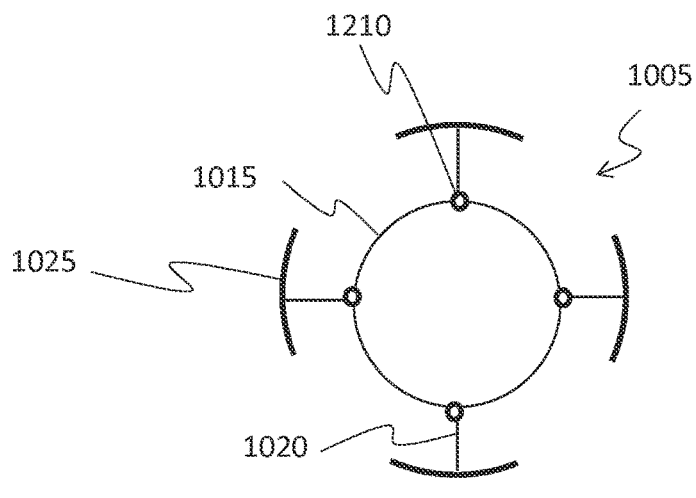
FIGS. 12A-12D are schematic side and top views of reusable restraining devices that maintain the AD-IOL in a flat, disaccommodative state during fusion/fibrosis and are removed during the activation Stage 2 procedure but can redeployed again at any time after, in accordance with an embodiment of the invention.
Figure 12B:
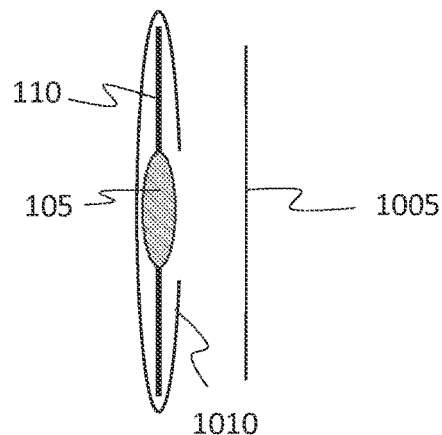
Figure 12C:
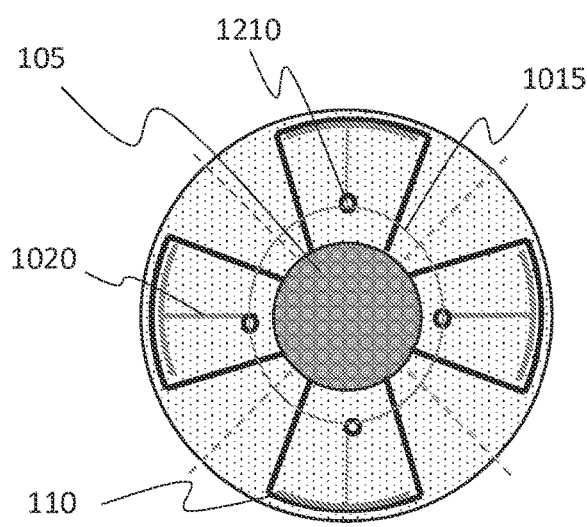
Figure 12D:
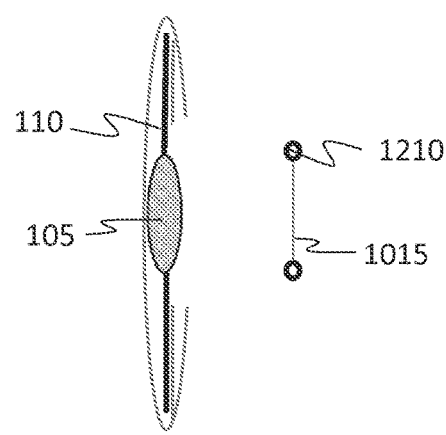

In one embodiment, as illustrated in FIGS. 10A-10F, a restraining device 1005 is positioned in a capsular bag 1010 next to an AD-IOL that includes an optic 105 and four haptics 110. The restraining device 1005 may be positioned either anterior or posterior to the AD-IOL. The restraining device 1005 may include an open ring 1015, having a diameter larger than a diameter of the optic 105, from which radiate four radial members 1020 connected to equatorial segments 1025. The function of this restraining device 1005 is to force the AD-IOL into a flat, unvaulted configuration during the fusion/fibrosis interoperative period, in order to maximize the fusion of the anterior capsule to the posterior capsule and to prevent the fusion process from compressing, distorting or displacing the equatorial segments of the haptics. In this way, the overall geometry of the AD-IOL is maintained in an optimal configuration. During the Stage 2 procedure, when the bag 1010 is cut between haptics 110, the device 1005 may be simultaneously cut the ring 120. The four cut sections of the restraining device 1005 may be left in place as they typically do not interfere with the functions of the haptics 1005. In another embodiment, the restraining features of this device may be built as linking members between the haptics 110 of the AD-IOL, or otherwise integrated within the AD-IOL design (see FIGS. 12A and 12B).

Accordingly, the geometry restraining member, i.e., restraining device 1005, may be configured to maintain a geometry of the plurality of haptics during a fusion contraction phase after the haptics and optic are inserted into the eye, and is adapted to be implanted to cooperate with the haptics and optic. In particular, the geometry restraining member may be adapted to maintain the diameter and the annulation of the haptics during the fusion contraction phase. For example, the radial element or member may have sufficient rigidity to resist contraction of the capsular bag and to prevent distortion of the haptic system. The geometry restraining member may include at least one arm configured to immobilize the haptic system in a disaccommodated configuration during fusion of the capsular bag. As discussed below, in some embodiments, the geometry restraining member may be reusable.

Figures 10E, 10F:
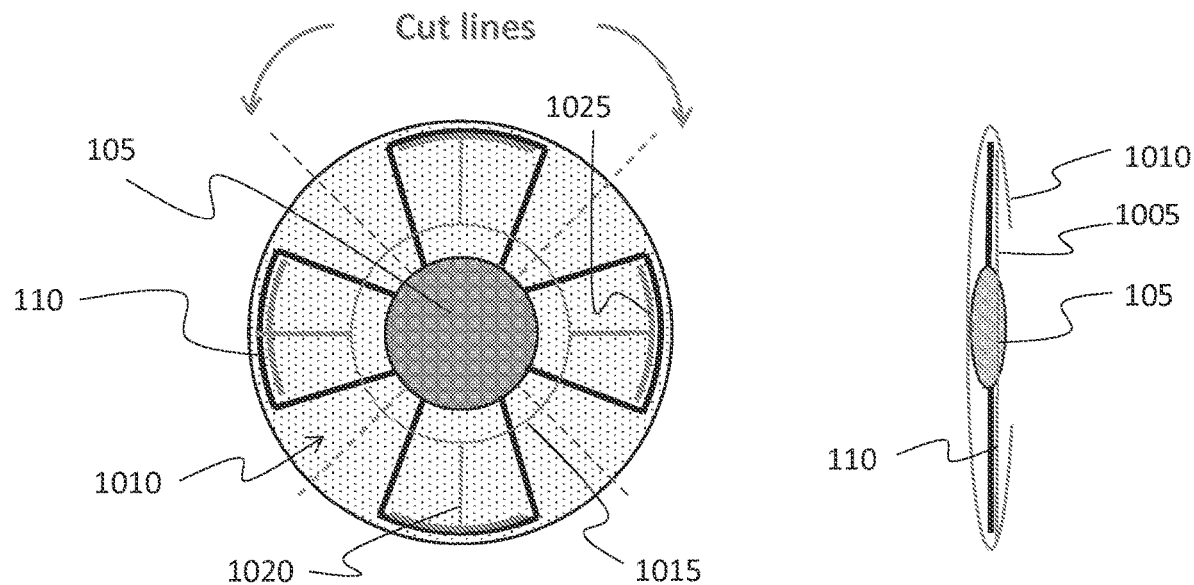
Figure 10G:
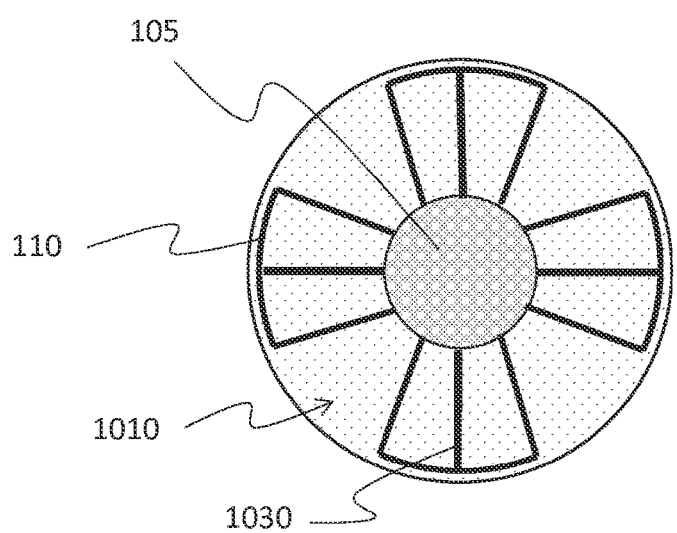

FIG. 10G shows another embodiment of a restraining member 1030 that emanates directly from the optic 105 to the equatorial, as opposed to radial, portion of the haptic 110. This restraining member may be sufficiently rigid to hold the haptic 110 at a prescribed angle to the optic 105. When this rigid member is cut during a Stage 2 procedure, the flexibility of the haptics 110 is restored.

Figure 11A:
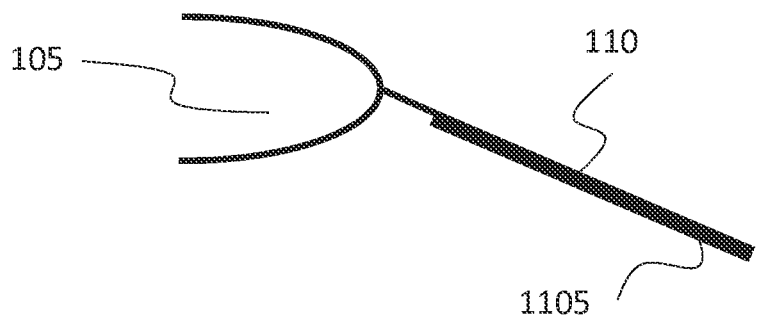
FIGS. 11A-11D are schematic views of additional temporary restraining devices that maintain the AD-IOL in a flat, disaccommodative state during fusion/fibrosis and are removed or disabled during the activation Stage 2 procedures, in accordance with an embodiment of the invention.
Figure 11B:
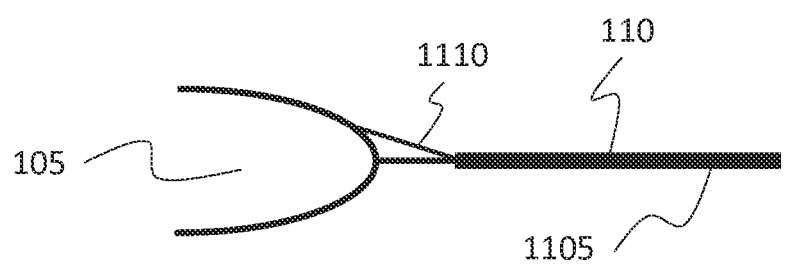
Figure 11C:
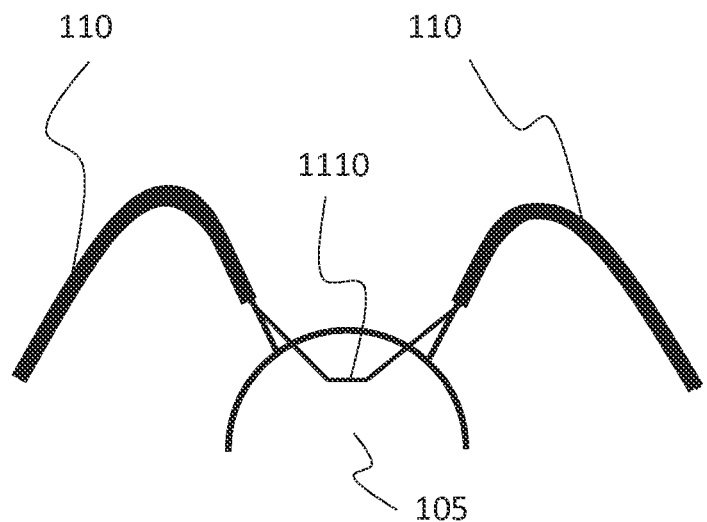
Figure 11D:
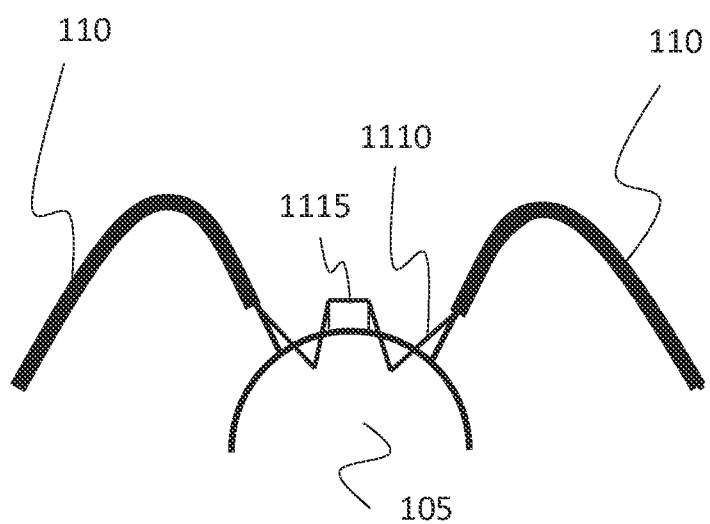

FIGS. 11A-11D show another embodiment of a mechanical restraint on a haptic 110 that changes thickness. The haptic 110 may be made of a thinner material near the optic 105 to maintain flexibility and made of thicker or stiffer material for the portion of the haptic 110 that will become fused inside the capsular bag. In this embodiment, a radial portion 1105 of the haptic 110 may be held in place by a fixed member or string-like connecting material 1110. This has the effect of bending the haptic to a prescribed angle to the optic 105. The fixed member or connecting material 1110 can be cut during a Stage 2 procedure. Referring to FIG. 11D, it may also be advantageous to hold the connecting material 1110 off the surface of the optic 105 and in line with a cut to be made in the capsular bag. In that case, additional posts or holding members 1115 may be used to hold the connecting material 1110 in a position to facilitate being cut and starting the cut for the capsular bag.

In a double optic system, a simple suture ligation or clips may be sufficient to maintain the two optics in apposition to each other, reducing the angle of the posterior and anterior haptics to a flat planar configuration. Such a device may be mechanical or chemical, and may be released by chemical, mechanical, laser, or optical means.

In the reusable and adjustable accommodation restraining device version, the restrainer may be designed to be incorporated in the AD-IOL construction in such a way that it can be set at Stage 1 implantation procedure, to facilitate capsular adhesion, and completely released during Stage 2 activation procedure. However, the restrainer can be reset at any later date in full to eliminate accommodation. The restrainer, alone or in combination with other devices, can alternatively be used to reduce or control the amount of accommodative or disaccommodative movement of the AD-IOL rather than entirely eliminate it. The ability to stop or reduce and adjust the amount of accommodative or disaccommodative movement of the AD-IOL of embodiments of the invention represents an important safety feature to address variability of this complex system. For example, if a patient becomes dissatisfied with the accommodative function of the AD-IOL, or the AD-IOLs in the two eyes are not sufficiently similar in accommodative amplitudes and that creates an unacceptable imbalance, the AD-IOL can be converted into a monofocal IOL by stopping accommodative movement completely, or the accommodative movement may be reduced to match the contralateral eye.

Embodiments of the AD-IOL of the present invention provide for capsular bag geometry and accommodation restraining devices to be embodied as either separate devices or as a single device performing both functions, or to be utilized once and disabled, or to be activated, released, or partially released, singly or repeatedly depending on the requirements imposed by the specific embodiment of the AD-IOL.

In some embodiments, the AD-IOL of the present invention provides two alternative ways to restrain the geometry of the capsular bag mechanically during and after the fusion, healing and contracting phases. A capsular restraining device can be an independent device implanted in addition to the AD-IOL system, or the capsular restraining device can be incorporated into the design of the ZCH itself.

In the independent capsular restraining device version, a restrainer may be implanted in the capsular bag under or above the AD-IOL. The restrainer may consist of rigid radial members 1020, such as rods, that are evenly distributed and attach distally to rigid equatorial segments 1025 that define the same arc of circle as the capsular bag equator and attached proximally to a circular element or open ring 1015 similar in size to the optic 105 of the AD-IOL. The radial members 1020 may be in the same plane or angled with respect to the plane defined by the equatorial plates and the open ring 1015. Depending on the intended geometry restraining features, the dimensions of the various components and the angle between them can be varied, and additional elements added. The restrainer may be permanently disabled at Stage 2 surgery by sectioning the open ring 1015, or it may be temporarily disabled by disconnecting and removing the open ring 1015 from the radial members 1020 if the connection between them is reusable, such as with a pin in hole connector 1210 or similar mechanism, as shown in FIGS. 12A-12D. Then, if needed, the restrainer can be reactivated later by reinserting a new open ring 1015 and reconnecting it to the radial members 1020. The restrainer may be constructed of biocompatible materials known in the art with sufficient rigidity to resist deformation by the contraction of the capsular bag after cataract surgery. Accordingly, suitable materials may be biocompatible metal, metal alloys, polymers such as acrylic or silicone, or other biocompatible materials.

This independent restrainer may be particularly well suited for implantation in conjunction with an AD-IOL that utilized a ZCH that has good tensile strength but is not well suited to resist compression, such as a continuous mesh haptic attached to an elastic optic. Further, in such an embodiment, the central circular element may also separately restrain the accommodative state of the elastic optic with another set of pins or similar mechanisms known in the art.

In the integrated capsular restraining device version, the capsular geometry constraining features are built into the ZCH themselves. The radial elements of the ZCH may be straight and sufficiently rigid to resist deformation along their longitudinal axis, thereby restricting the amount of contraction of the capsular bag. The angle between the ZCH and the optic or optic retainer is controlled by the accommodation restraining device described below, and in combination, the two devices restrain the contraction of the capsular bag geometry to a predictable configuration that allows a precise configuration of the AD-IOL once it is activated and deployed. Such haptics may be constructed from biocompatible materials known in the art that have sufficient rigidity along their long axis and yet sufficient elasticity at right angle to the axis, such as Nitinol materials or other biocompatible materials.

Embodiments of the AD-IOL of the present invention provide two alternative ways to enhance the range of accommodation amplitude, with one or two optics.

In the one optic embodiment, the optic 105 may be rigid or elastic (see, e.g., FIG. 1). Accommodation and disaccommodation may be accomplished by axial movement of the rigid optic 105 or optic retainer anteriorly or posteriorly along the visual axis of the eye, in the response to disaccommodation forces of the eye, by the angulated ZCH's of the invention. If an elastic deformable optic 105 is utilized, accommodation and disaccommodation can be accomplished both by axial movement and also by a change in the curvature of the optic 105 in response to zonular action translated by ZCHs.

In the two optics embodiment, two similar AD-IOLs are implanted, one angled posteriorly with a negative power optic 105, one angled anteriorly with a positive power optic 105 (see, e.g., FIGS. 2-3). The ZCHs of these embodiments allow not only sufficient space for sectioning the capsule between them, but also for the haptics 110 from the paired device to be implanted in an alternating fashion without overlap. A two optic configuration increases the possible accommodation amplitude over a single optic system. All the previous capsular geometry and accommodation restraining devices, or replaceable or fused optics, can be equally well adapted to a single optic or a double optic system.

The intraocular lens system of the invention is made of a biocompatible material, for example, polypropylene, poly (methyl methacrylate), polyamide, nylon, polyester, polyvinylidene fluoride, silicone, stainless steel, nickel titanium alloy such as nitinol, other biocompatible plastics and metals or a combination thereof.

Referring to FIGS. 13A-13B and 14A-14C, an accommodation restraining device, i.e., a restrainer, may be incorporated into the AD-IOL and can be activated and deactivated repeatedly. The ability to lock an AD-IOL into a non-accommodating, fixed configuration represents a safety feature that allows the AD-IOL systems described herein to be converted to the equivalent of a standard monofocal IOL, if the accommodation proves to be troublesome for the patient for any reason.

Figure 15A:
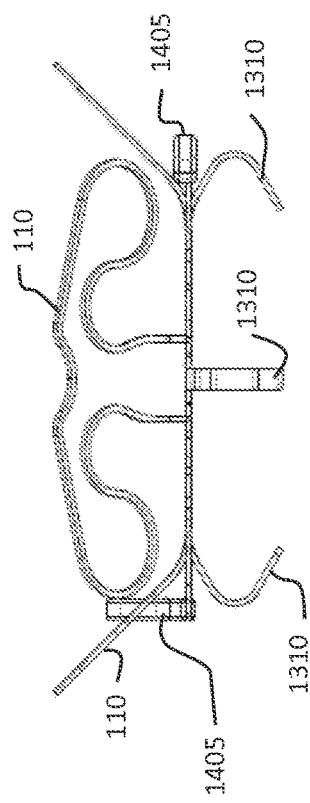
FIGS. 15A-15C are schematic side, top, and perspective views of the haptic system of an AD-IOL of FIGS. 13A-13B further including accommodative/disaccommodative sleeves, in accordance with an embodiment of the invention, in accordance with an embodiment of the invention.
Figure 15C:
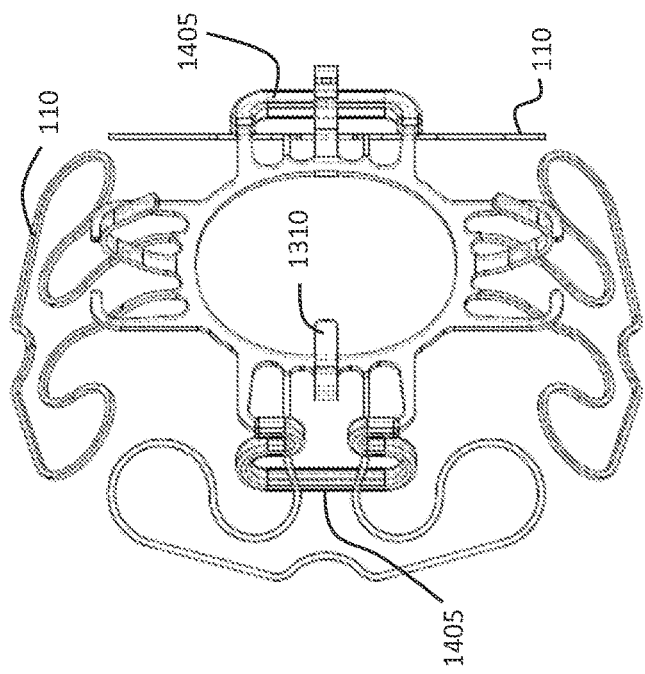
Figure 15B:
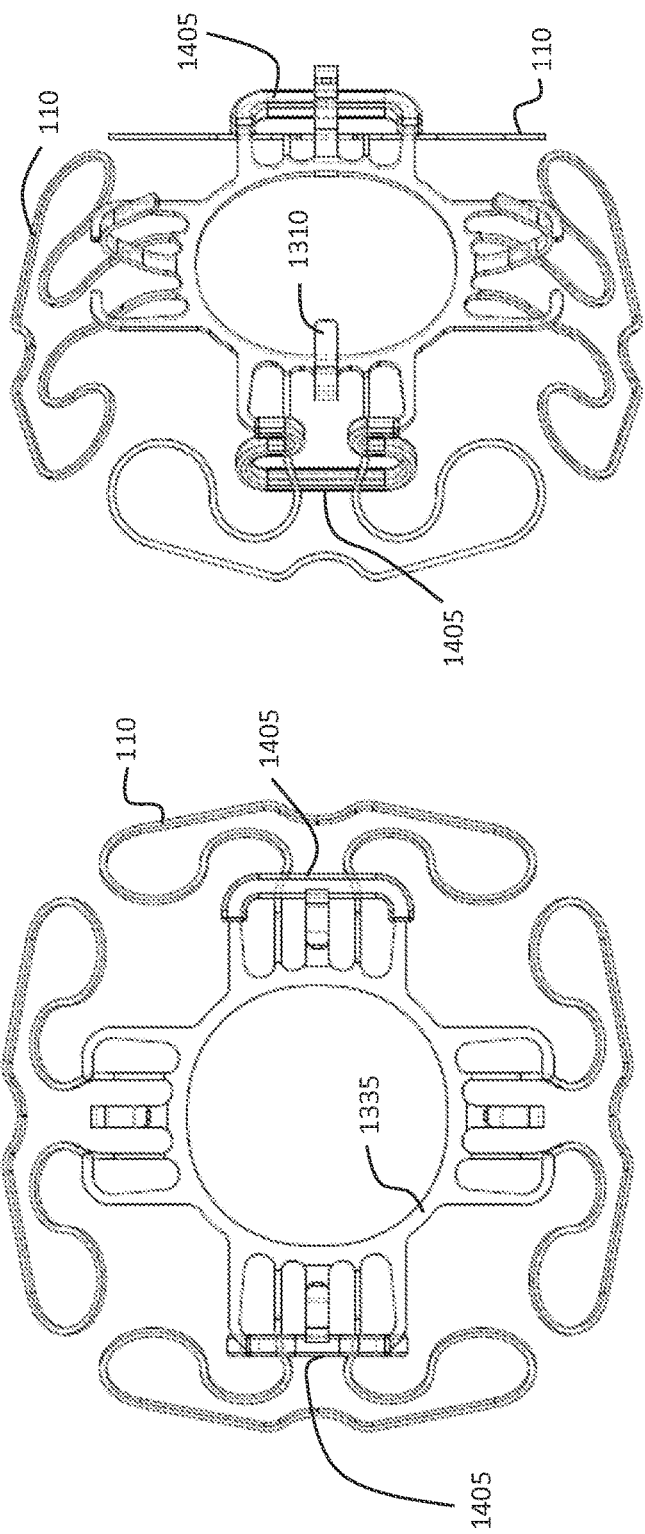

In addition, as illustrated in FIGS. 15A-15C, an extension, such as a sleeve 1405 of variable thickness or length or a similar device, may be threaded through or attached to accommodation restraining arms 1410 to limit the axial travel of the optic 105 or optic retainer and reduce the accommodative or disaccommodative amplitude. A sleeve 1405 of varying thickness between the haptics 110 and the restraining arms 1410 may limit and adjust the disaccommodative flattening of the system, whereas a sleeve 1405 of varying lengths extending from the restraining arms 1410 under the haptic 110 may limit and adjust the amount of possible angulation of the haptics 110, or accommodative amplitude. The accommodation restraining components are preferably made of a suitable nonabsorbable surgical material such as metallic surgical wire, polymer suture, or the like. Additional materials from which the restraining components may be made include polypropylene, poly(methyl methacrylate), polyamide, nylon, polyester, polyvinylidene fluoride, silicone, stainless steel, nickel titanium alloy such as nitinol, other biocompatible plastics and metals or a combination thereof. Coupled with the ability to easily change the optic of the AD-IOL, as discussed with respect to FIGS. 15A-19B, this configuration represents a major safety feature allowing a reconfiguration of the refractive and accommodative properties of the AD-IOL without damage to the ZCH system that is secured to the capsular end of the zonules.

The AD-IOL depicted in FIGS. 14A-14C also includes a new feature, a replaceable optic version of the AD-IOL where an optic retainer is adapted to allow repeated insertion and removal of an optic 105, in addition to including zonular capture haptics 110 with all the possible features of the ZCHs. In conventional cataract surgery, biometry measurements of the curvature of the corneal and axial length of the eye are performed followed by calculations to determine the power of the optic 105 that is implanted during cataract surgery. These calculations are typically refined by statistical means in an effort to improve accuracy. Accuracy of IOL power determination may be substantially affected by pre-existing large refractive errors of the eye or prior refractive surgery. Every individual IOL model has a specific constant that reflects the "effective lens position" for that particular model after the IOL is implanted into the capsular bag. This lens position can vary with various amounts of capsular bag fibrosis or variations in the dimensions of the eye from mean values. Unanticipated errors in the IOL power, if small, are generally compensated by spectacles, in patients having traditional monofocal IOLs. Larger errors may require repeat surgery to replace the entire IOL, or to insert a second piggy-bag IOL. Often IOL replacement surgery is complicated, generally undertaken with trepidation, may cause disruption and loss of capsular bag support, and may necessitate less desirable methods of IOL fixation, such as iris or scleral sutured IOLs or anterior chamber IOLs. However, patients undergoing implantation with accommodative or multifocal IOLs may not tolerate even small errors in optic power calculations. Since surgery that may disrupt the capsular bag is not acceptable in these instances either, such patients routinely undergo corneal refractive surgery after the cataract operation to correct the refractive errors. The replaceable optic of embodiments of the invention allows easy replacement of an optic 105 without damage to the ZCH support mechanism, if it is needed to correct for an unexpected refractive value, or if the patient's postoperative experience requires a different optic type. Such a procedure can be readily incorporated as a small step during the planned Step 2 activation procedure, or performed independently at a different date. The optic retainer may secure a monofocal, rigid multifocal, or elastic multifocal optic 105.

In particular, referring to FIGS. 14A-14C, an AD-IOL may benefit from the ability to change the optic 105 with a simple surgical step and without damage to the ZCH system that is secured to the capsular end of the zonules. In one embodiment, at least one, preferably a plurality of optic securing arms 1310, e.g., curved members, extend anteriorly from the surface of the haptic system, similarly to jewelry prongs that hold in place a precious stone. In a preferred embodiment, at least one optic securing arm is disposed proximate a base of one of the haptics.

Figure 16B:
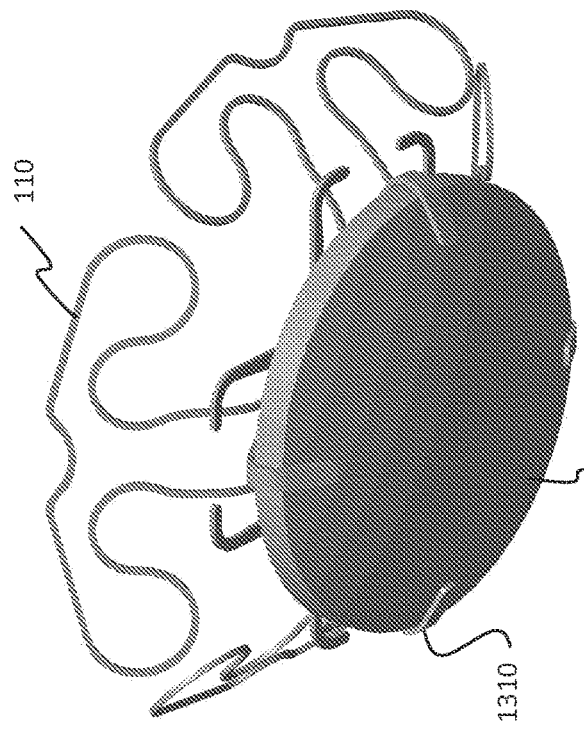
FIGS. 16A-16C are schematic top, side, and perspective views of an optic secured by optic securing arms of the haptic system of FIGS. 14A-14C, in accordance with an embodiment of the invention.
Figure 16A:
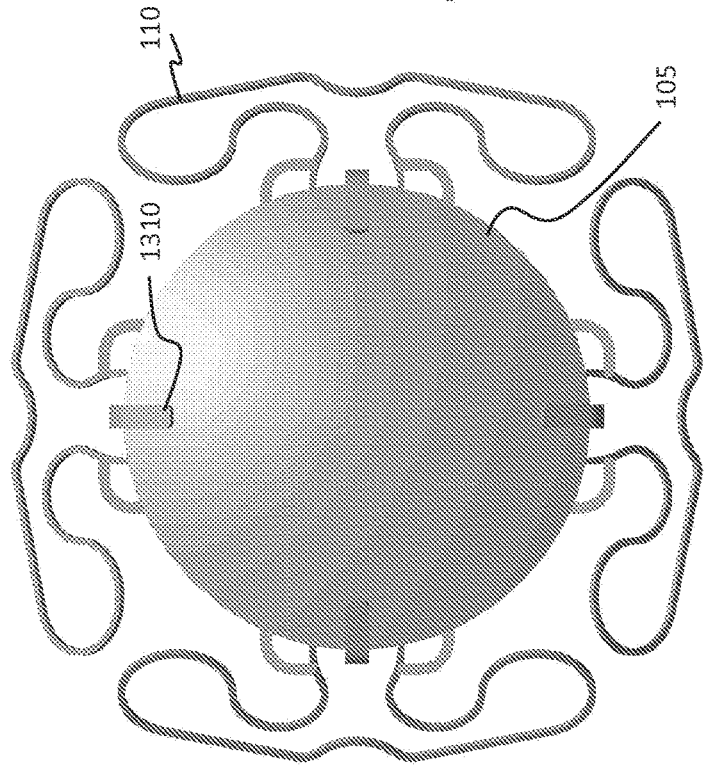
Figure 16C:
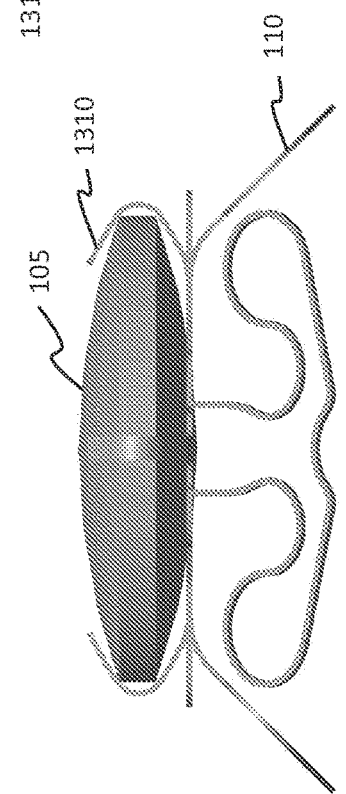
Figure 17B:
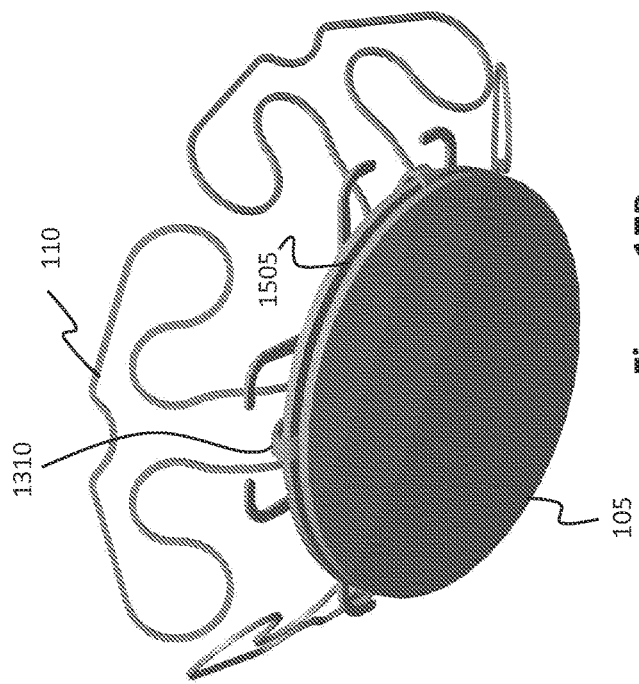
FIGS. 17A-17C are schematic top, perspective, and side views of an optic having an equatorial groove secured by optic securing arms of the haptic system of FIGS. 14A-14C, in accordance with an embodiment of the invention.
Figure 17A:
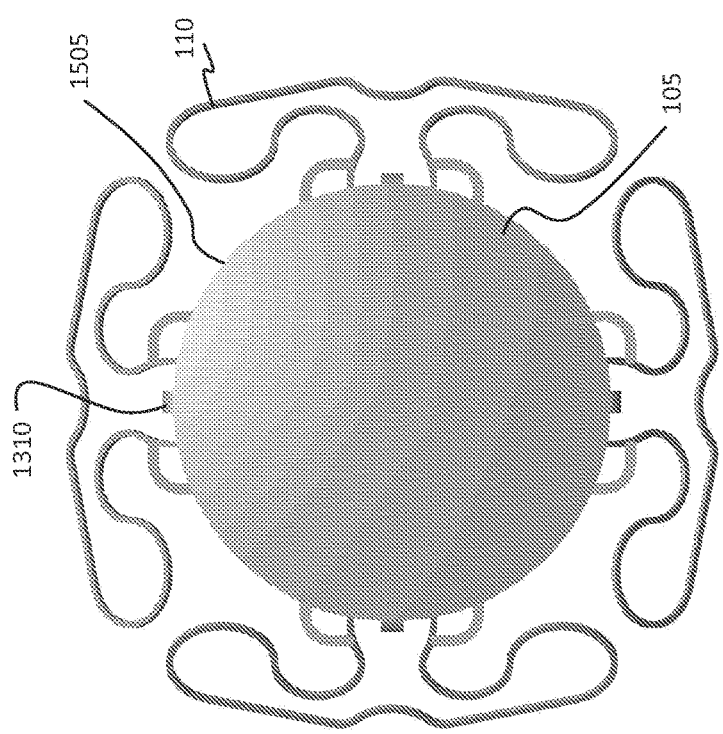
Figure 17C:
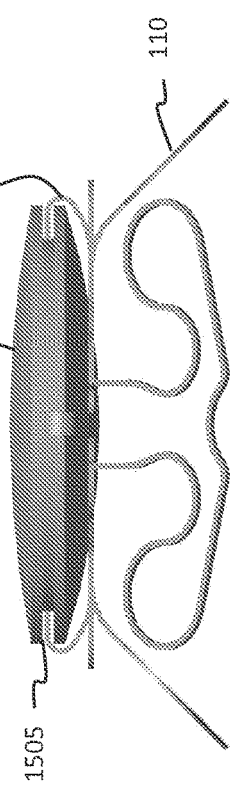
Figures 18A, 18B:
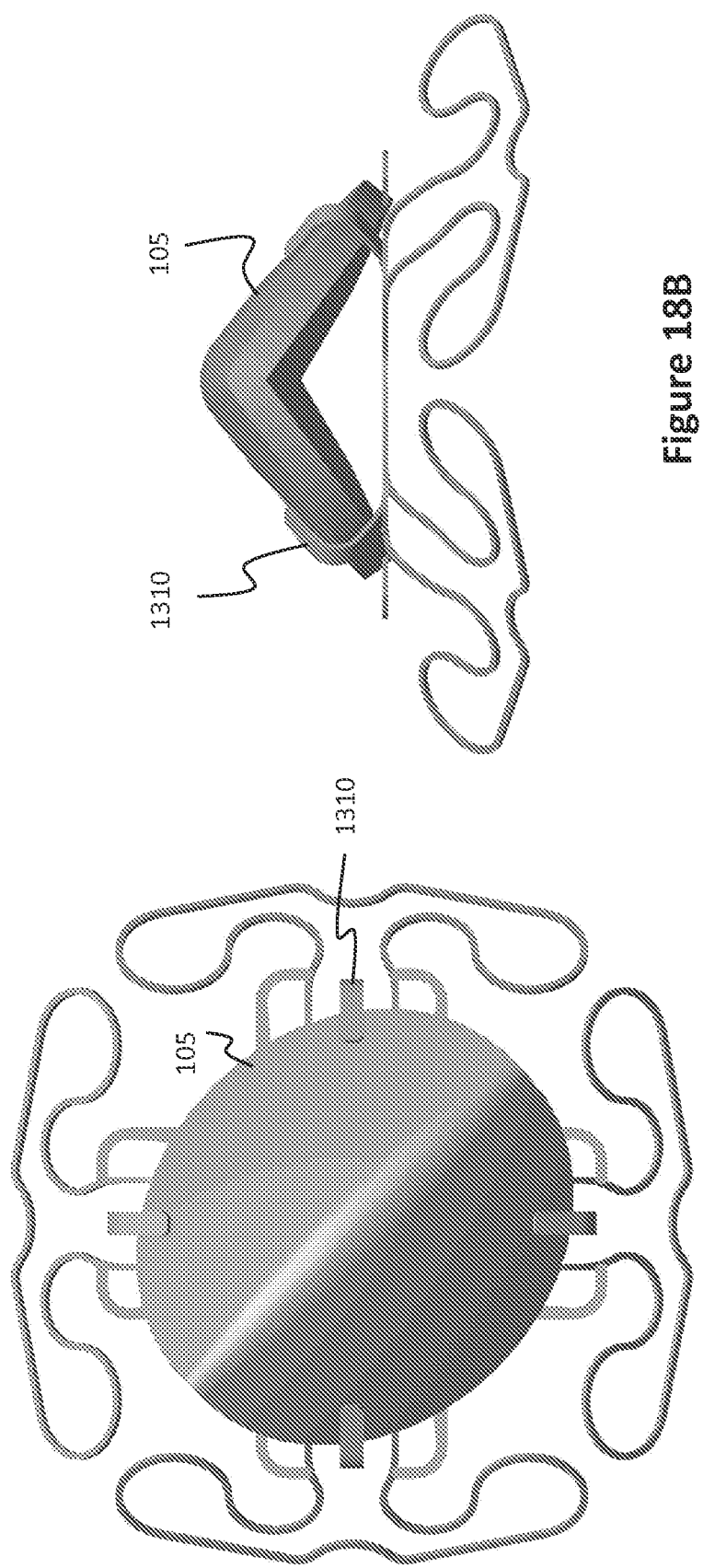
FIGS. 18A-18B are schematic top and side views of a folded optic being installed within the haptic system of FIGS. 14A-14C, in accordance with an embodiment of the invention.
Figures 19A, 19B:
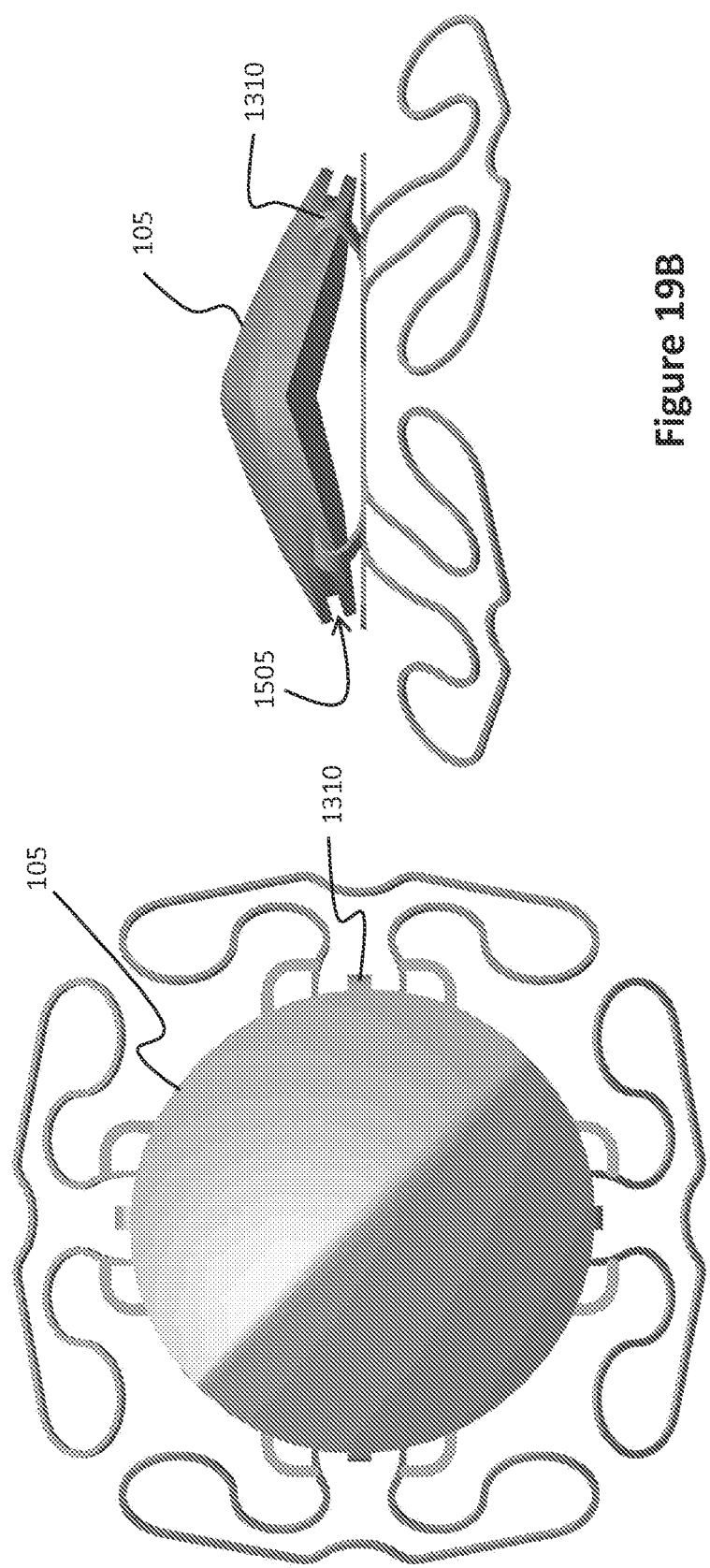
FIGS. 19A-19B are schematic top and side views of a folded optic with an equatorial groove being installed within the haptic system of FIGS. 14A-14C, in accordance with an embodiment of the invention.

The optic securing arms 1310 can secure a monofocal, multifocal, or elastic deformable optic 105. The optic securing arms 1310 may extend over the surface of the optic, as shown in FIGS. 16A-16C. Alternatively, the optic securing arms 1310 may be configured to fit into a groove or notches defined in the optic, e.g., a groove 1505 on the equator 115 of the optic 105, as shown in FIGS. 17A-17C. The groove 1505 may extend for 360 degrees around the optic 105, whereas notches may be depressions or pockets within the optic that are approximately limited to the size of the optic securing arms 1310. In some embodiments, the optic securing arms extend into receiving apertures on the underside of the optic 105 and may have any of a multitude of practical shapes known in the art, such as pins, knobs, tabs, clasps, etc.

The optic securing arms 1310 are preferably made of a suitable nonabsorbable surgical material such as metallic surgical wire, polymer suture, or the like. Additional materials from which the optic securing arms 1310 may be made include polypropylene, poly(methyl methacrylate), polyamide, nylon, polyester, polyvinylidene fluoride, silicone, stainless steel, nickel titanium alloy such as nitinol, other biocompatible plastics and metals or a combination thereof.

The securing arms 1310 are preferably flexible and have shape memory, thereby allowing them to be spread slightly to release or insert an optic 105 and thereafter return to a desired secure configuration.

Referring to FIGS. 18A-18B and 19A-19B, in use, a foldable optic 105, such as the current silicone or acrylic optic standard in the industry, may be folded for insertion into the eye through a small corneal incision, and released and allowed to unfold above the haptic system. The edges of the optic 105 may be positioned under the optic securing arms 1310. Alternatively, the optic 105 may include the groove 1505 for receiving the optic securing arms 1310. Once the optic 105 is flat and fully unfolded, it may be securely fixated to the haptic system, as shown in FIGS. 16A-16C and 17A-17C. If a change of optic is required, the initial optic 105 may be simply cut in two and removed through a small corneal incision and a replacement optic 105 may be implanted in the same fashion as describe above through the same small incision.

Figures 13A, 13B:
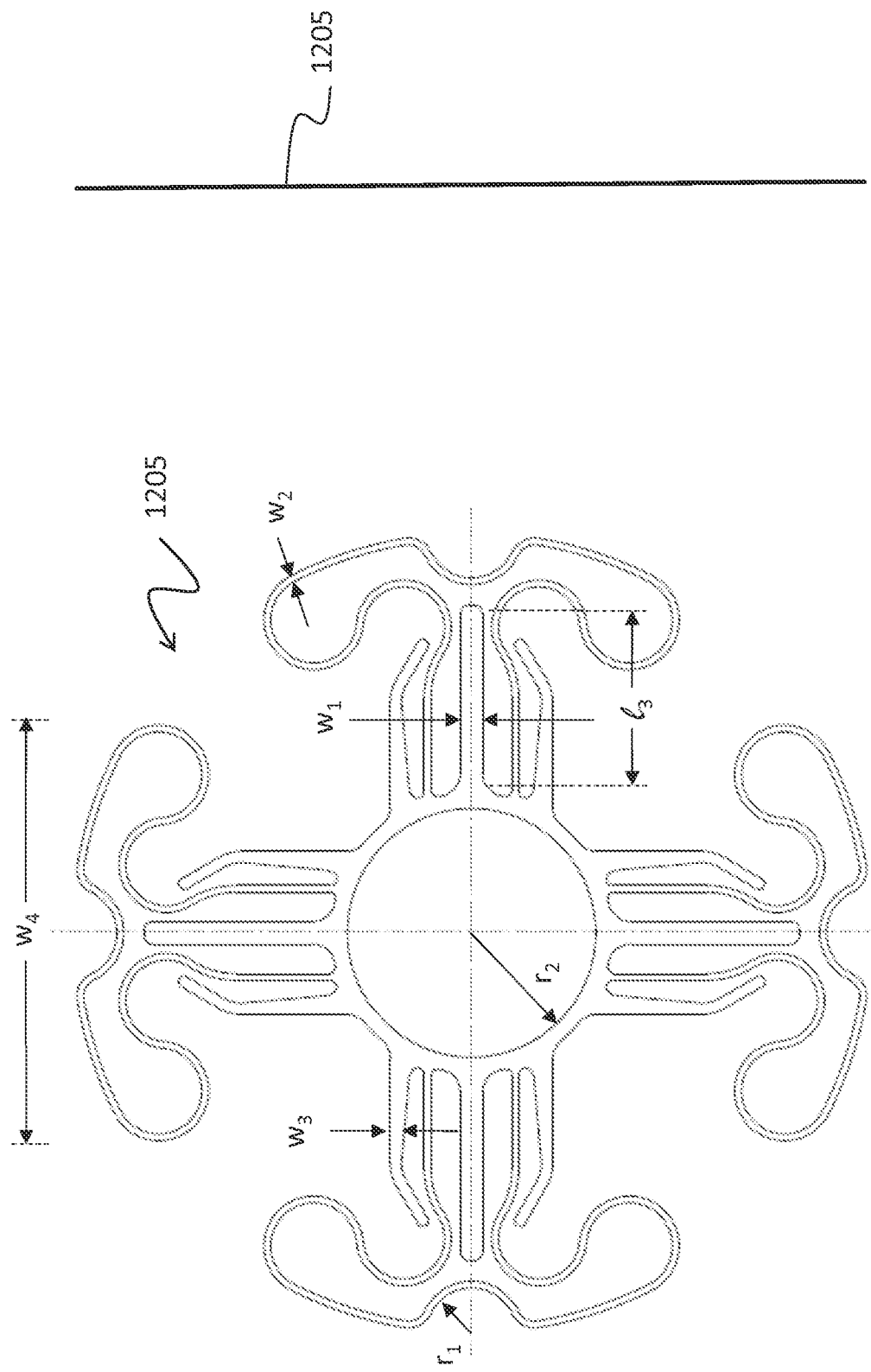
FIGS. 13A-13B are schematic top and side views of a haptic system of an AD-IOL in a flat configuration during a preliminary manufacturing stage, in accordance with an embodiment of the invention.

Referring to FIGS. 13A-13B, in one embodiment an AD-IOL with passive fixation ZCH may be manufactured by cutting a flat piece of material, e.g., a shape memory nickel titanium alloy such as nitinol or stainless steel. Nitinol is a preferred material, although embodiments of the invention may be fabricated from other suitable materials as well. Nitinol is a biocompatible alloy well known for its shape memory and super elasticity and is utilized for a variety of medical implants and surgical instruments. The flat piece of material to be cut may be a sheet of nitinol shape memory alloy, such as nickel titanium alloy material—alloy BB—super-elastic 95%, as per ASTM 2063-05, available from Memry Corporation, Bethel, Conn. The sheet may have a thickness of 0.001" to 0.006", preferably 0.002" to 0.004", e.g., 0.004". The sheet is preferably thick enough to be cut by a laser (a sheet that is too thin may be excessively melted by a laser). The design dimensions may be input into a computer controlling a cutting laser (e.g., the Rofin Fiber Laser system, available from Rofin-Sinar Laser GmbH, Hamburg, Germany), and a flat pattern laser cut from the raw sheet.

Subsequently, the cut-out piece 1205 may be thinned by chemical etching (e.g., in an acid bath) for a predetermined amount of time to reach a thickness of, e.g., 0.002" or to a maximal extent, preferably approximately 0.001", while maintaining structural integrity and predictable dimensions. Preferably, the piece is as thin as possible, e.g., having a thickness from a range of 0.002" to 0.001", for comfort and for appropriate reaction to forces within the eye. Accordingly, in some embodiments, a thinner sheet, e.g., having an initial thickness of about 0.001", may be photo etched rather than laser cut, and then possibly chemically etched to an even smaller thickness, e.g., 0.0005". A suitable photo etching method may be a proprietary process available from Memry Corporation.

The thickness of the cut-out piece 1205 is preferably thinned to achieve a haptic thickness that allows each haptic individually to be completely flattened or disaccommodated by a force of 0.2 grams. This enables the entire device to disaccommodate under overall zonular tension below 1 gram of force.

Thereafter, in stepwise fashion the piece 1205 may be inserted into custom-designed and custom-made shaping tools, e.g., a proprietary method available from Memry Corporation, and heated to the high specific shaping temperature to allow the alloy to retain in memory each addition shaping step and then cooled, until the final configuration is achieved shaping to a final AD-IOL model 1300, depicted in FIGS. 14A-14C. Additional etching and finally electropolishing may be used to render the surface smooth, and substantially without irregularities that may cause structural failure. As the alloy proceeds through a series of processes, balancing the effect of temperature on the material's chemistry is balanced against what each process needs to achieve, to thereby achieve a desired quality in the alloy.

The AD-IOL model 1300 employs many enhancement features described previously: replaceable optic, capsular bag geometry restraining features integrated in the ZCH, secondary retaining anchor incorporated in the haptic design, and a reusable and adjustable accommodation restraining feature. In an embodiment, the AD-IOL model 1300 enables unrestricted disaccommodation, has a maximal accommodative amplitude for a single optic model, has enhanced passive haptic fixation capsular bag geometry control, and is readjustable after Stage 2 surgery by virtue of having replaceable optics 105 and separately adjustable amplitudes of disaccommodation and accommodation Referring to FIGS. 14A-14C and 15A-15C, in an embodiment, the AD-IOL model 1300 includes the following features. The AD-IOL model 1300 may have optic securing arms 1310 designed to hold and allow easy exchange of an optic 105, e.g., a 5 or 6 mm optic. The optic may be inserted into the haptic system after the haptic system is positioned in the capsular bag of the eye, e.g., after the AD-IOL is inserted into the eye and before the capsular bag has fused or any time after. In use, the optic 105 may be implanted in a folded configuration and allowed to unfold into the eye while the edges of the optic 105 are directed under the securing arms 1310. If an optic replacement is needed, the existing optic 105 may be cut in half with intraocular scissors and removed one piece at a time. The same small incision may then be utilized to insert and implant a second optic 105 into the haptic system in the same fashion as was done initially.

The equatorial portion of the AD-IOL model 1300, i.e., the distal ends of the haptics 110, may describe an arc of the same diameter as the capsular bag to precisely capture the zonules. Each of the haptics 110 may have a central notch 1315 to allow easier surgical positioning in the eye. The equatorial portion may double back into two parallel elements 1320, each having a manipulating notch 1325. These elements may function as an additional anchor to double the length of haptic material that is fused between capsules and is subject to zonular forces. Each of the two parallel anchor elements may make a 90 turn and continue with two radial elements 1330 that are attached to a center portion 1335 of the AD-IOL model 1300 at an angle α of about 45 degrees.

The construction of the AD-IOL model 1300 from a ribbon of alloy such as nitinol provides greater rigidity along the plane of the ribbon to radial compressing or stretching forces, and less rigidity across it to bending or flexing forces. The design of the equatorial, anchor and radial elements of the haptic 110 define an integrated capsular bag geometry restraining device. In use, these elements mechanically limit the amount of contraction of the capsular bag.

Two reusable accommodation restraining arms 1410 extend on either side of the radial elements 1330 of the haptics 110, i.e., at a base of one of the haptics so that the haptic is disposed between the first and second restraining arms. In use, the haptic 110 may be pinched at two manipulating notches 1325 at a junction between the anchor and radial elements 1330, thereby decreasing a distance between the radial elements 1330. At the same time the AD-IOL model 1300 may be pressed down or flattened, so that the accommodation restraining arms 1410 are forced below the radial elements 1330 of the haptic 110. The pinching is then released and the distance between the radial elements 1330 is allowed to return to normal width, thereby trapping the haptic 110 on top of the accommodation restraining arms 1410. This procedure allows the AD-IOL to be configured into a flatter, disaccommodated configuration at implantation prior to the beginning of the fusion of the capsular bag phase. This enhances contact between the anterior and posterior capsules and eliminates movement of the AD-IOL during this critical phase.

In some embodiments, the haptic system may increase in diameter with the capsular bag sections during disaccommodation. The capsular bag may fuse through at least a portion of the haptic system, prior to the disaccommodation of the intraocular lens system. Zonules may attach to the haptic system during fusion, with the zonules slackening during disaccommodation. The intraocular lens system may move to a disaccommodated position when the ciliary muscle relaxes or to an accommodated position when the ciliary muscle contracts. In some embodiments, the ciliary muscle may control both a degree of accommodation and a degree of disaccommodation of the intraocular lens system. During disaccommodation of the intraocular lens, a diameter of the haptic system may increase concomitantly with an increase of a diameter of the capsular bag.

At Stage 2 activation surgery, the two manipulating notches 1325 may be squeezed together again, allowing the radial elements 1330 to move in closer and slip posterior to the restraining arms, and then released. This activates the full range of accommodative and disaccommodative movement of the AD-IOL model 1300.

The AD-IOL model 1300 and its features are generally sized to fit within the capsular bag, secure the optic, and provide desired accommodative and disaccommodative movement. In some embodiments, each optic securing arm 1310 has a width $w_1$ from about 0.005 inches to about 0.02 inches. The width $w_1$ is preferably about 0.01 inches. A length $l_3$ of the optic securing arm 1310 may be, for example, from about 0.04 inches to about 0.12 inches, or about 0.08 inches. A width $w_2$ of the material defining the haptics 110 and the notches 1315 may be, for example, from about 0.001 inches to about 0.006 inches, or preferably about 0.003 inches. Each notch 1315 may have a radius $r_1$, for example, of about 0.01 inches to about 0.04 inches, or preferably about 0.02 inches. A radius $r_2$ of the center portion 1335 may be, for example, from about 0.02 inches to about 0.1 inches, or preferably about 0.06 inches. A width $w_3$ of restraining arms 1410 may be, for example, from about 0.002 inches to about 0.01 inches, or preferably about 0.005 inches. A width $w_4$ of the haptic 110 may be, for example, from about 0.08 inches to about 0.2 inches, or preferably about 0.15 inches. The angle $\alpha$ may be, for example, from about 0 degrees to about 50 degrees, from about 30 degrees to about 45 degrees, or preferably about 45 degrees.

The reusable accommodation restraining arms 1410 can be redeployed at any time if the clinician desires to lock the AD-IOL model 1300 into a non-moving configuration. Alternatively, referring to FIGS. 15A-15C, an extension, such as the sleeve 1405, can be inserted on the two opposing restraining arms 1410 about each haptic 110 to limit disaccommodation amplitude by placing a spacer or bumper of adjustable thickness in between the restraining arms 1410 and the haptic 110. In another alternative, a sleeve 1405 of adjustable length limits accommodation amplitude by being inserted on the restraining arms 1410 and under the haptic 110 to limit the amount of angulation of the haptic 110 away from the haptic system like a sling. Thus, the sleeve may act as an accommodation travel reducing sleeve. These sleeves 1405 are preferably designed to slide on the restraining arms 1410 with sufficient friction to be self-retaining once positioned. In between the sliding ends of the sleeves 1405, a disaccommodative spacer may be created from a portion of desired length to create an accommodation limiting sling or of a desired thickness to create a disaccommodation travel reducing sleeve, i.e., a disaccommodation limiting bumper, depending on how much haptic travel is desired for that particular application. Accordingly, the restraining arms in combination with the sleeve allow the haptic system to be tunable to adjust a range of accommodation and/or disaccommodation.

The sleeves 1405 may be manufactured of suitable non-absorbable surgical material such as metallic surgical tubing, polymer tubes, or the like. Additional exemplary suitable materials include biocompatible plastics such as polypropylene, poly(methyl methacrylate), polyamide, nylon, polyester, polyvinylidene fluoride, silicone; biocompatible alloys such as stainless steel, nickel titanium alloy such as nitinol, other biocompatible plastics and metals, or a combination thereof.

Use of AD-IOL ZCH as Dynamometer

In one embodiment, the AD-IOL ZCH device described with reference to FIGS. 14A-14C may be utilized as a static and dynamic dynamometer to measure in vivo forces of disaccommodation and accommodation in the eye in a static or dynamic way. The device has well documented mechanical properties that have been developed both in software modeling and verified on the test bench. For solid modeling, Pro/Engineer software may be utilized. For the analysis and testing, one may use the finite element analysis (FEA) program ABAQUS. Determination of the geometry of the device (angle of bending, equatorial diameter, and position in the eye respective to cornea or ciliary body) may be recorded via ultrasound testing, ocular computed tomography, video-photography or other method of recording known in the art. Maximal accommodation or disaccommodation may be induced pharmacologically and the device position may be recorded by multiple means in this static maximally responsive state. Alternatively, electric stimulation of the Edinger-Westphal nucleus may cause a dynamic change in accommodation or disaccommodation configuration of the AD-IOL platform and is recorded on a live video-recording device that simultaneously records the time and magnitude of the electric stimulus as well. This data generates not only maximal amplitudes but also time response data for both accommodation and disaccommodation. The device geometry is analyzed with software modeling and finite element analysis and physically matched on a twin device on a test bench and measured. By inputting the solid model of the device, along with the material properties and boundary conditions (how it is held and displaced/loaded), the resulting stresses, strains, displacements, and forces are calculated by the FEA program. ABAQUS is well-suited for analyzing nitinol-based devices, since it is able to accurately reproduce stress-strain responses in the material during loading and unloading. The data thus obtained allows measurements in vivo of forces in the eye and dynamic rate of response, information which is currently not available in the public domain. This information is quintessential in designing or perfecting the mechanical properties of any AD-IOL so that it can perform ideally in vivo in a human or in an experimental animal eye.

Figure 20B:
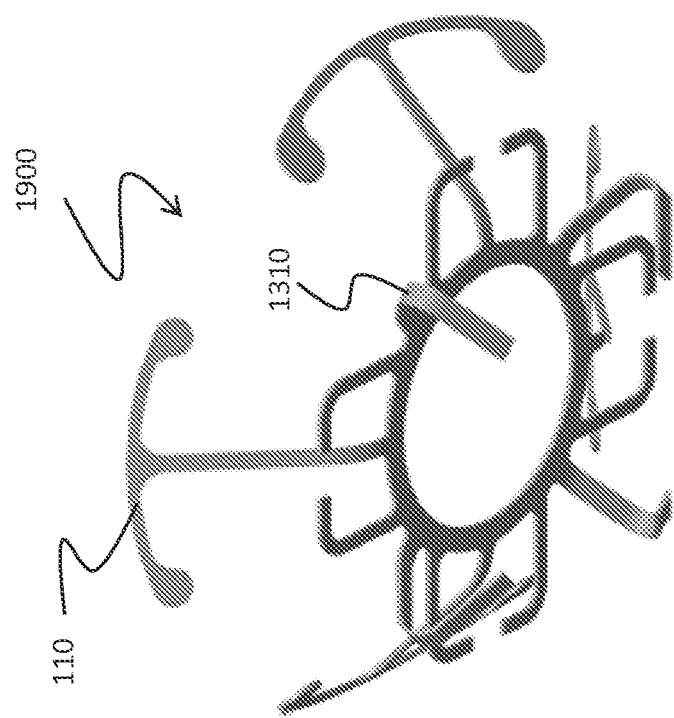
FIGS. 20A-20B are schematic top and perspective views of a haptic system having T-shaped haptics, in accordance with an embodiment of the invention.
Figure 20A:
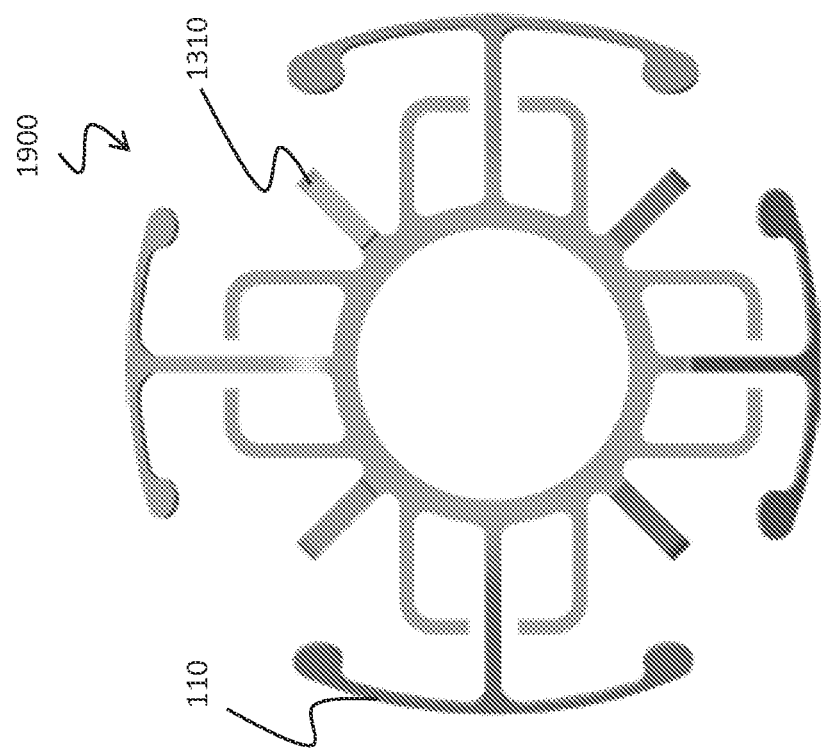

Referring to FIGS. 20A and 20B, in some embodiments, an AD-IOL 1900 includes haptics 110 that are substantially T-shaped. The optic securing arms 1310 may be positioned between adjacent pairs of the haptics 110.

Figure 21B:
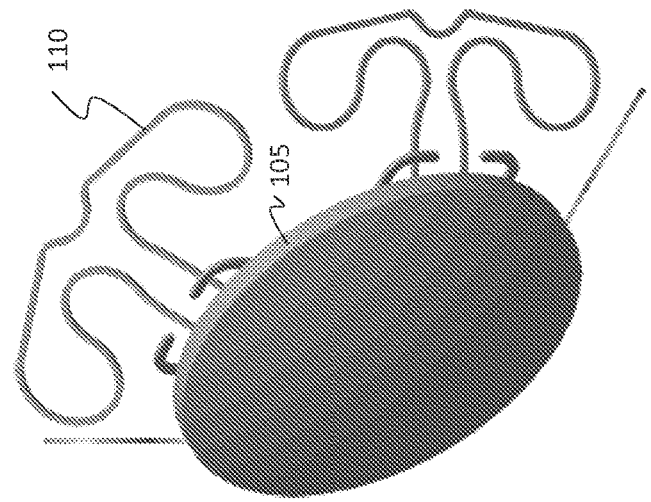
FIGS. 21A-21C are schematic top, perspective, and side views of an optic fused to a haptic system, in accordance with an embodiment of the invention.
Figure 21A:
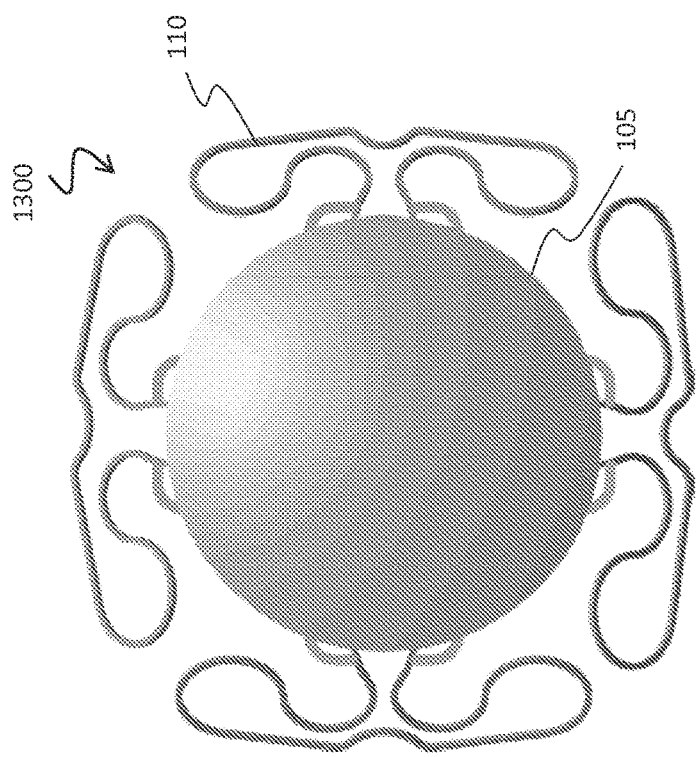
Figure 21C:
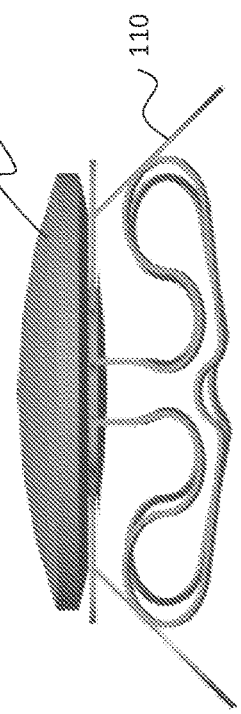

Referring to FIGS. 21A-21C, in some embodiments, an AD-IOL model 1300 may include an optic 105 integrated with the haptics 110, rather than inserted into optic securing arms 1310. The optic 105 in this embodiment is fused or directly attached to the haptics 110 using, for example, adhesives, sutures, mechanical fasteners, and/or a friction fit. In this way, the bulk of the AD-IOL may be reduced, allowing for a larger optic that can still allow the AD-IOL to be inserted through a routine small surgical incision.

In particular, the haptics 110 can be connected to the optic 105 by various means, depending on the material from which the haptic 110 is constructed. In one embodiment, where the haptics 110 are constructed from surgical suture or wire, the suture or wire can be threaded through the optic 105 from back to front and then back from front to back, for example as shown in FIG. 1. Alternatively, the suture or wire can be threaded through the optic 105 and knotted or otherwise finished off to end like a rivet. In another embodiment, the individual zonular capture haptics 110 can be embedded into the optic 105, i.e., fused to the optic, during the molding of the optic 105 using methods, for example as are customary in the art at present with 3 piece monofocal IOLs in which haptics 110 are constructed from a different material than the optic 105 and embedded within it. Alternatively, haptics 110 can be connected to each other by a ring structure which can in turn be embedded into the optic 105 during the fabrication of the optic 105.

Insertion

The anterior capsulotomy performed during phacoemulsification is configured to be slightly larger in size than the optic 105 of the invention. The AD-IOL can be implanted into the eye in the same standard manner that is now customary for cataract surgery.

Referring also to FIGS. 5A-5C, if an active fixation interlocking ZCH embodiment is utilized, the positioning components of the ZCHs may be placed in the capsular bag of the eye, with the locking components anterior to the anterior capsule. In one embodiment, the capsule-fixing member of each haptic is advanced or snapped or crimped or otherwise engaged with the loop of the positioning member, folding a portion of the anterior capsule with it, by means of surgical forceps or other suitable surgical instruments. The capsule-fixing member is now interlocked within the positioning member by virtue of the geometry and design of the members.

Closure of the interlocking haptic members can be accomplished by squeezing them together with a small gauge forceps (for example 23 or 25 gauge) while the iris is dilated and either mechanically retracted or elevated so that the can be visualized by direct or indirect means (for example with a 2e gauge endoscope) as needed Before or after the haptics 110 are locked onto the capsule, cuts may be made in the anterior capsule between the haptics 110, and extending from the visual axis to the outer edge of the capsular disc. This eliminates the restraining effect of any possible future fibrosis on the now segmented capsular bag.

By "sectioning" the capsular disc, greater movement of the optic along the optical axis may be achieved. Each haptic-reinforced section of the sectioned capsule is generally separate from the others, held together by the optic retainer or by the optic 105. As a result of the sectioning, however, the force generated by the zonules is more effectively transmitted to the optic thereby enhancing spatial displacement of the optical element.

Sectioning of the capsular disc can be accomplished by a small gauge (for example, 23 or 25 gauge) trans-conjunctival vitrectomy system with trocars and cannulas placed diametrically opposed to the section line in the capsule/haptic where the section is to be made. A small gauge (for example, 23 or 25 gauge) scissor is introduced through a cannula and used to cut the capsule from the visual axis to the outer edge of the capsular disc. Sectioning may be performed at the Stage 2 activation procedure for passive fixation AD-IOLs or at Stage 1 implantation procedure or anytime after for an active capsular fixation interlocking model.

The AD-IOL of embodiments of the invention moves axially as the ciliary body expands and contracts. In order to gain accommodative ability, the optic 105 typically moves to an anterior position during accommodation and to a posterior position during disaccommodation. Therefore, the AD-IOL is anteriorly vaulted during ciliary body contraction and flat or nearly flat during ciliary body relaxation. In order to achieve this vaulting, the haptics 110 are both radially extending outward from the optic and angled posteriorly to the optic 105 in their natural resting position. Posterior angulation of the haptics 110 to a plane perpendicular to the optical axis of the optic 105 is between 0 and 50 degrees, with the optimal angle of 30 to 45 degrees allowing for optimal axial movement.

The haptics 110 are preferably both flexible (can bend and vary the angle between the haptics 110 and the optic 105 during tension) and elastic (can return to their original angle when tension is reduced). The haptics 110 are formed as loops that are adapted to allow or facilitate fusion of the anterior and posterior capsule following placement of the AD-IOL within the capsular bag and ultimately to permit the sectioning of the fused capsular bag. The haptics 110 are capable of translating the zonular movement from the equator of the capsule bag wedges to the optic 105. The haptics' shape, particularly the equatorial segment, defines the equator of the capsular bag while the lateral edges of the capsular wedges between section lines, and in doing so creating a framework that supports and reinforces each independently moving capsular wedge. Furthermore, this framework creates in essence an articulated skeleton, which allows flexion at the zonular-equator of the bag and haptic-optic junction zones. For example, the haptics may be adapted to become two-joint articulated skeletons replacing the capsular bag after it is dismantled by radial cuts after the intraocular lens system is inserted into the eye. The space between adjacent haptics may be configured to allow the capsular bag, after fusion, to encompass the equatorial and radial segments, to contain the two articulate skeletons. Each haptic 110 may have additional structures, linkers, or other connectors that allow for greater interaction between the haptic 110 and the capsule to ensure capsular capture of the zonular forces and long term adherence of the haptic 110 to the capsule.

A space between each haptic 110 may be reserved for sectioning of the fused capsular bag. The space allows a zone of adherent capsule on the outside of each haptic 110 so that the entire haptic 110 may remain securely embedded within the capsular wedge.

If a passive fixation ZCH embodiment is utilized, the haptics 110 may be inserted into the capsular bag during standard cataract surgery at a Stage 1 implantation procedure.

After implantation, the eye may be maintained in either an unaccommodative or accommodative state by administration of an agent to inhibit or induce accommodation, for example, atropine or pilocarpine, respectively. Alternatively, mechanical means may be used to retain the capsule in a flattened and (unaccommodated) or (accommodated) anteriorly vaulted configuration. Apposition of the anterior and posterior leaves of the capsule to facilitate fusion may also be achieved by introduction of an air bubble posterior or anterior to the capsular bag. Other mechanical, chemical or biological means may be utilized to enhance the adhesion of the anterior and posterior capsule.

Sufficient time is allowed for fusion of the anterior and posterior leaves of the capsular bag around the implanted device. During fusion, each haptic 110 becomes permanently entrapped in the capsular bag; sectioning frees adjacent haptics 110 from each other, with each contained in its own capsular wedge, and the haptics 110 can therefore move independently in response to ciliary muscle and zonular forces on the capsule.

Following insertion, the patient typically undergoes a recovery period of one to six weeks, preferably two to three weeks, for complete fibrosis of the capsule to occur.

In a Stage 2 procedure, the fused and fibrosed capsular bag is sectioned at regular intervals determined by spaces between the haptics 110, to reduce its rigidity, thereby restoring some of the movement lost during fusion of the capsule, fibrosis and formation of the capsular disc. Radial incisions in the capsule are preferably made at regular intervals to define roughly triangular or trapezoidal sections, each of which contains one of the haptics 110 of the AD-IOL. The force of the zonules is uniformly transmitted to the optic 105 via the entrapped haptics 110. The restored elasticity of the present AD-IOL system, which allows the optic 105 to return to a resting state when zonular tension is released, is provided by angulated haptics 110 which straighten under zonular tension and or by direct effect of contracting ciliary body.

The Stage 2 procedure releases the restraining effect of fibrosis on the now segmented, capsular bag. By "sectioning" the capsular disc, greater movement of the optic 105 along the optical axis may be achieved. Each haptic-reinforced section of the sectioned disc is generally separate from the others. As a result of the sectioning, however, the disaccommodative force generated by the zonules is more effectively transmitted to the optic 105.

Any mechanical means or chemically induced tensioning or positioning of the haptic/optic complex, which may have been employed to control the accommodative state of the haptic-lens complex during the fusion and contraction of the healing capsular bag would be removed at this juncture.

In various embodiments, the method of the present invention for the implantation of an intraocular lens, therefore, includes making a plurality of regularly-spaced radial cuts around the capsule/haptics, extending from the visual axis to the edge of the capsular bag. Sectioning alters the rigidity of the capsule following capsular fibrosis/fusion so that the tension and relaxation of the zonules is more effectively converted into axial movement of the optic 105 by the articulated skeleton like structure of the haptics 110 fixated in the capsular wedges.

An accommodation restraining device, if employed, is preferably also removed or released or deactivated at this time allowing the accommodating lens to respond to the zonular tension transmitted by the haptics during relaxation of accommodation, or to return to its resting accommodating state during contraction of ciliary body and relaxation of the zonules.

In Vitro Experiment

An experimental AD-IOL with active capsular fixation interlocking haptics was manufactured from Nitinol wire and embedded into acrylic and silicone optics obtained from commercially available IOLs. Research quality pig eyes were obtained from a local supplier. Under a surgical microscope the corneas were removed. A circular capsularhexis was performed with a bent 25 g needle and forceps. The lens nucleus was removed by aspiration and phacoemulsification in the usual fashion for cataract surgery. The experimental AD-IOL was implanted with the fixation and locking members of each haptic straddling the anterior capsule. The locks were engaged with a 23 g surgical forceps by squeezing the locking member under the positioning member of each haptic. The AD-IOL was now centered in the capsular bag and mechanically fixed to the anterior capsule. The capsule was sectioned in between the haptics of the prototype to the equator of the bag. The optic was grabbed with a forceps and lifted. The AD-IOL remained attached to the wedges of anterior capsule. As the force on the optic was progressively increased, the zonules were ruptured but the capsular wedges remained fixed within the interlocking haptic members.

Experimental Plan

At Stage 1, the treated eye is rendered aniridic by complete surgical removal of the iris. The absence of the iris facilitates evaluation of the haptic systems performance. Standard cataract removal by small, clear corneal incision and phacoemulsification is followed by implantation of the AD-IOL of the invention via standard small incision. The treated eye is maintained in a pharmacologic state of forced accommodation by the administration of pilocarpine drops 4 times per day. This allows the zonules to be free of tension during the healing, fibrosis, contracture phase of the capsular bag. A minimum capsular disc size is thus obtained, which is anticipated to securely incorporate the haptics of the lens holder between the fused anterior and posterior capsules. Once the fibrosis phase is complete, approximately 2-4 weeks after the Stage 1 surgery, the patient is anesthetized again for the Stage 2 surgery.

A 23 or 25 gauge standard vitrectomy instrument is employed. Four trans-conjunctival cannulas are inserted at the standard pars plana location, coinciding with the planned capsular section lines as defined by the location of the spaces between the haptics. A central posterior capsulotomy is performed with the vitrectomy instrument. A 23 or 25 gauge Vitreoretinal scissor is introduced via each cannula to perform radial cuts extending from the edge of the posterior capsulotomy to the equator of the capsular bag, cutting across the fused capsular sheets, to the edge of the capsular disc. The only connection between the sectioned capsules and entrapped haptics is the optic itself.

Administration of pilocarpine drops is discontinued postoperatively. Once the eye has recovered from the surgical intervention, the eye is challenged with pharmacologic accommodation and relaxation of accommodation under anesthesia with short acting pharmacologic agents while the eye is monitored and videographed. It is expected that during relaxation of accommodation, zonular tension is produced and transmitted to the individual segments of the former capsular disc, which now are able to move independently. Each haptic of the lens preferably moves centrifugally and away from each other. When accommodation is induced pharmacologically, the tension of the zonules is released and the elasticity of the inter-haptic loops returns haptics to a closer configuration. A change in diameter of the AD-IOL of up to 1 mm is expected, based on previous experimental data. In previous experimental data, ZCH's without optics, implanted in two eyes of Rhesus monkeys paralleled the movement of the ciliary body in direction and amplitude of movement.

While several aspects of the present invention have been described and depicted herein, alternative aspects may be effected by those skilled in the art to accomplish the same objectives. Accordingly, it is intended that the appended claims cover all such alternative aspects as fall within the true spirit and scope of the invention.

What is claimed is:

1. An intraocular lens system comprising:
a molded optic; and
a haptic system extending from a single side of the optic and comprising:
(i) a haptic system portion having an annular shape integrated with and affixed to the optic prior to implantation in an eye, wherein the haptic system portion is at least one of (a) embedded into the optic by fusion to the optic, (b) embedded into the optic during fabrication of the optic, or (c) fused to the optic, and
(ii) a plurality of radially disposed closed-loop haptics adapted to move independently in response to forces of at least one of a ciliary muscle or zonules of the eye when implanted and comprising a metallic wire forming each closed loop,
wherein the intraocular lens system disaccommodates under a force of below 1 gram.

2. The intraocular lens system of claim 1, further comprising:
a geometry restraining member configured to maintain a geometry of the plurality of haptics during a fusion contraction phase after the haptics and the optic are inserted into the eye, and is adapted to be implanted to cooperate with the haptics and the optic,
wherein the optic has an equator and the plurality of closed-loop haptics projects radially outward from the optic, each of the closed loops of the haptics having an equatorial segment and at least one radial segment and having a proximal end and a distal end relative to the optic, the equatorial segments of the closed loops of the plurality of haptics describe an arc defining a circular disc that is configured for being placed such that the disc is coextensive with a capsular bag of the eye and forming spaces between adjacent closed loops of the haptics.

3. The intraocular lens system of claim 2, wherein each of the haptics comprises a flexible region at the proximal end of the haptic that allows the haptic to move anteriorly and posteriorly relative to the optic.

4. The intraocular lens system of claim 2, wherein the haptics are angled posteriorly.

5. The intraocular lens system of claim 4, wherein the haptics are angled at an angle selected from a range of 30 to 45 degrees.

6. The intraocular lens system of claim 2, wherein the haptics are zonular capture haptics adapted to capture a point of zonular insertion by fusing and becoming integral with an equator of the capsular bag.

7. The intraocular lens system of claim 2, wherein the haptics are adapted to become two-joint articulated skeletons replacing the capsular bag after the capsular bag is dismantled by radial cuts after the intraocular lens system is inserted into the eye.

8. The intraocular lens system of claim 2, wherein the geometry restraining member is adapted to maintain a diameter and an angulation of the haptics during the fusion contraction phase.

9. The intraocular lens system of claim 8, wherein the geometry restraining member comprises at least one arm configured to immobilize the haptic system in a disaccommodated configuration during fusion of the capsular bag.

10. The intraocular lens system of claim 2, wherein the geometry restraining member is adapted to be sectioned and rendered inoperative at a stage two surgery.

11. The intraocular lens system of claim 2, wherein the plurality of radially disposed closed-loop haptics comprises four haptics.

12. The intraocular lens system of claim 1, wherein (a) each closed-loop haptic is affixed to the optic at two points of contact, (b) each closed-loop haptic comprises a maximum width, and (c) the maximum width of each closed-loop haptic is greater than a distance between the two points of contact of the respective closed-loop haptic.

13. The intraocular lens system of claim 12, wherein the maximum width occurs along a length of an equatorial segment distal from the optic of the respective closed-loop haptic.

14. The intraocular lens system of claim 1, wherein at least one closed-loop haptic is rectangular or trapezoidal.

15. The intraocular lens system of claim 14, wherein the at least one closed-loop haptic defines an open interior space to allow fusion of the capsular bag through and around the closed-loop haptic.

16. The intraocular lens system of claim 1 wherein the haptics comprise a nickel titanium alloy and each haptic has a thickness of no more than 0.002 inches.

17. The intraocular lens system of claim 1, wherein each of the radially disposed haptics is adapted to move independently in response to a force of 0.2 grams.

18. The intraocular lens system of claim 1, wherein the haptic system comprises an integrated geometry restraining member configured to maintain a geometry of the plurality of haptics during a fusion contraction phase after the haptics and the optic are inserted into the eye, and is adapted to be implanted to cooperate with the haptics and the optic.

19. An intraocular lens system, comprising:
a molded optic; and
a haptic system extending from a single side of the optic and comprising:
(i) a haptic system portion having an annular shape integrated with and affixed to the optic prior to implantation in an eye, wherein the haptic system portion is at least one of (a) embedded into the optic by fusion to the optic, (b) embedded into the optic during fabrication of the optic, or (c) fused to the optic, and
(ii) a plurality of radially disposed closed-loop haptics adapted to move independently in response to forces of at least one of a ciliary muscle or zonules of the eye when implanted and comprising a polymeric suture forming each closed loop,
wherein the intraocular lens system disaccommodates under a force of below 1 gram.

* * * * *